(12) United States Patent
Page et al.

(10) Patent No.: US 7,947,458 B1
(45) Date of Patent: May 24, 2011

(54) PLACENTAL HUMAN NEUROKININ B PRECURSOR

(75) Inventors: Nigel Page, Reading (GB); Phillip Lowry, Reading (GB)

(73) Assignee: Perinatal Diagnostics Limited, Boldon, Tyne & Wear (GB)

( * ) Notice: Subject to any disclaimer, the term of this patent is extended or adjusted under 35 U.S.C. 154(b) by 437 days.

(21) Appl. No.: 10/130,340

(22) PCT Filed: Nov. 10, 2000

(86) PCT No.: PCT/GB00/04315
§ 371 (c)(1),
(2), (4) Date: Sep. 26, 2002

(87) PCT Pub. No.: WO01/36979
PCT Pub. Date: May 25, 2001

(30) Foreign Application Priority Data

Nov. 16, 1999 (GB) .................................. 9927125.6

(51) Int. Cl.
*G01N 33/53* (2006.01)
(52) U.S. Cl. ........................................ 435/7.1; 436/518
(58) Field of Classification Search .................. 435/7.1, 435/7.2, 7.91, 7.92; 436/516, 518
See application file for complete search history.

(56) References Cited

U.S. PATENT DOCUMENTS

| | | | |
|---|---|---|---|
| 4,665,157 A | 5/1987 | Wright | |
| 4,742,156 A | 5/1988 | Wright | |
| 5,328,927 A | 7/1994 | Lewis et al. | |
| 5,331,089 A | 7/1994 | Curtis et al. | |
| 5,344,830 A | 9/1994 | Mills et al. | |
| 5,360,820 A | 11/1994 | Hagan et al. | |
| 5,491,140 A | 2/1996 | Bruns, Jr. et al. | |
| 5,612,336 A | 3/1997 | Lewis et al. | |
| 5,846,973 A | 12/1998 | Gehlert et al. | |
| 5,985,606 A | 11/1999 | Hillman et al. | |
| 6,689,566 B1 * | 2/2004 | Cantor et al. .................. 435/7.1 |

FOREIGN PATENT DOCUMENTS

| | | |
|---|---|---|
| CA | 2154116 | 1/1996 |
| EP | 0591040 | 4/1994 |
| EP | 0693489 | 1/1996 |
| WO | 9404494 | 3/1994 |

OTHER PUBLICATIONS

Lucas et al. (Neuroscience 1992, vol. 51, p. 317-345).*
Williams et al. (Infect & Immunity 2000 vol. 68, p. 2535-2545; include AntiJen search report.*
Liljeqvist et al. (Abstract only, Journal Gen Virology 1998 vol. 79 (Pt 5), p. 1215-1224; include the attachment of AntiJen Epitope Search report.*
Ngo et al. (1995) "The Protein Folding Problem and Tertiary Structure Prediction, Chapter 14: Computational Complexity Protein Structure Prediction, and the Levinthal Paradox" pp. 492-495 Editor by Merz et al.*
Bork (2000) Genome Research 10:398-400.*
Skolnick (2000) Trends in Biotech. 18: 34-39.*
Smith et al. (1997) Nature Biotechnology 1999 15: 1222-1223.*
Pennica et al (Proc. Nal. Acad. Sci, 95:14717-14722, 1998).*
Haynes et al. (Electrophoresis, 19:1862-1871, 1998).*
Konopka et al (PNAS 83:4049-52, 1986); Summer et al. Neurology 2006, vol. 66, p. 1067-1073).*
Lewin (Genes VI (1997) Chapter 29, pp. 847-848); Gokman-Polar et al (Cancer Research 61:1375-1381, 2001).*
Kangawa, et al., Neuromedin K: A Novel Mammalian Tachykinin Identified in Porcine Spinal Cord, Biochemical and Biophysical Research Communications, 1983, vol. 114, No. 2, pp. 533-540.
Mastrangelo, et al., The Rat Isolated Portal Vein: A Preparation Sensitive to Neurokinins, Particularly Neurokinin B, European Journal of Pharmacology, 1986, vol. 134, pp. 321-326.
D'Orléans-Juste, et al., Neurokinins Produce Selective Venoconstriction Via NK-3 Receptors in the Rat Mesenteric Vascular Bed, European Journal of Pharmacology, 1991, vol. 204, pp. 329-0334.
Garrett, et al., Pharmacological Properties of a Potent and Selective Nonpeptide Substance P Antagonist, Proc. Natl. Acad. Sci. USA, Nov. 1991, vol. 88, pp. 10208-10212.
Moussaoui, et al., Distrubution of Neurokinin B in Rat Spinal Cord and Peripheral Tissues: Comparison With Neurokinin A and Substance P and Effects of Neonatal Capsaicin Treatment, News Science, 1992, vol. 48, No. 4, pp. 969-978.
Henikoff, et al., Amino Acid Substitution Matrices From Protein Blocks, Proc. Natl. Acad. Sci. USA, Proc. Natl. Acad. Sci, USA, Nov. 1992, vol. 89, pp. 10915-10919.
Roccon, et al., Study of SR 142801, A New Potent Non-Peptide $NK_3$ Receptor Anatagonist on Cardiovascular Responses in Conscious Guinea-Pig, British Journal of Pharmacology, 1996, vol. 118, pp. 1095-1102.
Longmore, et al., Neurokinin-Receptor Antagonists: Pharmacological Tools and Therapeutic Drugs, Can. J. Physiol. Pharmacol., 1997, vol. 75, pp. 612-621.
Thompson, et al., Canine Intrinsic Cardiac Neurons Involved in Cardiac Regulation Possess $NK_1$, $NK_2$, and $NK_3$ Receptors, American Physiological Society, 1998, pp. R1683-R1689. Page, et al., Excessive Placental Secretion of Neurokinin B During the Third Trimester Causes Pre-Eclampsia, Nature, Jun. 15, 2000, vol. 405, pp. 797-800.
Walker, Pre-Eclampsia, The Lancet, Oct. 7, 2000, vol. 356, pp. 1260-1265.

\* cited by examiner

*Primary Examiner* — Jacob Cheu
(74) *Attorney, Agent, or Firm* — Mahreen Chaudhry Hoda; Carolyn S. Elmore; Elmore Patent Law Group PC

(57) ABSTRACT

Methods of diagnosing pregnancy induced hypertension or pre-eclampsia by the measurement of the production of neurokinin B, its precursor and fragments thereof are provided, as are kits for use in the methods. Treatments of the conditions and methods of preparing suitable medicaments are also provided as are antibodies and useful antigenic materials.

7 Claims, 20 Drawing Sheets

FIG. 1

THE AMINO ACID RESIDUE SEQUENCE OF THE HUMAN NEUROKININ B PRECURSOR

MRIMLLFTAILAFSLAQSFGAVCKEPQEEVVPGGGRSKRDPDLYQLLQRLFKSHSSLEGLLKALSQASTDPK

ESTSPEKRDMHDFFVGLMGKRSVQPDSPTDVNQENVPSFGILKYPPRAE

FIG. 2

THE AMINO ACID SEQUENCE OF NEUROKININ PEPTIDE

DMHDFFVGLM-NH$_2$

FIG. 3

THE CLONED FULL-LENGTH PLACENTAL cDNA OF THE HUMAN NEUROKININ B PRECURSOR

| | | | | | |
|---|---|---|---|---|---|
| GGCACAGAGC | TGCTCCACAG | GCACCATGAG | GATCATGCTG | CTATTCACAG | 50 |
| CCATCCTGGC | CTTCAGCCTA | GCTCAGAGCT | TGGGGCTGT | CTGTAAGGAG | 100 |
| CCACAGGAGG | AGGTGGTTCC | TGGCGGGGGC | CGCAGCAAGA | GGGATCCAGA | 150 |
| TCTCTACCAG | CTGCTCCAGA | GACTCTTCAA | AAGCCACTCA | TCTCTGGAGG | 200 |
| GATTGCTCAA | AGCCCTGAGC | CAGGCTAGCA | CAGATCCTAA | GGAATCAACA | 250 |
| TCTCCCGAGA | AACGTCACAT | GCATGACTTC | TTTGTGGGAC | TTATGGGCAA | 300 |
| GAGGAGCGTC | CAGCCAGACT | CTCCTACGGA | TGTGAATCAA | GAGAACGTCC | 350 |
| CCAGCTTTGG | CATCCTCAAG | TATCCCCCGA | GAGCAGAATA | GGTACTCCAC | 400 |
| TTCCGGACTC | CTGGACTGCA | TTAGGAAGAC | CTCTTTCCCT | GTCCCAATCC | 450 |
| CCAGGTGCGC | ACGCTCCTGT | TACCCTTTCT | CTTCCCTGTT | CTTGTAACAT | 500 |
| TCTTGTGCTT | TGACTCCTTC | TCCATCTTTT | CTACCTGACC | CTGGTGTGGA | 550 |
| AACTGCATAG | TGAATATCCC | CAACCCCAAT | GGGCATTGAC | TGTAGAATAC | 600 |
| CCTAGAGTTC | CTGTAGTGTC | CTACATTAAA | AATATAATGT | CTCTCTCTAT | 650 |
| TCCTCAACAA | TAAAGGATTT | TTGCATACGA | AAAAAAAAA | AAAAAAAAA | 700 |
| AAAAAA | | | | | 706 |

FIG. 4

```
   1 AGGCTACTGT AGGTAACCAC CCAGCTTGGT TCTTCAGCTC CACATGGTGG GGTTAGGAGA
  61 GGAGGAGGAG GGAGATGGAT GGAACCAATT AGGAACAGCA CCTGGGCTCC TCACAGGAAT
 121 GAACCAGTCA TGCCATTTGC ATGTAAACAG CTTCCCACTT CTCTCCTCAT CCTACCAAAT
 181 GCTCCCAACC CTGGGTTCTG GCCCATGTTC TTTGCCCACA CAGCCCTGTA ATTAGCTGGG
 241 TAATGAGAAG CTTTTAATGA GTCCCATTAG CATCTCGTGT AATAAAGAGG CCTTGAGACC
 301 CAGCTGCTGT CCTCACTTTG GGATGAACAC GGGTCCCTGT GTAGCCAGTG ACTTCTGTCA
 361 GTACAGTCTA AGTTCTCGGA TGGGGTGGGA GACAAACATT TCAGGACCCC AGCAGCACTT
 421 GAGAGGTTCC ATGGTGGATC CATGTTTTTG ACTGTGATAC AAGAAACTTG GCTCTGGCTT
 481 CCTTGTTCAT TTTGTAAATA ACATTTTTTC TTCTTTTAAG AGACAGAGTC TTACTTTGTT
 541 GCCCAGGCTG GAGTGTAGCA ATGCAATTAT AGCTCACTGC AGCCTCAACC TCCTGGGCTC
 601 AAGTGATCCT CCTGCCTCAG CCTCTGGGAT AGCTGGGGCC ACAGGCATGC ACCACCATGC
 661 CTGGCTAATT TTTAAAAATG TTTTTGTAGA GATGGGGTCT TACTTGCTAT GTTGCTCAGA
 721 CTGGTCTCGA ACTTCTGGCT TCAAGCAATT CTCCCACCTC GCCCTCCTAA AGTGCTGGGA
 781 GTATGGGCAT GAGCCACCAT GTCCAGCCTT GTAAATACAT TTTTATTGAG CACCTATTAT
 841 ATGTCAAACA TTATAAAGTG AGGGATACAG TAGCAAACAA AACAGACAAA AATTTTTGCC
 901 ATCATGACAC TTATATTCCT GGGTGGGAGT GGTGATAGAA AGACAATAAG TAAAATACTT
 961 AGCATAGTGG ATGTAATAAG TTCATGAAGG GAAAAATGGG AGTGAGGTAT ATGGAATTTT
1021 GGGGTGGTGA TAATTTTAAA TAGGGTGATT GGGGAATGCT TTGTTGCACA GATTGTTTTT
1081 GTAGTAAATA TGAGATAAAG ATACGGTTCT CTCCCAAACT CAAAATGTAG AAGAGTAGAA
1141 GGTCCCAAAT CTTCAAGTCT CTTGGAGAGG GGGGCCACCC ATTCCGTCTG GGACAGTTAA
1201 CTGTTCCCTC ACAGGTCAAA GTTTATGCCA GTGCAGTAAA AAGAGTGGGA GACCTGGGGT
1261 GAGACAAACC TGGATTTGAG GCTGTTCTTC ACTGATTAGT AGCCATATGT ACTGGAGCAA
1321 GTGACTGAAC CTTCTGAGCC TGTTTTCTCA TCTGGAAAAT CAGAATATTT CCTACTTACA
1381 TGGTCATGGT GATGAAAACC AGATGGACTG CTCCATGCCA AAGCACCCTG CAAACATTCA
1441 AACCCTGCAC CCATTACAAA TACTGGGCTG ACGGATGGCT CTGGCTTTGC TTTTGCATCT
1501 CCGCTGTCTC ATTCAGCAGC AGCATCTGGC TCTGGCTCTC GGCTCTGATC CTGGTTCTGA
1561 CTCTCCCCTG GAGCTCTCTC CCTTGGGTGA GAAATAAGCA GATAATCTCC CTCATCTGTG
1621 TGTGGTGTGA ACAAGAGGCT TGAAAGGTCA GAGAAGAAGA TGCCTGAACT GCAGGGAGAC
1681 AGATTAGAGT GGGGAAAATG TAACTCTGAG GAAAAAGGGA AGCAATTAAG AGATCAAGGC
1741 CAGGGGCAGT GGCTCATGCC TGTAATCCCA ACACTTTGGG AGGCTGAGGC GGGCAGACCA
1801 TGAGGTCAGG AGTTCGAGAC CAGTCTGGCC AACATAGTGA AACCCGTCT CTACTAAAAA
1861 TACAAAAAAA TTAGCCAGGT ATGGTGGTGT GCACCTGTAA TCCCAGCTAC TTGGGAGGCT
```

```
1921 GAGGCAGAAG AATTGCATGA ACCCGGGAGG CAGAGGTTGC GGTGAGCCGA GATTGAACCA
1981 TTGCACTCCA ACCTGGGCAA CAGTGTGAGA CTCTGTCTCC AAAAAAAAAA AAAAAAAAAA
2041 AAATCAAGGC CGGGGAGGGG GCAGGGGTGG CACAGCTATC GAGTTCTGTT CATCCTCTGT
2101 GAGATTACAT CAGGAGGTGT AAAAGAACTC TAGAAGAATG AAGCTAAGTC CAGCTGATTC
2161 AGGGTTCAAG AAGGATTGAG GTGGGAGAGG CATCATGACC ACTGGTGAGG AGTGGAGGAA
2221 GGCCGACACT GGAGCTTTCT TTGCCCAAGC AGAGGAGGGG TGTGACACTC TTGAGGACCA
2281 ATGTAATGGC GCAGCTCCCT CTGGGAGGGG GAAAGGAGAG GACTGGAGGG GATGCTAAAC
2341 TGACCTTCTA ACCTTCAGGG GCCTGAGTCT GGTTGTCCTG GGTGGGGAGG GGCGCCTGCC
2401 TGAAACTGTT TTAGCCCAGA AGTCAGGCCT GAAGGTTAAA GGGCAAGGAG CTGGTGGATG
2461 AACAAGGTGG GGAAAGAGGC CCAGGGTCCA CATCTACTGA GCTGGACTCA GGCATGGGAA
2521 TTGGTGTTGT GAGGGCCAAG ACACTTGGCC TCCTAAAAGT TTGCTGAAAA TCACTGACAT
2581 GAGAGTAATT GATTTATAGG AGAAAAGGTA GATAAATTTA TTTAATATGT ATATATGAGC
2641 ACCTTTAGAA TGAAGACCCA AAGATATAGG GGAAATTGCC AGTTATTTAT TTATTTTTTT
2701 TGGAGATGGA GTCTCACTGT GTCTGCCAGG CTAGAGTGCA GTGGCATGAT CTCGGCTCAC
2761 TGCAACCTCC GCCTGCTGGG TTCAAGCAAT TCTCCTGCCT CATCCTCCTG AGCAGCTGTG
2821 ACTACAGGCA CGCACCACCA TGCCCGGCTA ATTTTTTGTA TTTTTTAGTA GAGACAGGGT
2881 TTCACCATGC TGGCCAGGCT GGTCTGGAAC TCCTGACCTT GTGATCCGCC CGCCTTGGCC
2941 TCCCAGAGTG CTGGGATTAT AGGCATGAGC CACCGCCCCC AGCCTGAAAT CGCCAATTTT
3001 ATGTTTATGT TTTACAAAGT ATGGACAGCT GTGTAGAAAT ATGACTGGAC AGAAGGGCAT
3061 GCTCTAATGT TAACAGACTG AGTGGGGAAA CCCAGGAAGG CCTGTTGAGA TTCCTCCTGG
3121 CCTCTCTCAT TCCTTCCTTC TGGGTATGGG GCAGGACCCT CTCTGGAATG GGGAGATCTT
3181 AGGACCTAAG TTAAATAAGG TAGGTCAGAT AATTTTTTAT GGCCAGTTTT TACATACAGT
3241 AATTTTAGGT TTTATGGCTG GCTTTGGGGA AAAGAGGTCC TGGTTTTTAT AGCTGGCCTT
3301 GGGGGAGAAT GGGACCCAGC AACAGGAGGA CAGGAGAGGG TCAGAGAAAA ACTTCTGCTT
3361 CTGAGGCTGC TACTGAGGCC TTCATTTTAG GGTATTGTCT TCTGAGCCCC AGCATTCCTC
3421 GGTGTGAAAA ATTTTAAAGA AATTTATAG TCCAGAAATT GAGTTGGTGA ATTGTCTTAT
3481 AAGCCATGGA ACTAGTCTCT TAGTCCTGAG AATAGGCCAG TCTAGTTAAA TAGTTATTAG
3541 TTGTGTCTAA TTTTAGGCAG TGTGTTGCAG ATGGGCTTCC ACCAAGCCA GGCCTCTATA
3601 TGATATGAGT AATCAGTTAT TTAGTAAGAG GCATTTTGT CTCAAAAAAT AAATAAATAA
3661 AAATATATGA ATAAATGAAT GTATGTTTCT TATCAGACTA CGTCTGTTCT ATCATTAATT
3721 CCAGAAGGGA GGAGGGTCTG GTTCCCCCTT CCCATCATGG CCTGACCTAG TTTTCAGGTT
3781 AATTTTAGAA CACCCTTGGC TGTGAGGAGT GGTCCATTCG GATGGTTAGG GAGCTTTAGG
3841 ATTTTACTTT TGGTTTACAA AGTAATGTGA ATTAAACAGA CATTTGAGTT AAAGTTTTTA
```

FIG. 4 CONT'D

```
3901 TTTTTTAATA AAATATTTGA TTTAAGCATT TTTTTAACTG AATTAATTAG AGCTCTTTTA
3961 TATATTTTGA TAATGGAACA TTACATACAC AGGCACATAT AAATATATAG ACACATAAAC
4021 AGAAGTAGAG CTTATAGATT TATACTTTTT TTTTTTTTTT TTTTTTAAT GAGACAGGTT
4081 CTCCTTCTGT CATCTAGGCT GGAGTGCAGT GGTGCCATCA CAGCTCACTG CAGCCTTGAC
4141 CTCCAAGGCT CAAGCAATCC TTCTACCTGA CTGGCTAGCT GGGACTACAG GCGCGTGCCA
4201 CCATGCCTGG CTAATTCGTG TATTTTTGT AGATATGGGG AGTTTTACCA TCTTGCCCAG
4261 GCTGGTCTTG AACTCCTGGG CTCAAGAAAT TTTCCTAACT TGACCTCCCA AAGTGTTGGA
4321 ATTACAGGCA TGAGGCACTA CGCCAGACCA GATTTTTAT TTGTCAGTTT CTAGGTAGTT
4381 TTCCCCAACT TCAGACTATC AATTTTTAAA TTATCTGTTT TATGTCTTAA TTATTAACTA
4441 GGCAACTCTA AACTTGTATC TCTAAGACAT GACTTTAGA TGAAATAAGG TAGAAAATGT
4501 ATATTTCAAA GGCATAGAAT TTAGATCTAA ATAAAGGTAA AGTTATCTAA ATTTTAAGCC
4561 ATTGTCTTTT CTATTCTAAA AGGTTTTGGA GGTTTGGGTG TAGAGAGGGA GATGCCTTTA
4621 CAAATGGAAT TTTTGTTGTT GTTTTGTTT TGAGACGGAG TCTTGCTCTG TCACCCAGAG
4681 TCTCGCTCTG TCGCCCAGGC TGGAGTGCAG TGGCACGATC TCCGCTCACT GCAACCTCTG
4741 CCTCCCGGCT TCAAGTGATT CTCCCACCTC AACCTCCTGA GTAGTGGGGA TTACAGCTGT
4801 GTGCCACCAC GCCCAGCTAA TTTTTGTATT TTTAGTAGAG ACCGAGTTTC ACCATGCTGG
4861 CCAGGCTGAT CTCGAACTCC CACCTCAGGT GATCCGCTCG CCTTGGCCTC CCAAAGTGCT
4921 GGGATAACAG GCATGAGCCA CTGCACCTGG CCTTTTCTGA GTTTTTAAG GAGTCTGAGT
4981 CATTAGAAGT CTTTTCTAGA TTTTTTAAAA ATGTGGTATT GAAGATGGCA AAGAGGAAGG
5041 AGGAATAGGG TGGAGTAAAA GTAAATGGGA GGATAGTTTT TAAGAAAGGA AGTGAATAGA
5101 GACATCAAAC ACATTTTAAA AAAAAGATTT TAGTCTACTG AACAAAATTT TTAAAATAG
5161 GATTTAAAGA GAAAACACAG AAGGCTTTAA AAATATACAC ATAGCTTGAA TATTAGCTTT
5221 TAATTAAGCT GACTTCTAAC CATGGAGCTC TTTAACAAAA ATTCTTTTAA ATTTGTCTCT
5281 CTCCTCCTTT AAAACTTTTT GTAGAGATGG GGTTTCGCCC TGTTACCCAG GCTGGTCTCA
5341 AGTCCGGGCA ACTTCTGGGC TAAAGTGATC TGCCTGTCTC GGCCTCCCAA GTGATAGGAT
5401 TACAGGTGTG AGCCACTGCG ACTCACCTTA AATCTCTTGT TACCAGATTT TAGTTGGGAC
5461 AAATGCTGAT ATTTTAAAAG TCACATAAAT ATTAAGCCGA AAAGGACTGA TTTCTGATTA
5521 GGAAGGAAAC CTAAGCCACG GTGGGAATTT TAATTATTAA ACTGTAAAAT GGAGCAGCCT
5581 CCATTGTTAA TTTTGTATGG AATCCAAAGT GGCAGTTTGA GTGTAATTGT TTTAGGTCAG
5641 GTTTTTGTGC TTTAATTTAA TCAAGACAAT TGTTAAGGAT AGCTGTGACA CTATTATGTG
5701 TCCTTTTAAT TTGATCTATC AATTCTTTAG AACAAGTAAT TTTTTAAAT TTAGGAATTT
5761 TAGTCTAAAG GATTTATCTT TTGGCCATTG ACAATTAGAA TTTTTAATGG GGTATTTAAT
5821 TCCAATAGCA ACTTAATCCA AAGTTTTCTT TATGTCAAAG AAAACAGAAG CCCAGGAGGG
5881 ATGAGACCTT GTAAGACAAA ACTCCCCTAG GAGCTTGGAA TGTTTGAAAA TACATGTGTT
5941 GGGCTCCCAA TCTTTTCATA CTGGCTGTGA TGTTACCTGA AAAATCACAT CCTTTGGATG
6001 GTGGAGACCA AGCGGGAATA TCCCCATCTA GTCACGTCAT GCTCTCAAGG ACATGAGACA
6061 AGAGGGAAAC CTCTCACCCT GTTTTATTT CAGGGACTGG CAGCAAAGTT TGTCATAACA
6121 GAAGTCAGCA TAACCAGAAC CACGAAACTG ACCAGTTTGC AGGGCCAGTT CAAACAGTGG
```

FIG. 4 CONT'D

```
6181 GTTGCAGGCC TGTTCTACCC TAGGGTACCC CTCCTTATGA CAGAACACCA AAAGACAAGA
6241 CAAAAACGAA GGAAAACGGC AACAACAAAA AAGCTATTTC TGAAAGGAAA ATGGCAACAA
6301 CAACAACAAA AGCTATTTCT GAAGGGAATG GGGTCAAACT ATGAATACTT ATACCACAAA
6361 GTACTAAAAA ATATATCAGA CTCACTATAC CAAGGTTAGT CACACACAAA ACCTGTTCTC
6421 TCATTAATCT TACATTTGGA AAGGAAAAGG GAAACAATGA TTTTTACTGT CCACTCATCC
6481 AGAGTCCACA GAGAGAGGAA AACTGGAAAA CTGGGAGTCT GGCAGGAAAT TCTCACTCCT
6541 CTGCTGGCTT GCCAGGTTCC TGTATTTCCT TCTCTGTGGC TTCCAGAAAA GCACAATAGC
6601 TTTGGTGGTC TTATTTGTGA TGCCAAACTG TGGTCTTGGC CCCCTAAAGT TTCAGTGAAA
6661 ATCACTGACA TGAAGCAGAT TAATAGGGAA AAAGGCATAC AAATTTATTA AATACGAATG
6721 GGAGCCTTTA GAATGAAGCC TTGAAGCTAT AGGGGAAATT GTCTATTTTT ATGTTTAGGT
6781 TTAACAAAGT ATGGACAGCT GTGTAGAAAT ATGACTGGAC AGAAAGGGCA CGATCTAATG
6841 TTAACAGACT GAGTGGGGAA ACCCAGCAAG GCCTGTCTGT TGAGATTCCT CCTAGCCTCT
6901 CTCATTCCTT CCTTCTGGTG TGGGGCAGGA CCCTCTCTGG AATGGAGGTT TTATGACCTA
6961 AGTCAAATAA CGTAGGTCAG ATTTTTTTTT TTTTTTTTTT TTTTTGAGC TGGAGTCTCT
7021 CTGTCAACAG GCTGGAGTGC AGTGGCGTGA CCTTGGCTCA CTGAAACCTC CGCCCCCTGG
7081 GTTCAAGCCA TTCTCCTGCC TTAGCCTCCT GAGTAGCTGG GATTACAGGG GTGTGCCACC
7141 ACGCCCAGCT AATTTTTGTA TTTTTAGTAC AGACAGGGTT TCACCTTGTT GGTCAGGCTG
7201 GTCTCAAATT CCTGACCTTG TGATCCACCT GCCTCGGCCT CCCAAAGTGC TAGGATTACA
7261 GGCGTGAGCC ACTGTGCCCG GCCTTTTTTT TTTTTTTTT TTTTAGGAA GTTGTATTTT
7321 GGGCTTTTTA ACTAGCTTGT TTTTAATTA GATTATTGCC TTTAGGGTGG AGCCCTTTAA
7381 TAAAAAGGGG GAAGAAAACA TAGGTTTTAG GGCCTCATAT TTAAATGGGT AAAGCAGGCA
7441 TAGCTGGAAG GCAGAATACA GAACCCCCCT AATCAAGGAT CTCATTTTTA TATTGAATCC
7501 TAGGCCCCCC AAAAGAGGGA AATGTCATGG GACGAGATGT GTGGCATTTT TATCGAGTGC
7561 CCCACTGTAA AGATGCTCCC CCAAGGCTGG CAGGCAGCCC AGTGCGATT AGCCCACTCT
7621 GTGCTTAGTC TTTTTTTTTT TTTTTTTTT GAGGTGGAGT CTTGCTCTGT TGCCCAGGCT
7681 GGAGTGCAAT GGCGTGATCT CGGCTCAATG CAATCTCTGT CTCGTGGGTT CAAGCGATTC
7741 TCCTGCCTCA GCCTCCCAAG TAGCTGAGAT TACAGGCACC AGCCACTATG CTCAGCTAAT
7801 TTTTTGTATT TTTAGTAGAG ATGGGGTTTC AACATGTTGG CCAGGCTGGT CTCGAACTTC
7861 TGACCCCAAG TGATCCGCCC GCCTCGGCCT CCCAAAGTGC TGGGATTACA GGCGTGAGCC
7921 ACCATGCCTG GCGTGCTTAG CCTATTTTTA ATGGGAGTTT CATCCTCAAT GGTGAGTGCT
7981 TTCATTGTCT TTAGGTGCCC CAGACCATGT TTTTAAAAAT TTAAATGCAC GAAGAAATAA
8041 GTAGCCCTGT ATAGTAGTAA TACTTGTTG TGAATAACTG TCATAAGTCA TCTCTAAAAC
8101 TGTATTTTTT ATCTAGTTAT TATATATGAC TAGCTATATG TCTAGTTTTT TAAATAATAC
8161 AAAGTAATTT ATTTTTGGCA TCCTCAAAAA CCAAAGAGAT TAGGTAATGT AGTGTAGAAG
8221 AGAGCAGAGC TTTAGACCTG AGAAGAATCT GCCCATGACT CGTGAAACTC CACAACGAAA
8281 GTAGGAGACC CCAAAAAAGG GGTGAGTGTC ATCTTTTCTG AATTTTTTTT TTTTTTTAGA
8341 TGGAGTCTTG CTCTGCCACC AGGCTGGAGT GCAGTGGTGC AATCTCGGCT CAGCCTCCCG
8401 AGTAGCTAGG ATTACAGGCA CGCGCCACCA TGACCAGCTA ATTTTTGTAT TTTTAGTAGA
8461 GACAGCGTTT CACCATGTTG GCCAGGATGG TCTCGGTCTC TTGACCTCGT GATCCGCCCG
```

FIG. 4 CONT'D

```
8521 CCTCGGCCTC CCAAAGTGCT GGGATTACAA GCGTGAGCCA CTGCACTCGG CCGGTCAGAT
8581 AATTTTTTTG GCCAGTTTTT ACATAGAGTA ATTTTAGGTT TTATGGCTGG CTTTGGGGCA
8641 AAGGGGTTCT GGTTTTTATA GCTGGTCTTG GGGGAGAATG GAACCGAGTG ACAAGAGGAC
8701 AAGAGAGGGT CAGAGAAAAA CTTCTGCTTC TGAGGCGGCT ATTGAGGCCT TCATTTTGGA
8761 GTATTGTCCT CTAAGCCCCA GCAGTGTCAA ACTGTACACA AACCATACAC AGCAGCCAGC
8821 TCGGGTGCTG TTAGGAAATG GTCTCACTGC TGGGTCTGTG GGGTATGTGT GTGTCTGGGT
8881 GTGTGGCTAC TGTCTGCATC CTCCTCCCCC CTACAGCCTC CCCGCCTCCC CTCCAGCCAC
8941 CCTGGGATTG GTGACTCTCA GCCCCTCCCC TCAGCTCCCC TAGACCCTCC CAGAGCCTTT
9001 ATCAGGGAGC TGGGACTGAG TGACTGCAGC CTTCCTAGAT CCCCTCCACT CGGTTTCTCT
9061 CTTTGCAGGA GCACCGGCAG CACCAGTGTG TGAGGAGAGC AGGCAGCGGT CCTAGCCAGT
9121 TCCTTGATCC TGCCAGACCA CCCAGCCCCC GGCACAGAGC TGCTCCACAG GTAGGCAAGT
9181 GGGAGAATGC TGGATGGACC AGAGCTGGCA CCAGGGGCT GTTATCTCCT GACTGCCCTT
9241 CTTCTTCCTT TTCTTTCATC TGTGTATTGT CAGGCAGCTA CTAATTGTCA ACCCAGAAGC
9301 TGCTGGGTTT AGACCAGGGT CTCAATAAAT CACACCCCCA CAGAAGCCTG CGGGCACTGG
9361 GCACTGATTC CCCCAGTGTT TCTGAGTATT CCAGTTTGCC ACTGCCTTGA CTGTAACTAA
9421 TGCTAGTATC CATTCTCATT TTTTTAATTT TTATTTATTT ATTTATTTAT TTTTTGAGAC
9481 AGAGTTTCAC TCTTGTCACC CAGGCTGGAG TACAATGGCG CGATCTCAGC TCACTGCAAC
9541 CTCCGCCTCC CAGGTTCAAG TGATTATCCT GCCTCAGCCT CCTGAGCTGG GATTACAGGC
9601 ATGCGCCACC ATGCCCAGCT AATTTTTGTA TTTTTAGTAG AGACAGAGTT TCACCATGTT
9661 GGCCAGGCTG GTCTTGAACT CCTGACCTCA AGTGACCCGC CCATCTCGGC CTCCCAAAGT
9721 GCTAGGATTA CAGGTGTGAG CCACTGCGCC CAGCCTATTT CTTTTTTGAG ATGGAATCTT
9781 GCTCTCTCGC CCAGGCTGGA ATGCAGCAAG CATGATCTCG GCTCACTGCA ACCTCCATCT
9841 CCCGGGCTCA AGCCATCCTT CAGCCTCGGC CTCCCCAGTA GCTGAGACCA CAGGCACATG
9901 CCACCACGCC TGGCTAATTT TTTATATTTT TGGTAAAGAT GTGGTTTCAC CATGTTGCCC
9961 AGGCTGGTCT CAAACTCCTG AGCTCAAGTG ATTCACTCGC CTTGGCCTCC CAAAGTGCTA
10021 GGATTACAGG TGTGAGCCAC TGCACCCGGC CTTACCCATT ATCTTTTGAA CATCTACTAT
10081 GCATTAAGCT CTTTACATGC ATTAACTCTA ATACTTTCAA TAACCCTGTG AGGTAGGCTC
10141 TTTTCTTTCT CCCATTTGT AGTTAAAAAG CCAAGGCTCA GAGAGGTTAA ATAACTTGCC
10201 GGGGGTTCCA CAGCTGTAAG TGGTAAAGCT GGGTTACAAA CTATTTGACT CTAGAGCTTT
10261 TAACCACTGC CTAAGACTGC CCCTCATCAA TAGAGGCTTG GCAACCCAT GGCCCTAGGC
10321 AGACCTGGGG GCAGGAGGGC TGCATAGGAA AGGGCAGAAC TTTCTAGTTC TAGAACAAAC
10381 AATAAAAAGA AGAAAGCCTT CAGAGGCTCC ACATTAATTG GAACAAAGGG GATTATGACA
10441 GATGCTTAGG CATGTTTGTT GAATTATTAA TAAATAAAAT CAGACTAGGG ACTGGGGACT
10501 CCAGTCTTGG AGGCCTTCAC AGGCCCAGAT CCCAAACCCA CCAAACCCAC TAGACCTGCA
10561 GTGGAAGCTA CAATGAGCTT GGATAGTTCC TGCAGTTAAC AGCAATATAC TATGTATTCT
10621 GCCTCTTTCT ATTTAAATTT TTTAACCTGA TATCTTAGTA AAACTTTTTC ATAAAAATTC
10681 CAGACATTTG GAAGTGCCAA AAATCAAGTC ATTTTTTATA TCTTCAGTAA TTCTGTGCCA
10741 TAAACAAACA GGTTGCTAGG TGCTCTATGG GATGTAAAAC CTTGGCCAGG CAAGGTGACT
```

FIG. 4 CONT'D

```
10801 CACTCCTGTA ATCCTAGCAC TTTGGGAGGC TGAGGCGGGA ATATTGCTTG AGCCCAGGAA
10861 TTTGTGACCA GTCTGGGCAA CATAGTGAGA CCTAGACTCT ACAAAAAAAA TTTAAAAATT
10921 AGGTGGGTGT GGTGGCTCAT ACCTGTAGTC CCAGCTACTT GGAAGGCTGA GGTGGGAGGA
10981 TCGCTTGAGC CCAGGAGGCG GGCAAGGCTG CAGTGAGCTG TGATGGTGGC ACTGCACTCC
11041 AGCCTGGGCG ACAGAGCAAA ACCCTGTCTC AAAAAAAGAG GCAAAAACAA AAACTTAAGA
11101 ATCCTTGTTC TAGATTGGGG CAGACTAAAG AGTCAGTTGC CATGGATGAA GCTTGATTGG
11161 ATCCTGGAAA AGGAAAAATA AAGCTTCAAA GGACATGTTT AGAAGTTTAT AAAGGACATG
11221 TAGAGAAATC TGAGAGTGGA TCGCTGTTGG ATGAGTGATG TTGATTTTCT TAGGTGTGGT
11281 GATGGAGTTA TGATTGTGTA AGAGAATGTT CCAGTTCTTG GGAGAGGCAT GCTGACATTT
11341 TAGGGTAAAA TGTCATGATA TCTATAACCT ACTTTAGGAT GGTAGGGTAG CAAGGATTTG
11401 TGTAAATGTG TATATGCATG TATTTATATG CACACATATG TGTGTGTGTC AGAGCACACA
11461 GATAGTGCAA GGTGTTAACA TTATCAGTTG GTGCATTTAG ATGAGGAACA TACAGTATAC
11521 AGATGTTAAT TGTATCTTTT TTCAACTTTT CTGTAAGTTA AAAAAACTTT CAAAATAATA
11581 AGCTATATTG AATTTTTAAA ACATCATATT ATGCTATTCT TCTGTATAAA TTCTCCAATG
11641 GTGTTCCATT TCACTCCTTA CCACAGCCTA CAAGGCCCAT CATGATCTGC CCCGACCTAC
11701 TCTCTGATCC TCTCTCTTCC TGCTCAAGTG ATTCTGGCCA CCCTTTTTTT TTCTTCTTTT
11761 TTAGACAGTC TTGCTCTGTC ACCCAAGCTG GAGTGCAGTG GTGCGATCTT GGCTCACTGC
11821 AACCTCCACC TCCCGGGTTC AAGCGATTCT CCTGTCTCAA CCTCTAGAGT AGCTGGGATT
11881 ACAGGCATGC GCCACCATGC CCAGCTAATT TTTGCTCACC CTGGCTTTTT AATGTCTCTG
11941 GAATATGCTG CCACTCATTC CTGCCTCAGG GTCTACTTCT TTGCATCACA GCAGATGCCA
12001 TTATCTGACA TCACACTATA TATTTATTTG CTTGTGTAGT TGGTCCCCTT CTCCACCCTA
12061 CAGTAGAATG TAAGTCCAGT GAAAATGAAG ACTTTGTTCA CTGTTATGTC CCAGTACCTA
12121 GAACAGTTCC AGGCACTAAG TAGACACTCA ATAAATGTTG ACTAGTGAAA AAAATGTGA
12181 GACCTGGGAT CCTGCCTTAT AAGGACTCAG TGTCTAGAAA AGGGAGCTGT TTTCCATGCA
12241 AATAACTGTA GTACAAGAC GAGTGTAGGC AAATTGCTAT GGGGCTTCAA AGAAAGGAGA
12301 GGCAATCCGG GGCTTGGGGA ATCAGGGAGG GCTTTGAGCT GATCTCCCAG GTTGGCAGAG
12361 TTGAGTCAAG AGAGCATCGA GAGCTAAGGC ACACAGTGAT CATGCATGGG CTGGGTAGGG
12421 GCATGGGAAA GAGTCCTGTC CGGGTGGTGT GCCCAGGGAA TGCAGGGGTC CTGCGACATG
12481 AGGCTGGGCT CTTAAGTGTC AGGGAGGAAA CCCAGGAGAG AAAAGCACTT CCAGTGAAAC
12541 CCTGGGAAAG GCCAGAGAGA AGGAGGAAGA GCATGGGATC TTGGACAGAG GCTGGAGCAA
12601 ATTGTAACTG ACCTCCGCTG ATTGGATTTT TGACCGTGGT TAGGACCCTG ACTATTGCTC
12661 ATTCAGACAT GAGACACATT TGCTTACAGC CTCTCTTTGT TGTTCGAGGG TCTGGATCCC
12721 TCAGCTTAAG AGAGGAATGG GGGCTCTGAA GCTCTGGGCC TCTTCATTGT CTCCCTGAAT
12781 TCATTTGCTC TTTCTCCTTT GCTCCTTTAT TTGCTCCTTC TTCCTTTGAA TGGAGGCTGA
12841 CATGTTTGGA CTTGACTGAT TTGAGAGGAG GGGAAATTTG GTACCTAGCC AACAGCTGAC
12901 ACAGACAGTG GCTGCCACCT GTAGGCAATT GTGAACAGAA GGAATAGAAA GCTACAGGAG
12961 CAAAACTTTG AGACCAGCTT TCATATTGGT TCCTCTTACC TCACTGCCCT GGGTAGCAGG
13021 TCTTTGGTTG GAACTAATCG TTCTCTCCCT CCAGTCTCCT ATTCATGCTC TTACCTCCCG
13081 GCCTCAAGCC TGCACCTCTT GCTGAAAAAG ATCCAAGAGG TGACTCCCTT CCATCTCTTC
```

FIG. 4 CONT'D

```
13141 AGCTCCACCC CTTGCTTCTC ACTGTGGGTT AACTTCCTCC TTTGAAGTGG CAGGATCTGG
13201 GTGCCAGTTT GCCTGTCAGG AAGTGTTTCT TATCACTCCA CTCCCAATCC CCCTGGTCCC
13261 AAACTAGGTA CAGAAATTCC TACTGGGGCT GAAGAACAAT TGCCATCCA CAAACGTCTT
13321 AGACAAGACA TGGCCAGCCG CCCCCTACAA GTGCCTCAGC ACAGCAAATC AGGAGCTGCA
13381 GCAGCTCTTC TACCAGTGGA AGGCAAGTGG AGCCCAGGCA CCCCTCCTCT CATTTCGTCT
13441 TTTTTTTCCC TCCCCCTGAT TTTCCTCTTT TGCCTCCCTC TTCTATTTTT TTCCCATTAA
13501 AAAAATTGTG GTAAAATATA CATAACATAC AATCTACCAT TTTAACGGTG TTTAAGTGTA
13561 TAGTTCAGTG GCATGAGCGA CATTCATGTT GTTCTGCAGC CATCACTGCC ATCCATCTCC
13621 ATATGCGTTT TTCATCACCC CAAACTGAAA CTCTGTACCC ATTAAGCAAT AACCCCCTAT
13681 TCTCCCATTC CCCTAGCCCC TGATATCTTA TAATCTACTT TCTGTTTCTA TGAATTTCAC
13741 TTTTCCAAGT GCCTCATATA AGTGGGAATC ATATTTGTCC TTTTGTGTCT GGCTTATTTC
13801 ACTTAGCATA AAGTAATTTG TTCTTTTATT CAGGAAATGC TTATTGAGCA CCTGTCTGGG
13861 ACTAAGCCTT GCCCTGAGAG CTGAGCATAG AGCCCTCCTG GTGCTTTTAT TTGATGGTGT
13921 CCATTCCCTC CCCTAGCCTC CCTCAGTTCT CGCACTCCTC CTCAATGGTC CTCCAGCCCC
13981 GGCCTCTCCC TGAGGTGTCT AGTGCCTGTC CTTTTCCTC AGTCTCTCTC CTCTCCTAGT
14041 GTCTTCTAGT CAATATTTCT CACCTCCCTC CCCAGCCCTG CCCTCCCACT CTATGATTTT
14101 AGCTCCTGTC CCTCCTTCCT CACAGTGCAA GAGGTTCCGG GATCAGCTGT CCCCGAAGCA
14161 GGTAGAGATC CTGAGGGAAA AGCTCTGTGC CAGTGAACTG TTCAAGGGCA AGAAGGCTTC
14221 ATATCCCCAG AGGTGAGGGC CTCCCAGACC CTGCACAGCC AGTTCCATCA CGCAGCAGTT
14281 CTCAAACTTG AGCGTGCCTT AGAATCACCT GGCAGGATTG TCACCCCCAG GTGCTGTGTC
14341 CCTCCTCAGA GTCTCTGATC CAGCAGGTCT TGGGGTGAGG ACCAAAATTT GCCTTTCTAA
14401 CAACTCCCCA GGTGGTGCTG ATGTCTTGGT CCTGGACTGT GCTCTGTGGA CACTGACAGA
14461 GGATACGTGG ATGTGGGGGA AGGGCCCGGG AGGACTAGGA TGGGAACTCT GGGGGTGGGG
14521 AAGAGGCCTC TGGGCCTTGT CGCGCTGCAC ACCTCCCATG TGTTCTCAGT GTCCCCATTC
14581 CATTCTGTGG TGACTACATT GGGCTGCAAG GAACCCCAA GCTGCAGAAG CTGAAAGGCG
14641 GGGAGGAGGG GCCTGTTCTG ATGGCAGAGG CCGTGAAGAA GGTCAATCGT GGCAATGGCA
14701 AGGTAAGGGC CTGCAGGCTG AACTCCTCCC GCAGCTAGTG CAGAGCTGTG GGCTGGCATC
14761 TGGAGAGCAG ATGGCAGGCT GTGTTTGCGC CCTGCCAGGT GGAGTGGGGG CAATTAATCC
14821 TGCCTTTCCT CACCCTTGCC TGTTCCGTCC CTAGACTTCT TCTCGGATTC TCCTCCTGAC
14881 CAAGGGCCAT GTGATTCTCA CAGACACCAA GAAGTCCCAG GCCAAAATTG TCATTGGGCT
14941 AGACAATGTG GCTGGGGTGT CAGTCACCAG CCTCAAGGAT GGGCTCTTTA GCTTGCATCT
15001 GAGTGAGGTA TCAGAGCTGG GTGGGGCAAG CCTTGGACTG GAGAAGGTGG TATGCATCCC
15061 AGGGCTGGGG CAGGCTGGAG GTGATGGGGA CCAGACCTTT CGCTCTGGGC CTTTGATGTC
15121 CCTCAGGTGC TCCTGAAGAG AAAAAATGAA TCCCTTTCCT GCTATTTTC CCTCTTCCTA
15181 AGATGTCATC GGTGGGCTCC AAGGGGACT TCCTGCTGGT CAGCGAGCAT GTGATTGAAC
15241 TGCTGACCAA AATGTACCGG GCTGTGCTGG ATGCCACGCA GAGGCAGCTT ACAGTCACCG
15301 TGACTGAGAA GTGAGGCCAT GAACTGGGGG TGAGGGCGG CTTACGGTAG ATGGCCAGGC
15361 TGATGGTCAT CGTGACCAGG ATCAGAAAGC GAAGCATGTA GGGCAGTGCA GGCCGGGGCT
```

FIG. 4CONT'D

```
15421 TGGAGGTGTT TCTCAGGCCC CCACCCAGGT TCTCTGGGGC CTCAAGTCCT CTGACTCGCA
15481 TGATGGGGGG GCCATCATGG AAATGCGGGA GTCGGGGTGA GGGGATGGGC ACTAGACTTG
15541 GTTTTCTGTT CCCTCTCCAG GTTCTCAGTG AGGTTCAAGG AGAACAGTGT GGCTGTCAAG
15601 GTCGTCCAGG GCCCTGCAGG TGGTGACAAC AGCAAGCTAC GCTACAAAAA AAAGGGGAGT
15661 CATTGCTTGG AGGTGACTGT GCAGTGAGGA GGGGGCACCA TGCAGAGATG GCAGTTGCTT
15721 CCTCCTGAAC CAGCACTAAT CCCCCTCTGC CCTCCTGTGT GGGAGGATCT CTAACCCCTC
15781 TGATCGTGGC GCATGGCTTG GGGATTAAAC TACCCTTGAA GAGGACCCTT GTCCCAAACC
15841 CTTCTTGTTC TCTCCTCCAA AAGTAGCTTC CTCCAACCCG CAGCCTCTCT GCACACTAAT
15901 AAAACATGTG GCTTGGAAAG GTTCAGTCAG GGTGGGTGGG TCCTTGTTCC CCCTATCTTT
15961 TCACCCAGGT GTACTTAGAC CCCTGCCCCC ATGCCCTTTT TCCTCCTCAA GCTCCTTGGA
16021 GCCAGCTAGT GAGGTAATAA GAAAGGAAAA GAAGGAAAAT TGTCTCCGGG CTCCTTGACC
16081 GGCTGAGCTC TGGGGGGGTG TTTAGAGAGA CTGCGGTGGG TGGAGGGGCT GCGGGGGGAG
16141 TTAAGGATGG GGCTCAGGTC GCAGGTGGCC AGTGGACTGA TTCATTAAGT GTGTCCCTGG
16201 AGGAAAGAAG TGAGCATCCC TGTCTTGGCA GAAACTGGGG TCCTTTGGCG ATTTAGCCTG
16261 AAAAGCAGCC CAAGGCTGGA GGGCTTATGT ATGCTGGGGT GCTGGGGAAT GCAGGGTCTC
16321 CTGTACTTGG GAACGCCATC ACCCCTTCTA CTCCCACACA CAGCACAGGG CTCCATCACA
16381 CCAGCCTCCC CGACACCCCC TTCCTTCTCA CACACCCGAG ATGCCAAACT GCTGCCAACA
16441 GTTATCTTGC TCGTCTCTGT CCCACAGCTG GGGCCTGCAG CAGGTGGCAC TTCACATCAC
16501 TCACTTGATG AGGCTCCCTC ATCAAGACCC TCCCATCCCT GTAACCTGGC CCTTTCCTCT
16561 CCTCTTCCTT TATTTTTCCT GCGTCATTGT CATTATCTTT TTCTCACCCT CCCAACTATC
16621 TCACACCATC TCATTGTCCC TGTTTCTGTG AGCTCTGACT AATATCAATA TGTAATATTT
16681 TGTAAAATGC TTTAAATATT TTCCTACTCC CCTCATATC TATTTTCTCA TAGATTCTGT
16741 CTTGTCTGTC TTGTCTCTAC CTTCTGTCTG GCCTCTACCT TGGGGAACA AGCTGCTCAT
16801 GTAGTCACAG TAAAATTTAG ATCTGTGGTC TGTGAGAGCT TAGCAGGGTC TGCCTTTGTT
16861 TTTGTCTCTG GCTGTCTCTT CCTCTTCTCA AGATCTCTAC CTTGCCTACC TCTTCCCGCT
16921 TCCTTCCCTT AACTCACTAT GCCTTGGGGC TGGGGTCTCC CTCCACCTGA CTTCCATCTG
16981 CAGGCAGCTC ACGGCCGGCT ATCATGCTGG CCAGGGAGAA CTGATTAACT TCTCTTCCTG
17041 CCTGCAGATT AATCTGCTGT CTGAGCACAA GCCACGTGCT TCTGGCACAC CCTGCTTTGA
17101 GCTGAGATAG AACCTGGGGA ATCATCTGTT TTCAGGCGGG TGAGGGCTA GAGCCTGCCT
17161 TGTTTGGGAG GAGGGTGGCT CTGTTCAGAA TAGGGGTAGC TCAGGCTCTG GCCAGCCTTC
17221 TCCCGCCCCC AACAGCTCCC CCCATCCTTG ACTTCTCAGA ATCAGGCCGA GAAGAGCCTA
17281 TCTGGCCGAG AGTGGGGTGG TGACCTGCGC CTCATCGCCC CCGCTCTCCA TCTCATCTCC
17341 TGCTCCCAGG GCCCAAATTG TCGTCACTTT CCCAGTGAAG TGTCTGGTCA TTTTCAGAAG
17401 CAATTTCAGG AGAACATGCA GCTGCCGCTC CCTATCCTGC ATTTCCCTTC ACAGGGCTGA
17461 AGGCACTGTC AGCTCCCTGG GCTGGGGGTG ATGGGAGAGG GGAAGGGCTA GGGCCCTCAC
17521 CCCTGTCCTC ACTGTGCCCA TCATGTAGAT GGACTGGAGT TCAAGGAAGG GCAGGCACTC
17581 CCCTCCTCCT TTACTCTTCT GTCACTCTCT TCCTCCTCTT CTTTCCTGTC TCTGCCTCTC
17641 TTTTCTGGAG CCTAGGAGTG TGTGTTTTCA TCCCCTGAAA CAAATAGGGA CTCAGTTTCC
17701 CCACCTGTGT TACAGGGTTG GAATTGGCTC CATCACTGTG GGAGAAGCTG GAGTTCTGCT
```

```
17761 ACCAGTCCTC CCCTCCCCAG CCCTGCCTCT TCTCTCCCAG CCCTCTCCCT TCAGCCAGTT
17821 CAGCGCTCTG AGAGTCTGGG TTGTTTCAGC CTCTGAGGGG CACAAGCCAT CCTGGATTCC
17881 CCTAACCCCA TGAGGAGCCA TTCTAGCATC TCACAGCTTA AACCAGCTCT AGCTCAGTCC
17941 TCCTGGCTTA GTCCATTTTT CTTCCTCAGG CTCTGAGGGC CTCTTGTTCC TTGCTCTGTG
18001 GGGTTTTCTC CAGTTGTCTC CTGGCTGCAG GACATGGCAG GACATAGAAT GCTGTCATCC
18061 TTCCACTCTT CATTGGCATC TCCACCCAGT GTCACATATG ACCCTAGCCC TGCTCTCCCC
18121 TTGCCAGTAC CCCTCTGGGA TTTTGCGAGA GTCCACAAGT TGTGCATGTG GTGGATATAT
18181 TCAGGCCATC TTGTGTGTAC AAGCTAGAGG GTCTGCTTCC ACCTCTGGCC CTCAGTGAAT
18241 TGCTGACTAA CCTGTCTCAA CACAGCACAA CTGTACACAC CTTTTCCTGG CCTCATCCCT
18301 AACCCATCAT AGCAGCAAAG AGGGGAAGTT GCAGGGAGG AGCTGCTAAG GACCCTGGAC
18361 TCCAAGTACC CTGCTCCTCT AGGCCAGGGA CATCATCTGA GATGTGGCTC AAATAAAGGG
18421 TGGGTGTTCA AGAAAAAACA CTTGGGGACT CTATAGCTGC AACACCCACT TTACATGTCA
18481 TTTCCATATG ATTTGTAGGC AAAATGAAGC CCAGGCTGTC CTAGCCCTCC AATACCTCCC
18541 TCTCTCATCA CCTCTCCAAC ATAGCCTAGC ATTAGCTCTT TCAAGTCTTT GCTAATCCCA
18601 GAGATCAAGG GGTGATCAAC TCTCCCTGCC ATCCCCTTGT TCCCCGCACC CCCCGCCCCG
18661 GCTCCCCCAC CATCCTTGGC TCCTGCCATC CTCTTTGAGA TGCTGCATCA TCAAAGGACA
18721 TTATTTATGG TGTACCTTTG CTGAAGCCCT GCTTCCCTGG TGCCAGGGCT TGGGAGCAGG
18781 GATGGGTGGG TTGGTGGGGG AGAGGGTGG ATGCAGAGAT TGGACCCAGG AGGCTTTTAG
18841 TCCTCAGCTC TTGGCTTAAC ACCTCCTCCT CTTACACACC CAACTCCCTC CAGCCTGCCC
18901 AGCTTGGGCC TTCAGCTCCA GATTGGTGGG GTTAGGAGAG GAGGAGGAGG GAGATGGATG
18961 GAACCAATTA GGAACAGCAC CTGGGCTCCT CACAGGAATG AACCAGTCAT GCCATTTGCA
19021 TGTAAACAGC TTCCCACTTC TCTCCTCATC CTACCAAATG CTCCCAACCC TGGGTTCTGG
19081 CCCATGTTCT TTGCCCACAC AGCCCTGTAA TTAGCTGGGT AATGAGAAGC TTTTAATGAG
19141 TCCCATTAGC ATCTCGTGTA ATAAAGAGGC CTTGAGACCC AGCTGCTGTC CTCACTTTGG
19201 GATGAACACG GGTCCCTGTG TAGCCAGTGA CTTCTGTCAG TACAGTCTAA GTTCTCGGAT
19261 GGGGTGGGAG ACAAACATTT CAGGACCCCA GCAGCACTTG AGAGGTTCCA TCGTGGATCC
19321 ATGTTTTTGA CTGTGATACA AGAAACTTGG CTCTGGCTTC CTTGTTCATT TTGTAAATAA
19381 CATTTTTTCT TCTTTTAAGA GACAGAGTCT TACTTGTTG CCCAGGCTGG AGTGTAGCAA
19441 TGCAATTATA GCTCACTGCA GCCTCAACCT CCTGGGCTCA AGTGATCCTC CTGCCTCAGC
19501 CTCTGGGATA GCTGGGGCCA CAGGCATGCA CCACCATGCC TGGCTAATTT TTAAAAATGT
19561 TTTTGTAGAG ATGGGGTCTT ACTTGCTATG TTGCTCAGAC TGGTCTCGAA CTTCTGGCTT
19621 CAAGCAATTC TCCCACCTCG CCCTCCTAAA GTGCTGGGAG TATGGGCATG AGCCACCATG
19681 TCCAGCCTTG TAAATACATT TTATTGAGC ACCTATTATA TGTCAAACAT TATAAAGTGA
19741 GGGATACAGT AGCAAACAAA ACAGACAAAA ATTTTTGCCA TCATGACACT TATATTCCTG
19801 GGTGGGAGTG GTGATAGAAA GACAATAAGT AAAATACTTA GCATAGTGGA TGTAATAAGT
19861 TCATGAAGGG AAAAATGGGA GTGAGGTATA TGGAATTTTG GGGTGGTGAT AATTTTAAAT
19921 AGGGTGATTG GGGAATGCTT TGTTGCACAG ATTGTTTTTG TAGTAAATAT GAGATAAAGA
19981 TACGGTTCTC TCCCAAACTC AAAATGTAGA AGAGTAGAAG GTCCCAAATC TTCAAGTCTC
```

FIG. 4 CONT'D

```
20041 TTGGAGAGGG GGGCCACCCA TTCCGTCTGG GACAGTTAAC TGTTCCCTCA CAGGTCAAAG
20101 TTTATGCCAG TGCAGTAAAA AGAGTGGGAG ACCTGGGGTG AGACAAACCT GGATTTGAGG
20161 CTGTTCTTCA CTGATTAGTA GCCATATGTA CTGGAGCAAG TGACTGAACC TTCTGAGCCT
20221 GTTTTCTCAT CTGGAAAATC AGAATATTTC CTACTTACAT GGTCATGGTG ATGAAAACCA
20281 GATGGACTGC TCCATGCCAA AGCACCCTGC AAACATTCAA ACCCTGCACC CATTACAAAT
20341 ACTGGGCTGA CGGATGGCTC TGGCTTTGCT TTTGCATCTC CGCTGTCTCA TTCAGCAGCA
20401 GCATCTGGCT CTGGCTCTCG GCTCTGATCC TGGTTCTGAC TCTCCCCTGG AGCTCTCTCC
20461 CTTGGGTGAG AAATAAGCAG ATAATCTCCC TCATCTGTGT GTGGTGTGAA CAAGAGGCTT
20521 GAAAGGTCAG AGAAGAAGAT GCCTGAACTG CAGGGAGACA GATTAGAGTG GGGAAAATGT
20581 AACTCTGAGG AAAAAGGGAA GCAATTAAGA GATCAAGGCC AGGGGCAGTG GCTCATGCCT
20641 GTAATCCCAA CACTTTGGGA GGCTGAGGCG GGCAGACCAT GAGGTCAGGA GTTCGAGACC
20701 AGTCTGGCCA ACATAGTGAA ACCCCGTCTC TACTAAAAAT ACAAAAAAAT TAGCCAGGTA
20761 TGGTGGTGTG CACCTGTAAT CCCAGCTACT GGGAGGCTG AGGCAGAAGA ATTGCATGAA
20821 CCCGGGAGGC AGAGGTTGCG GTGAGCCGAG ATTGAACCAT TGCACTCCAA CCTGGGCAAC
20881 AGTGTGAGAC TCTGTCTCCA AAAAAAAAAA AAAAAAAAAA AATCAAGGCC GGGGAGGGGG
20941 CAGGGGTGGC ACAGCTATCG AGTTCTGTTC ATCCTCTGTG AGATTACATC AGGAGGTGTA
21001 AAAGAACTCT AGAAGAATGA AGCTAAGTCC AGCTGATTCA GGGTTCAAGA AGGATTGAGG
21061 TGGGAGAGGC ATCATGACCA CTGGTGAGGA GTGGAGGAAG GCCGACACTG GAGCTTTCTT
21121 TGCCCAAGCA GAGGAGGGGT GTGACACTCT TGAGGACCAA TGTAATGGCG CAGCTCCCTC
21181 TGGGAGGGGG AAAGGAGAGG ACTGGAGGGG ATGCTAAACT GACCTTCTAA CCTTCAGGGG
21241 CCTGAGTCTG GTTGTCCTGG GTGGGGAGGG GCGCCTGCCT GAAACTGTTT TAGCCCAGAA
21301 GTCAGGCCTG AAGGTTAAAG GGCAAGGAGC TGGTGGATGA ACAAGGTGGG GAAAGAGGCC
21361 CAGGGTCCAC ATCTACTGAG CTGGACTCAG GCATGGGAAT TGGTGTTGTG AGGGCCAAGA
21421 CACTTGGCCT CCTAAAAGTT TGCTGAAAAT CACTGACATG AGAGTAATTG ATTTATAGGA
21481 GAAAAGGTAG ATAAATTTAT TTAATATGTA TATATGAGCA CCTTTAGAAT GAAGACCCAA
21541 AGATATAGGG GAAATTGCCA GTTATTTATT TATTTTTTTT GGAGATGGAG TCTCACTGTG
21601 TCTGCCAGGC TAGAGTGCAG TGGCAATGAT CTCGGCTCAC TGCAACCTCC GCCTGCTGGG
21661 TTCAAGCAAT TCTCCTGCCT CATCCTCCTG AGCAGCTGTG ACTACAGGCA CGCACCACCA
21721 TGCCCGGCTA ATTTTTTGTA TTTTTTAGTA GAGACAGGGT TTCACCATGC TGGCCAGGCT
21781 GGTCTGGAAC TCCTGACCTT GTGATCCGCC CGCCTTGGCC TCCCAGAGTG CTGGGATTAT
21841 AGGCGTGAGC CACCGCCCCC AGCCTGAAAT CGCCAATTTT ATGTTTATGT TTTACAAAGT
21901 ATGGACAGCT GTGTAGAAAT ATGACTGGAC AGAAGGGCAT GCTCTAATGT TAACAGACTG
21961 AGTGGGGAAA CCCAGGAAGG CCTGTTGAGA TTCCTCCTGG CCTCTCTCAT TCCTTCCTTC
22021 TGGGTATGGG GCAGGACCCT CTCTGGAATG GGGAGATCTT AGGACCTAAG TTAAATAAGG
22081 TAGGTCAGAT AATTTTTTAT GGCCAGTTTT TACATACAGT AATTTTAGGT TTTATGGCTG
22141 GCTTTGGGGA AAAGAGGTCC TGGTTTTTAT AGCTGGCCTT GGGGGAGAAT GGGACCCAGC
22201 AACAGGAGGA CAGGAGAGGG TCAGAGAAAA ACTTCTGCTT CTGAGGCTGC TACTGAGGCC
22261 TTCATTTTAG GGTATTGTCT TCTGAGCCCC AGCATTCCTC GGTGTGAAAA ATTTAAAGA
22321 AATTTATAG TCCAGAAATT GAGTTGGTCA ATTGTCTTAT AAGCCATGGA ACTAGTCTCT
```

FIG. 4 CONT'D

```
22381 TAGTCCTGAG AATAGGCCAG TCTAGTTAAA TAGTTATTAG TTGTGTCTAA TTTTAGGCAG
22441 TGTGTTGCAG ATGGGCTTCC ACCAAAGCCA GGCCTCTATA TGATATGAGT AATCAGTTAT
22501 TTAGTAAGAG GCATTTTTGT CTCAAAAAAT AAATAAATAA AAATATATGA ATAAATGAAT
22561 GTATGTTTCT TATCAGACTA CGTCTGTTCT ATCATTAATT CCAGAAGGGA GGAGGGTCTG
22621 GTTCCCCCTT CCCATCATGG CCTGACCTAG TTTTCAGGTT AATTTTAGAA CACCCTTGGC
22681 TGTGAGGAGT GGTCCATTCG GATGGTTAGG GAGCTTTAGG ATTTTACTTT TGGTTTACAA
22741 AGTAATGTGA ATTAAACAGA CATTTGAGTT AAAGTTTTTA TTTTTTAATA AAATATTTGA
22801 TTTAAGCATT TTTTTAACTG AATTAATTAG AGCTCTTTTA TATATTTTGA TAATGGAACA
22861 TTACATACAC AGGCACATAT AAATATATAG ACACATAAAC AGAAGTAGAG CTTATAGATT
22921 TATACTTTTT TTTTTTTTTT TTTTTTTAA TGAGACAGGT TCTCCTTCTG TCATCTAGGC
22981 TGGAGTGCAG TGGTGCCATC ACAGCTCACT GCAGCCTTGA CCTCCAAGGC TCAAGCAATC
23041 CTTCTACCTG ACTGGCTAGC TGGGACTACA GGCGCGTGCC ACCATGCCTG GCTAATTCGT
23101 GTATTTTTTG TAGATATGGG GAGTTTTACC ATCTTGCCCA GGCTGGTCTT GAACTCCTGG
23161 GCTCAAGAAA TTTTCCTAAC TTGACCTCCC AAAGTGTTGG AATTACAGGC ATGAGGCACT
23221 ACGCCAGACC AGATTTTTTA TTTGTCAGTT TCTAGGTAGT TTTCCCCAAC TTCAGACTAT
23281 CAATTTTTAA ATTATCTGTT TTATGTCTTA ATTATTAACT AGGCAACTCT AAACTTGTAT
23341 CTCTAAGACA TGACTTTTAG ATGAAATAAG GTAGAAAATG TATATTTCAA AGGCATAGAA
23401 TTTAGATCTA AATAAAGGTA AAGTTATCTA AATTTTAAGC CATTGTCTTT TCTATTCTAA
23461 AAGGTTTTGG AGGTTTGGGT GTAGAGAGGG AGATGCCTTT ACAAATGGAA TTTTTGTTGT
23521 TGTTTTTGTT TTGAGACGGA GTCTTGCTCT GTCACCCAGA GTCTCGCTCT GTCGCCCAGG
23581 CTGGAGTGCA GTGGCACGAT CTCCGCTCAC TGCAACCTCT GCCTCCCGGC TTCAAGTGAT
23641 TCTCCCACCT CAACCTCCTG AGTAGTGGGG ATTACAGCTG TGTGCCACCA CGCCCAGCTA
23701 ATTTTGTAT TTTTAGTAGA GACCGAGTTT CACCATGCTG GCCAGGCTGA TCTCGAACTC
23761 CCAACCTCAG GTGATCCGCT CGCCTTGGCC TCCCAAAGTG CTGGGATAAC AGGCATGAGC
23821 CACTGCACCT GGCCTTTTCT GAGTTTTTA AGGAGTCTGA GTCATTAGAA GTCTTTTCTA
23881 GATTTTTAA AAATGTGGTA TTGAAGATGG CAAAGAGGAA GGAGGAATAG GGTGGAGTAA
23941 AAGTAAATGG GAGGATAGTT TTTAAGAAAG GAAGTGAATA GAGACATCAA ACACATTTTA
24001 AAAAAAGAT TTTAGTCTAC TGAACAAAAT TTTTTAAAAT AGGATTTAAA GAGAAAACAC
24061 AGAAGGCTTT AAAAATATAC ACATAGCTTG AATATTAGCT TTTAATTAAG CTGACTTCTA
24121 ACCATGGAGC TCTTTAACAA AAATTCTTTT AAATTTGTCT CTCTCCTCCT TTAAAACTTT
24181 TTGTAGAGAT GGGGTTTCGC CCTGTTACCC AGGCTGGTCT CAAGTCCGGG CAACTTCTGG
24241 GCTAAAGTGA TCTGCCTGTC TCGGCCTCCC AAGTGATAGG ATTACAGGTG TGAGCCACTG
24301 CGACTCACCT TAAATCTCTT GTTACCAGAT TTAGTTGGG ACAAATGCTG ATATTTAAA
24361 AGTCACATAA ATATTAAGCC GAAAAGGACT GATTTCTGAT TAGGAAGGAA ACCCTAAGCC
24421 ACGGTGGGAA TTTAATTAT TAAACTGTAA AATGGAGCAG CCTCCATTGT TAATTTTGTA
24481 TGGAATCCAA AGTGGCAGTT TGAGTGTAAT TGTTTTAGGT CAGGTTTTTG TGCTTTAATT
24541 TAATCAAGAC AATTGTTAAG GATAGCTGTG ACACTATTAT GTGTCCTTTT AATTTGATCT
24601 ATCAATTCTT TAGAACAAGT AATTTTTTTA AATTTAGGAA TTTTAGTCTA AAGGATTTAT
```

FIG. 4 CONT'D

```
24661 CTTTTGGCCA TTGACAATTA GAATTTTTAA TGGGGTATTT AATTCCAATA GCAACTTAAT
24721 CCAAAGTTTT CTTTATGTCA AAGAAAACAG AAGCCCAGGA GGGATGAGAC CTTGTAAGAC
24781 AAAACTCCCC TAGGAGCTTG GAATGTTTGA AAATACATGT GTTGGGCTCC CAATCTTTTC
24841 ATACTGGCTG TGATGTTACC TGAAAAATCA CATCCTTTGG ATGGTGGAGA CCAAGCGGGA
24901 ATATCCCCAT CTAGTCACGT CATGCTCTCA AGGACATGAG ACAAGAGGGA AACCTCTCAC
24961 CCTGTTTTTA TTTCAGGGAC TGGCAGCAAA GTTTGTCATA ACAGAAGTCA GCATAACCAG
25021 AACCACGAAA CTGACCAGTT TGCAGGGCCA GTTCAAACAG TGGGTTGCAG GCCTGTTCTA
25081 CCCTAGGGTA CCCCTCCTTA TGACAGAACA CCAAAAGACA AGACAAAAAC GAAGGAAAAC
25141 GGCAACAACA AAAAAGCTAT TTCTGAAAGG AAAATGGCAA CAACAACAAC AAAAGCTATT
25201 TCTGAAGGGA ATGGGGTCAA ACTATGAATA CTTATACCAC AAAGTACTAA AAAATATATC
25261 AGACTCACTA TACCAAGGTT AGTCACACAC AAAACCTGTT CTCTCATTAA TCTTACATTT
25321 GGAAAGGAAA AGGGAAACAA TGATTTTTAC TGTCCACTCA TCCAGAGTCC ACAGAGAGAG
25381 GAAAACTGGA AAACTGGGAG TCTGGCAGGA AATTCTCACT CCTCTGCTGG CTTGCCAGGT
25441 TCCTGTATTT CCTTCTCTGT GGCTTCCAGA AAAGCACAAT AGCTTTGGTG GTCTTATTTG
25501 TGATGCCAAA CTGTGGTCTT GGCCCCCTAA AGTTTCAGTG AAAATCACTG ACATGAAGCA
25561 GATTAATAGG GAAAAAGGCA TACAAATTTA TTAAATACGA ATGGGAGCCT TTAGAATGAA
25621 GCCTTGAAGC TATAGGGGAA ATTGTCTATT TTTATGTTTA GGTTTAACAA AGTATGGACA
25681 GCTGTGTAGA AATATGACTG GACAGAAAGG GCACGATCTA ATGTTAACAG ACTGAGTGGG
25741 GAAACCCAGC AAGGCCTGTC TGTTGAGATT CCTCCTAGCC TCTCTCATTC CTTCCTTCTG
25801 GTGTGGGGCA GGACCCTCTC TGGAATGGAG GTTTTATGAC CTAAGTCAAA TAACGTAGGT
25861 CAGATTTTTT TTTTTTTTT TTTTTTTTT GAGCTGGAGT CTCTCTGTCA ACAGGCTGGA
25921 GTGCAGTGGC GTGACCTTGG CTCACTGAAA CCTCCGCCCC CTGGGTTCAA GCCATTCTCC
25981 TGCCTTAGCC TCCTGAGTAG CTGGGATTAC AGGGGTGTGC CACCACGCCC AGCTAATTTT
26041 TGTATTTTTA GTACAGACAG GGTTTCACCT TGTTGGTCAG GCTGGTCTCA AATTCCTGAC
26101 CTTGTGATCC ACCTGCCTCG GCCTCCCAAA GTGCTAGGAT TACAGGCGTG AGCCACTGTG
26161 CCCGGCCTTT TTTTTTTTT TTTTTTTTA GGAAGTTGTA TTTTGGGCTT TTTAACTAGC
26221 TTGTTTTTA ATTAGATTAT TGCCTTTAGG GTGGAGCCCT TTAATAAAAA GGGGGAAGAA
26281 AACATAGGTT TTAGGGCCTC ATATTTAAAT GGGTAAAGCA GGCATAGCTG GAAGGCAGAA
26341 TACAGAACCC CCCTAATCAA GGATCTCATT TTTATATTGA ATCCTAGGCC CCCCAAAAGA
26401 GGGAAATGTC ATGGGACGAG ATGTGTGGCA TTTTTATCGA GTGCCCCACT GTAAAGATGC
26461 TCCCCCAAGG CTGGCAGGCA GCCCAGTGCC GATTAGCCCA CTCTGTGCTT AGTCTTTTTT
26521 TTTTTTTTTT TTTTGAGGTG GAGTCTTGCT CTGTTGCCCA GGCTGGAGTG CAATGGCGTG
26581 ATCTCGGCTC AATGCAATCT CTGTCTCGTG GGTTCAAGCG ATTCTCCTGC CTCAGCCTCC
26641 CAAGTAGCTG AGATTACAGG CACCAGCCAC TATGCTCAGC TAATTTTTG TATTTTTAGT
26701 AGAGATGGGG TTTCAACATG TTGGCCAGGC TGGTCTCGAA CTTCTGACCC CAAGTGATCC
26761 GCCCGCCTCG GCCTCCCAAA GTGCTGGGAT TACAGGCGTG AGCCACCATG CCTGGCGTGC
26821 TTAGCCTATT TTAATGGGA GTTTCATCCT CAATGGTGAG TGCTTTCATT GTCTTTAGGT
26881 GCCCCAGACC ATGTTTTTAA AAATTTAAAT GCACGAAGAA ATAAGTAGCC CTGTATAGTA
26941 GTAATACTTT GTTGTGAATA ACTGTCATAA GTCATCTCTA AAACTGTATT TTTTATCTAG
```

FIG. 4 CONT'D

```
27001 TTATTATATA TGACTAGCTA TATGTCTAGT TTTTTAAATA ATACAAAGTA ATTTATTTTT
27061 GGCATCCTCA AAAACCAAAG AGATTAGGTA ATGTAGTGTA GAAGAGAGCA GAGCTTTAGA
27121 CCTGAGAAGA ATCTGCCCAT GACTCGTGAA ACTCCACAAC GAAAGTAGGA GACCCCAAAA
27181 AAGGGGTGAG TGTCATCTTT TCTGAATTTT TTTTTTTTTT TAGATGGAGT CTTGCTCTGC
27241 CACCAGGCTG GAGTGCAGTG GTGCAATCTC GGCTCAGCCT CCCGAGTAGC TAGGATTACA
27301 GGCACGCGCC ACCATGACCA GCTAATTTTT GTATTTTTAG TAGAGACAGC GTTTCACCAT
27361 GTTGGCCAGG ATGGTCTCGG TCTCTTGACC TCGTGATCCG CCCGCCTCGG CCTCCCAAAG
27421 TGCTGGGATT ACAAGCGTGA GCCACTGCAC TCGGCCGGTC AGATAATTTT TTTGGCCAGT
27481 TTTTACATAG AGTAATTTTA GGTTTTATGG CTGGCTTTGG GGCAAGGGG TTCTGGTTTT
27541 TATAGCTGGT CTTGGGGGAG AATGGAACCG AGTGACAAGA GGACAAGAGA GGGTCAGAGA
27601 AAAACTTCTG CTTCTGAGGC GGCTATTGAG GCCTTCATTT TGGAGTATTG TCCTCTAAGC
27661 CCCAGCAGTG TCAAACTGTA CACAAACCAT ACACAGCAGC CAGCTCGGGT GCTGTTAGGA
27721 AATGGTCTCA CTGCTGGGTC TGTGGGGTAT GTGTGTGTCT GGGTGTGTGG CTACTGTCTG
27781 CATCCTCCTC CCCCCTACAG CCTCCCCGCC TCCCCTCCAG CCACCCTGGG ATTGGTGACT
27841 CTCAGCCCCT CCCCTCAGCT CCCCTAGACC CTCCCAGAGC CTTTATCAGG GAGCTGGGAC
27901 TGAGTGACTG CAGCCTTCCT AGATCCCCTC CACTCGGTTT CTCTCTTTGC AGGAGCACCG
27961 GCAGCACCAG TGTGTGAGGG GAGCAGGCAG CGGTCCTAGC CAGTTCCTTG ATCCTGCCAG
28021 ACCACCCAGC CCCCGGCACA GAGCTGCTCC ACAGGTAGGC AAGTGGGAGA ATGCTGGATG
28081 GACCAGAGCT GGCACCAGGG GACAGGAGCC AGCGTCAGGA GGGAATAAAG CAGATGGCAG
28141 CCTCTGATAG GGGAGCAGGG GACTGGGAAG GTGAGCACAA AGCACCTGTA GGGCCGAGAG
28201 CTGGTTGGTG TTTGGAGCCT GTGGCTACAG ACTCATTCTT TCATACCAGA AAGTTTTTGC
28261 CTAAGTCTTG GGATTATCTA GTACTGGAAA ATAGCATCCA GGATCCCTCC TCCAGCTGAC
28321 TGAGGAAACA GACCAGTCCA TGTCCTACAA ATCTATCATC TTTCTTGGGA GCTAGAGTCC
28381 TCCTGGCACC ACTATAGCAT TGCACATCTC CTGGGGAGAT ATCTGATGGG GTAGCAGGGA
28441 AACTAAGCCC AAGGGCTGTA CCCCCTTCTC AGAAATACTT TCCACCCTCT CTCCAGACCA
28501 GGGCTTGGAC AGTGGAGTTG GGGGCTGGGG AAGCAGGGTC AAGCCAAGCT GCTGGTAATG
28561 AATGTCTCTT GTGTCTTCAC CCATGCTGTA TCTTCCTCTT CTCTCCTTTA CCTGAGTCCT
28621 GTCCCTTTGC TCTCCCAGGC ACCATGAGGA TCATGCTGCT ATTCACAGCC ATCCTGGCCT
28681 TCAGCCTAGC TCAGAGCTTT GGGGCTGTCT GTAAGGAGCC ACAGGAGGAG GTGGTTCCTG
28741 GCGGGGGCCG CAGCAAGGTA AGTCTCCCCT GGCAGAGTAC TGGGGACATC ACGGGAACTT
28801 GGGACTCTGC CTGTCTGGAC AGCTGTAGTG AGGAAACTGG GGTGGGGGGG TTGTCCGTCA
28861 GAGGGCATTT TGCCTCCCTT TGGATTTCTT TGTTTCTCTG GTCCTTTCAT GTTCCCACTG
28921 TCTCCAGGTG TGTTTGTGTC TCTGTATCTC TGCATGTCTT TGACACCTTG TACATAAAAG
28981 GTGCCCTACA AATATGTTGT TTGGTGGGTT GATTGATGGG AGACTTGGTG ATTGGATGGT
29041 ACTGTGAGGG GTGAGCTAGG GTGGTCTAAG GCTCTCTATA GTCTACCTCA GGTCCCTTTG
29101 CAAGGGACAG ATCTCTTCTA TTTCCTGGAT GGTATGAAAC AGTCAGAATT TCTTTCCCAA
29161 ATGGTTATTT GTGTGCTATT TTACCTATCA GTTATGTGTA TTGTTTTATT TTCAAAATGC
29221 AAATAAATTC CCTTATCTTT TGCTCATCCA CCCCCAGTAA CCTCAGGTGC TTCTAAGATC
```

FIG. 4 CONT'D

```
29281 CCAACCCCTT CCTTCTTCTC TTTTCTCCCT TGCCCGCCTC TATCCTCTGC TTAGTCAGGA
29341 TAGGAAAACA ACAACAGCAA AAAAACCAGA TTGAGCCTCG ATTTCCACAG TTCCTTTACG
29401 AAAAAGAATA GGAATTGTCA GGGTAGGGGT ACAGGGGGAG GATAGGGAGG AAGTCTTTTC
29461 AAGGTTTTGA AATGACAGCA ATTACATCGG TACAAATGCT TTTAAGATGA TTGCGGGTGG
29521 GACTTATTAC AAATTCAATG TGTGAAGTTT AACTGCCTCT TCAGCTCAAA TCTGTTCAGC
29581 ATCTCATTAT AGGAGGTGGG CAGAGTATTC AACAATTTGG GAAAAGTGGC TGCCTGAACA
29641 CCACATGCTG GGCCAAGGGA GTTATCACCA GGGCAGCCTT GCAGGTGGCA GCAGTTGTGC
29701 CATATCCAAA AGGCCAGAAC CGTTAAAAAA AAAAACACCC AGGGGAGTGC CAAGTATGGG
29761 CTGGACACCG TTTGGAGCCA CAAAGTTCCA GCCCAGGATA GTTAGAGTAT CTGAGTTCTT
29821 CTGAGACAAA CTTGTTTCAA GACCTTGGCC AATGAGATGT CCCCTCTGCC CCTCTTGGTC
29881 AATGAATGAG AGGGATTGCC ATCCTACCCC TTCTCCTTGA GAGTCTGTGA GGATGAGGGA
29941 AATTGGGGCA GGAAGAGGGT AGTACATAGG TGTGCCTAGG CAACTGGGTT GGTATGTGTG
30001 GGGGTGTGTT CTGTGTAAAT GCACTTCTGT GTGTGCACAA CAGCCGAAGG ATGCCTGGGT
30061 TCTGGAAAGA GAGGCGCTGC TGAGACTTGA GATTTGAGAT GAAAATCTCC AGCCATGATC
30121 ATTGTTATTG TCTCTCTGCA GCTGCAATTA ACTGGCTGTG TGGTGTGTGC CCACCACCCT
30181 GCTGTACGCA AGTTGCTAAA AAAAAAAAAA AAATCACAGG GACAATCAAG AGCCCGTGCT
30241 GGGCAACAGC TCTAGAACTT GGGATTCAGT TGTGGAGAGA AGAAGACGTG CCTTCTGAGC
30301 ATGTTGCCTT CCTGGAATTC TAGACCTAGG GCCAAAAGGG AGAGGGAGAG AAAACTAGAG
30361 GCGGAAAGCC ATGGAGAATA GAGAAGAGG TGGTGGAAAA CAGGGAGAGA AACATCCATG
30421 GACATCGTGC AGAGTGGGGG AATCACAGGT GCAGATGTGT GCCTCCAATC TCACCATGCA
30481 TGTGAATCAC CTGGGGGGCT GCTTAAAATG CAGATTCTGT CTCAGGAGGT CTGGGGTAGG
30541 AACAAGAGTC TGCATTTCTA ACAGGCTCTG TGTAGTGCTG GTGTTGCTGT TGGTCCACAG
30601 GTCACTCCTG GAGCACCTAC TTCTCGTCCA GTGTGAACCA GAGGAAACTC TGAAAGAAAT
30661 AGGGTGTCGG ATTCAGGATG GGCTCAGGAA GAGGCTGTTT CTTGTGGGAA AGGATGAGT
30721 GGATCCGGGT GGGAGCCTCC TGCCTCACCC CTCTTTGTTT CTTCCCTAGA GGGATCCAGA
30781 TCTCTACCAG CTGCTCCAGA GACTCTTCAA AAGCCACTCA TCTCTGGAGG GATTGCTCAA
30841 AGCCCTGAGC CAGGCTAGCA CAGGTAGGAG GCGGCCCTAG GGGAGAGGGG AATGAGGGGC
30901 AGGATTCTGA AGATAAGAGG CCTGGGAGAT CCTTTCAGAT GGGAGAGAGA TGGGGGATAG
30961 CTTAGTGAAT CGGTGAGGGT TGTGATCTGA ACCCCGCTCT CATCACTTTC CAACTTCACT
31021 CCCCATTTAG ACATCTGTTC TTGGTTTCAC AGATCCTAAG GAATCAACAT CTCCCGAGAA
31081 ACGTAAGTAC CCTCTTCTCC CTCCCTATCT CTTGCCACTT GCCCAGAGCT CTGTGGGCA
31141 TTGGGCCCAG GGGCCATTTT GTCCAGCCCC TTCTCACCTG GTACAAACAA TATGCCAGCT
31201 CCCACTGCTC AGCCAACCTT TCCTGAAAGG GAGAGGCCAT CCAGAACTAG GAGGAAGCTG
31261 GTGTGAGGGG CATGGTGGGC TCTCCCTCTG CTGGCTGGTC CTTGGAAAAC AAGGGGATCT
31321 CTTCGTGGCC CTGAAAATTC CAAATCAGGC ACCTGCTAGA GCAGAAAATT CTTGAAATGT
31381 GGAGGAAGGA AAGGTGAGCA GAGAGAGTGG GTTAGGGGA GGCACTTGCT AACTGTGAGG
31441 AGTCATGCTT TGACAAGAAA AAGGAACAGA GACCAGAAAC CCAGTCTCAG AAGTGTTGAC
31501 CCATGTCTGG GGAGATGCTT CACTTTCTCA TCATCACTGC TGACAATGTT GGCCCTTTTC
31561 TGCAGGTGAC ATGCATGACT TCTTTGTGGG ACTTATGGGC AAGAGGAGCG TCCAGCCAGG
```

FIG. 4 CONT'D

```
31621 TAGGAGTGTG TGGAGGTACA GTGGAAGGGC TTAGGGTACT GGCAGAGTAT GACAGAAGTC
31681 ACGTGCCTCA TATTTGTCAC CAGAGGGAAA GACAGGACCT TTCTTACCTT CAGTGAGGGT
31741 TCCTCGGCCC CTTCATCCCA ATCAGCTTGG ATCCACAGGA AAGTCTTCCC TGGGAACAGA
31801 GGAGCAGAGA CCTTTATAAG GTAGTCCTGT TGCAGCTGGG AGGAAGGATA GGGAGACTCT
31861 GCTTCCACCC CAGTCTCCCA ACTCTGTCTT TGAACACTGC CCGTCATAGC CAGCCCTTTG
31921 CTGTTGGATC AGGGTGTAGT TCACATTCAG AAAGATCCCT CTTACTTACA CTGTTCGCTT
31981 TACCCTAGAC TCTCCTACGG ATGTGAATCA AGAGAACGTC CCCAGCTTTG GCATCCTCAA
32041 GTATCCCCCG AGAGCAGAAT AGGGTAAGGA TTGTTCATTA GAGAGGGGAG AGGGGACTGG
32101 GGAGGGGGCT GTGGGGGTTG CCAGCTGTGC ATTTCCTCCC ATGCTACAGG TATTAAAGCT
32161 CATAGATTTG CCCTGAAATA CACTGCCAAT GCCCAGCACA CTGTCGGCCA AACACAAAGA
32221 CACTTAGAGG CACGTGTGTT TGTACACATC CCCCGTCTTT CATCTCTTTC CTCTGGATCA
32281 TGGACGGCAG CTGACTATTG AGCAGGAGTG AGTGTTGGGA GATGAGGAGA GAGGGGCTTC
32341 CCGATGGGCA ATTTCTGTTG TTTGGACTTC ATTCTTTTGT AATCTATGCA AAAAGATGGA
32401 GAAATTATTA TCTGATAATT ACAAATACCA CAACCAATTC ACAGGCAAGC ATTTGCCTCC
32461 CAGGCAGGCT GAGCCTTTCA AATCACTCAG AATCCTGGGT TACGGGCCC AGAAGGTAGT
32521 CATACACAAG GATGATTCAG GAAGAAATGC AAGGAACTCT GAAATCTAAT GGGGATTAGC
32581 AGGAAACCAT ATCTGAATCT CTCTTTAGCA TAATGAATAA GAACAATGGC CTGAATGTGA
32641 ATCCTGGATC TGCCACTCTA TCTGTATCTT TTTGGCCAAG GTACATATCC TCCTGTGCTT
32701 CAGTTTCCTC ATCTGAAAAA TGAAAGTGAT AATAGTATCT CACAGGGTTG TGGTTTTGAG
32761 GATTGAGTAT AGGTAAAGTG TTCAGAACAG TGCCGGGTGC ACAGTGCTGT GTGCCAATTT
32821 TATGATAATT GTCCCAGTTT GGGAGGTATG GGGGATGTCC TAATGTTTCC CCTGACTGGC
32881 TCTGTCTGGA CCCCAGGCCT GAGTGGGCTG ACAAATTCCT CACTTGGTAT GCGAGTGTAA
32941 GAGTCCCCCA GGGAAGTGTC TAGTCAAAAC ACGAACCTTC CGCCTTGACA CTGTCTTCCC
33001 ACACACAGCA AGAGCAGCTC CACCAATGGC TTTCTTTTCA CTAGCTTCCA AAGAATTGGG
33061 GTGGAGGGAG TGAAAAGGAG AGGGAGAGAG ATTGGGAAGG CTCGTAATCA TGGAGAGCCT
33121 CCTGCTTTTC TCTCTGTGTC CCTGTTACCC ATACTCACTG GTCTCAAGGT GGCACGCCCA
33181 AGACCCAAGG AGCTGGTGCT TGATGATGCT GCCTGTGCAT GAATTCCTGG GACCAGAGAC
33241 TGAGTCTGGC CCCCCATTTA GTGTTGGGTG AGAGGGCACA AAGAGCTATA ATAACTGTAA
33301 CTTGCTGATT ACATGGTAGT TACTGTATCA TTTTGCTCTC ATTAGATGGT TATTTCAGTC
33361 CTGCCGACGG CCAGATAATT ATACGAGCAG CTATATCTGG ATGACATACT CTGCTCCAGC
33421 GTTATGCACT GGCCATAAAG ATAATTACAG TGCAATTTTG CTATAGTATT TTATACAAAT
33481 GGCAAAAACA AGTGCATTGT GGAAATCTAC TTTTAATGCT TGTTTGTGCA TCCAGGCTCT
33541 TTCAGAGGGA CCCATAATTG CAGCTTTCAT AATCTTACCA TTGAGGGAGC ATTCCCAACC
33601 TGTTAGGTGT CAGGCAGAAT AGGACATAAG GTTTCTGGGA GCTGGCATTT AAAGATTAGA
33661 TGAGATGGAT CAACACAGAT CATTGTGTCA TCTGATTTCA TTCATGTGAA ACTGTAAGTA
33721 ATCCCTGGGC CTGTGCTTCC TCTGGGAGGT TTCTGGGAAG AGGAGGAACT GGATAAGGCA
33781 GGGGGAGCAT TCATAGTAGG GCACCTTGGG CAGGGCTGTG TGTGTGTCTG GCTCATGGTG
33841 GTGCTAGGAT GGCATGAACT TGGTTCCTAC ATCTTTGGTC CACATGGGCC CCACTGGCCA
```

FIG. 4 CONT'D

```
33901 TGCACACAGG TGTGTAGAGT AATGTAAATA TGGCAGCTGG GAAGGTGCAA GTACCTGCGG
33961 CTAGGAGAGT TCCATCCTCA GGCCCAAAGC CTGGAGGGCA GGCTGAGGGT CAAGACTTGT
34021 TCTTTCCTCT CTCACAGACG CCTCTCCCCT TCTCTCCTGC TGCCACAGCA GGTTTTCAGT
34081 GGGACTTTTT TACAGGATAT AAGATGTGAT TTCAGTGTTT TTTTTGTTT TGTTTTGTTT
34141 TTTGTCCTCA GTACTCCACT TCCGGACTCC TGGACTGCAT TAGGAAGACC TCTTTCCCTG
34201 TCCCAATCCC CAGGTGCGCA CGCTCCTGTT ACCCTTTCTC TTCCCTGTTC TTGTAACATT
34261 CTTGTGCTTT GACTCCTTCT CCATCTTTTC TACCTGACCC TGGTGTGGAA ACTGCATAGT
34321 GAATATCCCC AACCCCAATG GGCATTGACT GTAGAATACC CTAGAGTTCC TGTAGTGTCC
34381 TACATTAAAA ATATAATGTC TCTCTCTATT CCTCAACAAT AAAGGATTTT TGCATATGAA
34441 TGATGTGGTG TGTGTGTTTA CTTGTTTGGT TGGTGGGTTT TTCTGTTCCT TGACTCCTCC
34501 AGCTACATGG TAAATACACA CATACTTATG ATACACACAC TTCATATTTA AATGTAAATA
34561 ACTTTACATA TCTTTTTGTA TATATCTATT TCCTGAACAG TGCCTTACAC AGTGCTTTGC
34621 ACGATGAGTA TCAGATTTAT TTAGTGATTA AAATAAATAC ACGAATTTGG AAGATGGTTT
34681 CTAACACACA AAGATTTTTA CAGACCAGTT TTAGATAAAG AAAAAACAGG CCGGGCCCGG
34741 TGGCTCACGC CTGTAATCCC AGCACTTTGG GAGGCCGAGG CGGGTGGATC ACGAGGTCAG
34801 GAGGTCGAGA CCAGCCTGAC CAACATGGTG AAACCCCTTC TCTACTAAAA ATACAAAAAT
34861 TAGCCAGGCA TGGTGGCGCA TGCCTGTAAT TCCAGCTACT TGGGAGGCTG AGGCAGGAGA
34921 ATCGTTTGAA CCCAGGAGGC AGGGGTTGCA GTGAGCCGAG ATCACGCCAC TGCACTCCAG
34981 CCTGGGCAAC AAGAGCAAAA AACTCCGTCT CAAAACAAAA CAAACAAACA AAAAAACAA
35041 TAAAAAAAGA AAAAGAAAAA GAAAAAAAT ATTCAGAATG ACTTGTATTA CTAGGATGGG
35101 TCTGGGAGAT ATTCATTCCT GAATCTGACC CTACTTAATT AGAGAAGGAG GTGGGGATCA
35161 AGGCTGTCCG GAGACCCAGC CACAGAGGAG GACAAATCTA TGACCCTATA CAATTTTTTT
35221 GTCTCCAAAT GCTGAGCCTG GGTTCTGTGA CAGATCCTGG GGATGAAATG ATGACTCATA
35281 CACAGAGTTT ACAGTTTAGC AGGGCTGTGG ACAAGCAAAC AGAACTTGAT CCAGCTAGGA
35341 TGGGATGTGG ACAGGGAAGT TACTACCGAG GCCAAGAAAG AGAGGAGCAG ATATCTTCAC
35401 CGTTAACTGG CTGCCTTAGT TATTATAAAG GGAAAACATT TATCTCCCAC TCCTCTCTAA
35461 AGTGCCTGTT ACCAGCTCCT GCAGCTCTGA CTTAACAGTC CCCAGAATGT GTAAGGCACT
35521 TACATGTGGT ATGCATGGGT ATGGATGTCT TTTACTAATC TATGATGTCA ACTATCACCC
35581 GCCATCCTAA GGGGGGTTCT GTACCCTAAT GGAACAGCCA GTGAAATCCT CAGGCTCCTT
35641 ATCTTAGCGT GGTACAGGGG CCTTTGTTAT GCCCTGAAT TGCACTGATA AAACATCAAC
35701 ACATAGATTT CCCAAGGCAG TGTAAGGACA GGGCCACAGA GCCAGAGGCC ACTTCCTGCA
35761 GTCCTTTCAT TCTAGTGAAA ATTCTATCTT CCTACAGCCT GACTTGGGGC CACTTTGGAA
35821 TGCAGCTGT ATAGTGGGGG GCGGGGAAAG GAGGGAATAC TCACCCTAGT ATTACTTATG
35881 TCAGCTTTAT AGCCAGAGGT CAAAGAATGC CCCCACCCCA GAGCCTAGAC CCTTTTTCCA
35941 GTGAGTCATC TCTTTGACTT TTCAAAATTA TCTATCTATA GGGCTTAAAA CTGGGGACAC
36001 TTTTGCAGAG TCTAGGGGCT TTCTCTGGGT CATGAAAGCT ACAAGAGTTG GTTCTGCTCA
36061 GACTTGGTGG GAGTTAGGCT TATAGGCTGA GATGAGACAA TTGCTTTGCA AGTAGGAACA
36121 TTAAGTGCAG AAAGATTGCT CTCTAGTGGG ACTGACAAAA ATTGCAGTAC TGGGGACTCC
36181 AGAAAAAAAT GAAGACAAAT GTTAAGTTAG ATTCCTGTGT TTGTACTTGA AGAATGTGTG
```

FIG. 4CONT'D

```
36241 AAGGGATCCT GACCCTCCCT TTCCTGTTGT AAAACAGTTG ATGCCTAAAG AGATCTGGTC
36301 CACAAGACCT TGACTAAATT CCTGGCCCTT TCTTCTCCAT TTAACTTTGT ATATGTTTGT
36361 TATTGTGACT ATATGGTGAT TTACTTTAAA AAGACTTCAG TATAAGTGGT ATATACTTTC
36421 ACCTGCGTCT TTTGGATGAT TTGTTTTCAT GTGAAGTTTA TTGGGGTCAA CCCTCCAGAG
36481 ATGGCTGGGG CAGTTGGTTA GAAAGACTGT ATAGGCCCAG GCCCTTGCAA GCCCAGCAGC
36541 CCTCTGTCTC CAGAGTCATG CTGGAGGTCT GGACCTGCTG GCTGTGTGAT ATTCCACTTT
36601 AGGGAGACTC AGTCACCTTG CACAACTGTG AGAGCTGGGC CTGCCACTGA ACATTGTGT
36661 CAACCTCTAA GTGACCCTTT CACTAGATGG TAAAGTGAGA TGCCTCATCC CCAAACTATA
36721 AGAACAGTTC TATGGCTGTT TTTGTATCTC CTGGCTAACA AATGTTACAT GTTTGGCAGC
36781 ATTTGGTATA GTGCTTGCTT TCAGTATAGT CTGCCACCAG TTAATGAGGT TGTGGAAAGG
36841 AGGACACACA ATCTCCCAAA TTCATCAAGA GAATGGACAA TTGCTGAATG GCCAAACTGG
36901 CTTAGATCTG TTGGCAACAT TCAGTGTGTC CCTTCCTTTC CACTTATCCA TCAAGGAATT
36961 ACTGAATCCT ACCATGCGCC TGTCCTGGGA GTTTGTCCTT GGCTGCAAGC TATTTTCAGG
37021 CAGTGACTGG GATGGGATGG GAGAGAGGAT GAAACTGAAG GGTCTTGGAG CCTAAGAGCT
37081 TCCTCTGTAC TGAGGGAGGG AGGGCGACAT GACGAAGACT TCTAATGTCT TTGGTGGTGG
37141 TGGGTGGGGC AGGCAGTGTA GGTGGTTTTC GTTGATGAC AATTCTTGGG CAGAAGCATT
37201 TGAAAAGATG ATTTGGGAGA AGGGTGGGGA GGAAGAGTGA TCGAGTTCTA CACAGAGTTG
37261 GGGAGGGCAG GCTTCAGGAA GCAGGCCTGG GGTGCCAAAG TACAGTGAGA TCCGGTGACT
37321 TTCTTCATTT GGCCACCTAG ATGGAAGGAG GGACAGCAGT GGATTATCAG AAGGGTCCAG
37381 TAGTAGCGGT CTAGCCCTCA AGTGCTCCTT CATTCATTCA AGCAGGCTTA ATGTATTAAG
37441 CACTTATTGT GCCAGGAAGT GTGGTAAGGG TCAGTGTGGA CCTGCGGCCG TGTGCAAAGC
37501 CACAGATCCC TGCCTTCAGG AAGCCCACAG CCTAGTGGAG GAGATATATA GTAATCAAAC
37561 AATCTTACAA CATTTTGTAA AATGCCCATA GTAGATGTTC TGAGGAGAAG CTTTTGGAAC
37621 TGTGAGCGTA GAACAGGGGA GGTGAAGAGA GTTTGGATAG G
```

FIG. 4 CONT'D

QUANTITATIVE PCR OF THE COMPLETE HUMAN NEUROKININ B PRECURSOR

HIGH PRESSURE LIQUID CHROMOTOGRAPHY (HPLC) OF NEUROKININ B

CARDIOVASCULAR EFFECTS OF NKB IN CONCIOUS RATS

LOCALISATION OF NEUROKININ B mRNA EXPRESSION
IN VERTICAL SECTIONS OF THE PLACENTA

SEQUENCE LISTING

<160> NUMBER OF SEQ ID NOS: 11

<210> SEQ ID NO 1
<211> LENGTH: 121
<212> TYPE: PRT
<213> ORGANISM: Homo Sapiens

<400> SEQUENCE: 1

Met Arg Ile Met Leu Leu Phe Thr Ala Ile Leu Ala Phe Ser Leu Ala
1               5                   10                  15

Gln Ser Phe Gly Ala Val Cys Lys Glu Pro Gln Glu Glu Val Val Pro
            20                  25                  30

-continued

Gly Gly Gly Arg Ser Lys Arg Asp Pro Asp Leu Tyr Gln Leu Leu Gln
            35                  40                  45

Arg Leu Phe Lys Ser His Ser Ser Leu Glu Gly Leu Leu Lys Ala Leu
 50                  55                  60

Ser Gln Ala Ser Thr Asp Pro Lys Glu Ser Thr Ser Pro Glu Lys Arg
 65                  70                  75                  80

Asp Met His Asp Phe Phe Val Gly Leu Met Gly Lys Arg Ser Val Gln
                 85                  90                  95

Pro Asp Ser Pro Thr Asp Val Asn Gln Glu Asn Val Pro Ser Phe Gly
            100                 105                 110

Ile Leu Lys Tyr Pro Pro Arg Ala Glu
            115                 120

<210> SEQ ID NO 2
<211> LENGTH: 10
<212> TYPE: PRT
<213> ORGANISM: Homo Sapiens

<400> SEQUENCE: 2

Asp Met His Asp Phe Phe Val Gly Leu Met
 1               5                  10

<210> SEQ ID NO 3
<211> LENGTH: 706
<212> TYPE: DNA
<213> ORGANISM: Homo Sapiens

<400> SEQUENCE: 3
ggcacagagc tgctccacag gcaccatgag gatcatgctg ctattcacag ccatcctggc      60
cttcagccta gctcagagct ttggggctgt ctgtaaggag ccacaggagg aggtggttcc     120
tggcgggggc cgcagcaaga gggatccaga tctctaccag ctgctccaga gactcttcaa     180
aagccactca tctctggagg gattgctcaa agccctgagc caggctagca cagatcctaa     240
ggaatcaaca tctcccgaga aacgtgacat gcatgacttc tttgtgggac ttatgggcaa     300
gaggagcgtc cagccagact ctcctacgga tgtgaatcaa gagaacgtcc ccagctttgg     360
catcctcaag tatcccccga gcagaatagg tactccacac ttccggactc ctggactgca     420
ttaggaagac ctctttccct gtcccaatcc ccaggtgcgc acgctcctgt taccctttct     480
cttccctgtt cttgtaacat tcttgtgctt tgactccttc tccatctttt ctacctgacc     540
ctggtgtgga aactgcatag tgaatatccc caaccccaat gggcattgac tgtagaatac     600
cctagagttc ctgtagtgtc ctacattaaa aatataatgt ctctctctat tcctcaacaa     660
taaaggattt ttgcatacga aaaaaaaaa aaaaaaaaa aaaaaa                      706

<210> SEQ ID NO 4
<211> LENGTH: 121
<212> TYPE: PRT
<213> ORGANISM: Homo Sapiens

<400> SEQUENCE: 4

Met Arg Ile Met Leu Leu Phe Thr Ala Ile Leu Ala Phe Ser Leu Ala
 1               5                  10                  15

Gln Ser Phe Gly Ala Val Cys Lys Glu Pro Gln Glu Glu Val Val Pro
                 20                  25                  30

Gly Gly Gly Arg Ser Lys Arg Asp Pro Asp Leu Tyr Gln Leu Leu Gln
            35                  40                  45

Arg Leu Phe Lys Ser His Ser Ser Leu Glu Gly Leu Leu Lys Ala Leu
 50                  55                  60

| | | | | | | | | | | | | | | | |
|---|---|---|---|---|---|---|---|---|---|---|---|---|---|---|---|
| Ser | Gln | Ala | Ser | Thr | Asp | Pro | Lys | Glu | Ser | Thr | Ser | Pro | Glu | Lys | Arg |
| 65 | | | | 70 | | | | 75 | | | | | 80 | | |
| Asp | Met | His | Asp | Phe | Phe | Val | Gly | Leu | Met | Gly | Lys | Arg | Ser | Val | Gln |
| | | | | 85 | | | | | 90 | | | | | 95 | |
| Pro | Asp | Ser | Pro | Thr | Asp | Val | Asn | Gln | Glu | Asn | Val | Pro | Ser | Phe | Gly |
| | | | 100 | | | | | 105 | | | | 110 | | | |
| Ile | Leu | Lys | Tyr | Pro | Pro | Arg | Ala | Glu | | | | | | | |
| | | 115 | | | | | 120 | | | | | | | | |

<210> SEQ ID NO 5
<211> LENGTH: 37601
<212> TYPE: DNA
<213> ORGANISM: Homo Sapiens

<400> SEQUENCE: 5

```
aggctactgt aggtaaccac ccagcttggt tcttcagctc cacatggtgg ggttaggaga      60
ggaggaggag ggagatggat ggaaccaatt aggaacagca cctgggctcc tcacaggaat     120
gaaccagtca tgccatttgc atgtaaacag cttcccactt ctctcctcat cctaccaaat     180
gctcccaacc ctgggttctg gcccatgttc tttgcccaca cagccctgta attagctggg     240
taatgagaag cttttaatga gtcccattag catctcgtgt aataaagagg ccttgagacc     300
cagctgctgt cctcactttg ggatgaacac gggtccctgt gtagccagtg acttctgtca     360
gtacagtcta agttctcgga tggggtggga gacaaacatt tcaggacccc agcagcactt     420
gagaggttcc atggtggatc catgttttg actgtgatac aagaaacttg gctctggctt      480
ccttgttcat tttgtaaata acattttttc ttcttttaag agacagagtc ttactttgtt     540
gcccaggctg gagtgtagca atgcaattat agctcactgc agcctcaacc tcctgggctc     600
aagtgatcct cctgcctcag cctctgggat agctggggcc acaggcatgc accaccatgc     660
ctggctaatt tttaaaaatg ttttttgtaga gatggggtct tacttgctat gttgctcaga     720
ctggtctcga acttctggct tcaagcaatt ctcccacctc gcctcctaa agtgctggga      780
gtatgggcat gagccaccat gtccagcctt gtaaatacat ttttattgag cacctattat     840
atgtcaaaca ttataaagtg agggatacag tagcaaacaa aacagacaaa aattttttgcc    900
atcatgacac ttatattcct gggtgggagt ggtgataaaa agacaataag taaaatactt     960
agcatagtgg atgtaataag ttcatgaagg gaaaaatggg agtgaggtat atggaatttt    1020
ggggtggtga taattttaaa tagggtgatt ggggaatgct tgttgcaca gattgttttt     1080
gtagtaaata tgagataaag atacggttct ctcccaaact caaaatgtag aagagtagaa    1140
ggtcccaaat cttcaagtct cttggagagg ggggccaccc attccgtctg ggacagttaa    1200
ctgttccctc acaggtcaaa gtttatgcca gtgcagtaaa aagagtggga gacctggggt    1260
gagacaaacc tggatttgag gctgttcttc actgattagt agccatatgt actggagcaa    1320
gtgactgaac cttctgagcc tgttttctca tctggaaaat cagaatattt cctacttaca    1380
tggtcatggt gatgaaaacc agatggactg ctccatgcca agcaccctg caaacattca     1440
aaccctgcac ccattacaaa tactgggctg acggatggct ctggctttgc ttttgcatct    1500
ccgctgtctc attcagcagc agcatctggc tctggctctc ggctctgatc ctggttctga    1560
ctctcccctg gagctctctc ccttgggtga gaaataagca gataatctcc ctcatctgtg    1620
tgtggtgtga acaagaggct tgaaaggtca gagaagaaga tgcctgaact gcagggagac    1680
agattagagt ggggaaaatg taactctgag gaaaaaggga agcaattaag agatcaaggc    1740
caggggcagt ggctcatgcc tgtaatccca acactttggg aggctgaggc gggcagacca    1800
```

```
tgaggtcagg agttcgagac cagtctggcc aacatagtga aaccccgtct ctactaaaaa    1860
tacaaaaaaa ttagccaggt atggtggtgt gcacctgtaa tcccagctac ttgggaggct    1920
gaggcagaag aattgcatga acccgggagg cagaggttgc ggtgagccga gattgaacca    1980
ttgcactcca acctgggcaa cagtgtgaga ctctgtctcc aaaaaaaaaa aaaaaaaaaa    2040
aaatcaaggc cggggagggg gcaggggtgg cacagctatc gagttctgtt catcctctgt    2100
gagattacat caggaggtgt aaaagaactc tagaagaatg aagctaagtc cagctgattc    2160
agggttcaag aaggattgag gtgggagagg catcatgacc actggtgagg agtggaggaa    2220
ggccgacact ggagctttct ttgcccaagc agaggagggg tgtgacactc ttgaggacca    2280
atgtaatggc gcagctccct ctgggagggg gaaaggagag gactggaggg gatgctaaac    2340
tgaccttcta accttcaggg gcctgagtct ggttgtcctg ggtggggagg ggcgcctgcc    2400
tgaaactgtt ttagcccaga agtcaggcct gaaggttaaa gggcaaggag ctggtggatg    2460
aacaaggtgg ggaaagaggc ccagggtcca catctactga gctggactca ggcatgggaa    2520
gagagtaatt gatttatagg agaaaaggta gataaattta tttaatatgt atatatgagc    2580
acctttagaa tgaagaccca aagatatagg ggaaattgcc agttatttat ttattttttt    2640
tggagatgga gtctcactgt gtctgccagg ctagagtgca gtggcatgat ctcggctcac    2700
tgcaacctcc gcctgctggg ttcaagcaat tctcctgcct catcctcctg agcagctgtg    2760
actacaggca cgcaccacca tgcccggcta atttttttgta ttttttagta gagacagggt    2820
ttcaccatgc tggccaggct ggtctggaac tcctgacctt gtgatccgcc cgccttggcc    2880
tcccagagtg ctgggattat aggcatgagc caccgccccc agcctgaaat cgccaatttt    2940
atgtttatgt tttacaaagt atggacagct gtgtagaaat atgactggac agaagggcat    3000
gctctaatgt taacagactg agtggggaaa cccaggaagg cctgttgaga ttcctcctgg    3060
cctctctcat tccttccttc tgggtatggg gcaggaccct ctctgaatg gggagatctt     3120
aggacctaag ttaaataagg taggtcagat aattttttat ggccagtttt tacatacagt    3180
aattttaggt tttatggctg gctttgggga aaagaggtcc tggtttttat agctggcctt    3240
gggggagaat gggacccagc aacaggagga caggagaggg tcagagaaaa acttctgctt    3300
ctgaggctgc tactgaggcc ttcattttag ggtattgtct tctgagcccc agcattcctc    3360
ggtgtgaaaa attttaaaga aattttatag tccagaaatt gagttggtga attgtcttat    3420
aagccatgga actagtctct tagtcctgag aataggccag tctagttaaa tagttattag    3480
ttgtgtctaa ttttaggcag tgtgttgcag atgggcttcc accaaagcca ggcctctata    3540
tgatatgagt aatcagttat ttagtaagag gcatttttgt ctcaaaaaat aaataaataa    3600
aaatatatga ataaatgaat gtatgtttct tatcagacta cgtctgttct atcattaatt    3660
ccagaaggga ggagggtctg gttccccctt cccatcatgg cctgacctag ttttcaggtt    3720
aattttagaa caccccttggc tgtgaggagt ggtccattcg gatggttagg gagctttagg    3780
atttttacttt tggtttacaa agtaatgtga attaaacaga catttgagtt aaagttttta    3840
tttttttaata aaatatttga tttaagcatt ttttttaactg aattaattag agctcttttta   3900
tataattttga taatgaaaca ttacatacac aggcacatat aaatatatag acacataaac    3960
agaagtagag cttatagatt tatactttttt tttttttttt ttttttttaat gagacaggtt    4020
ctccttctgt catctaggct ggagtgcagt ggtgccatca cagctcactg cagccttgac    4080
ctccaaggct caagcaatcc ttctacctga ctggctagct gggactacag gcgcgtgcca    4140
ccatgcctgg ctaattcgtg tatttttttgt agatatgggg agttttacca tcttgcccag    4200
```

```
gctggtcttg aactcctggg ctcaagaaat tttcctaact tgacctccca aagtgttgga    4260
attacaggca tgaggcacta cgccagacca gattttttat ttgtcagttt ctaggtagtt    4320
ttccccaact tcagactatc aattttaaa ttatctgttt tatgtcttaa ttattaacta    4380
ggcaactcta aacttgtatc tctaagacat gacttttaga tgaaataagg tagaaaatgt    4440
atatttcaaa ggcatagaat ttagatctaa ataaggtaa agttatctaa attttaagcc    4500
attgtctttt ctattctaaa aggttttgga ggtttgggtg tagagaggga gatgccttta    4560
caaatggaat ttttgttgtt gtttttgttt tgagacggag tcttgctctg tcacccagag    4620
tctcgctctg tcgcccaggc tggagtgcag tggcacgatc tccgctcact gcaacctctg    4680
cctcccggct tcaagtgatt ctcccacctc aacctcctga gtagtgggga ttacagctgt    4740
gtgccaccac gcccagctaa ttttttgtatt tttagtagag accgagtttc accatgctgg    4800
ccaggctgat ctcgaactcc cacctcaggt gatccgctcg ccttggcctc ccaaagtgct    4860
gggataacag gcatgagcca ctgcacctgg ccttttctga gttttttaag gagtctgagt    4920
cattagaagt cttttctaga ttttttaaaa atgtggtatt gaagatggca aagaggaagg    4980 aggaatagg tggagtaaaa gtaaatggga ggatagtttt taagaaagga agtgaataga    5040
gacatcaaac acattttaaa aaaagatttt tagtctactg aacaaaattt tttaaaatag    5100
gatttaaaga gaaacacag aaggcttaaa aaatatacac atagcttgaa tattagctttt    5160 taattaagct gacttctaac catggagctc tttaacaaaa attcttttaa atttgtctct    5220
ctcctccttt aaaactttt gtagagatgg ggttcgccc tgttacccag gctggtctca    5280
agtccgggca acttctgggc taaagtgatc tgcctgtctc ggcctcccaa gtgataggat    5340
tacaggtgtg agccactgcg actcaccttta aatctcttgt taccagattt tagttgggac    5400
aaatgctgat atttaaaag tcacataaat attaagccga aaaggactga tttctgatta    5460
ggaaggaaac ctaagccacg gtgggaattt taattattaa actgtaaaat ggagcagcct    5520
ccattgttaa ttttgtatgg aatccaaagt ggcagtttga gtgtaattgt tttaggtcag    5580 gttttttgtgc tttaattaa tcaagacaat tgttaaggat agctgtgaca ctattatgtg    5640 tcctttaat ttgatctatc aattcttag aacaagtaat tttttaaat ttaggaattt    5700 tagtctaaag gatttatctt ttggccattg acaattagaa tttttaatgg ggtatttaat    5760
tccaatagca acttaatcca aagttttctt tatgtcaaag aaaacagaag cccaggaggg    5820
atgagacctt gtaagacaaa actcccctag gagcttggaa tgtttgaaaa tacatgtgtt    5880
gggctcccaa tcttttcata ctggctgtga tgttacctga aaaatcacat cctttggatg    5940
gtggagacca agcgggaata tccccatcta gtcacgtcat gctctcaagg acatgagaca    6000
agagggaaac ctctcaccct gtttttattt cagggactgg cagcaaagtt tgtcataaca    6060
gaagtcagca taaccagaac cacgaaactg accagtttgc agggccagtt caaacagtgg    6120
gttgcaggcc tgttctaccc tagggtaccc ctccttatga cagaacacca aaagacaaga    6180
caaaaacgaa ggaaacggc aacaacaaaa agctatttc tgaaggaaa atggcaacaa    6240 caacaacaaa agctatttct gaagggaatg gggtcaaact atgaatactt ataccacaaa    6300
gtactaaaaa atatatcaga ctcactatac caaggttagt cacacacaaa acctgttctc    6360
tcattaatct tacatttgga aaggaaaagg gaaacaatga ttttactgt ccactcatcc    6420 agagtccaca gagagaggaa aactggaaaa ctgggagtct ggcaggaaat tctcactcct    6480
ctgctggctt gccaggttcc tgtatttcct tctctgtggc ttccagaaaa gcacaatagc    6540
tttggtggtc ttatttgtga tgccaaactg tggtcttggc cccctaaagt ttcagtgaaa    6600
```

```
atcactgaca tgaagcagat taataggaa aaaggcatac aaatttatta aatacgaatg    6660
ggagccttta gaatgaagcc ttgaagctat aggggaaatt gtctattttt atgtttaggt    6720
ttaacaaagt atggacagct gtgtagaaat atgactggac agaaagggca cgatctaatg    6780
ttaacagact gagtggggaa acccagcaag gcctgtctgt tgagattcct cctagcctct    6840
ctcattcctt ccttctggtg tggggcagga ccctctctgg aatggaggtt ttatgaccta    6900
agtcaaataa cgtaggtcag atttttttt ttttttttt tttttgagc tggagtctct    6960 ctgtcaacag gctggagtgc agtggcgtga ccttggctca ctgaaacctc cgcccctgg    7020 gttcaagcca ttctcctgcc ttagcctcct gagtagctgg gattacaggg gtgtgccacc    7080
acgcccagct aattttttgta tttttagtac agacaggggtt tcaccttgtt ggtcaggctg    7140
gtctcaaatt cctgacctgg tgatccacct gcctcggcct cccaaagtgc taggattaca    7200
ggcgtgagcc actgtgcccg gcctttttt tttttttt ttttaggaa gttgtatttt    7260 gggctttta actagcttgt tttttaatta gattattgcc tttagggtgg agcccttaaa    7320
taaaaggggg gaagaaaaca taggttttag ggcctcatat ttaaatgggt aaagcaggca    7380
tagctggaag gcagaataca gaaccccct aatcaaggat ctcattttta tattgaatcc    7440
taggcccccc aaaagaggga aatgtcatgg gacgagatgt gtggcatttt tatcgagtgc    7500
cccactgtaa agatgctccc ccaaggctgg caggcagccc agtgccgatt agcccactct    7560
gtgcttagtc ttttttttt tttttttt gaggtggagt cttgctctgt tgcccaggct    7620
ggagtgcaat ggcgtgatct cggctcaatg caatctctgt ctcgtgggtt caagcgattc    7680
tcctgcctca gcctcccaag tagctgagat tacaggcacc agccactatg ctcagctaat    7740
tttttgtatt tttagtagag atgggggtttc aacatgttgg ccaggctggt ctcgaacttc    7800
tgaccccaag tgatccgccc gcctcggcct cccaaagtgc tgggattaca ggcgtgagcc    7860
accatgcctg gcgtgcttag cctattttta atgggagttt catcctcaat ggtgagtgct    7920
ttcattgtct ttaggtgccc cagaccatgt tttttaaaaat ttaaatgcac gaagaaataa    7980
gtagccctgt atagtagtaa tactttgttg tgaataactg tcataagtca tctctaaaac    8040 tgtattttt atctagttat tatatatgac tagctatatg tctagttttt taaataatac    8100
aaagtaattt attttggca tcctcaaaaa ccaaagagat taggtaatgt agtgtagaag    8160
agagcagagc tttagacctg agaagaatct gcccatgact cgtgaaactc cacaacgaaa    8220
gtaggagacc ccaaaaaagg ggtgagtgtc atcttttctg aattttttt tttttttaga    8280 tggagtcttg ctctgccacc aggctggagt gcagtggtgc aatctcggct cagcctcccg    8340
agtagctagg attacaggca cgcgccacca tgaccagcta attttttgtat ttttagtaga    8400 gacagcgttt caccatgttg gccaggatgg tctcggtctc ttgacctcgt gatccgcccg    8460
cctcggcctc ccaaagtgct gggattacaa gcgtgagcca ctgcactcgg ccggtcagat    8520 aattttttg gccagttttt acatagagta attttaggtt ttatggctgg ctttgggca    8580 aaggggttct ggtttttata gctggtcttg ggggagaatg gaaccgagtg acaagaggac    8640
aagagagggt cagagaaaaa cttctgcttc tgaggcggct attgaggcct tcatttttgga    8700 gtattgtcct ctaagcccca gcagtgtcaa actgtacaca aaccatacac agcagccagc    8760
tcgggtgctg ttaggaaatg gtctcactgc tgggtctgtg gggtatgtgt gtgtctgggt    8820
gtgtggctac tgtctgcatc ctcctccccc ctacagcctc ccgcctccc ctccagccac    8880 cctgggattg gtgactctca gccctcccc tcagctcccc tagaccctcc cagagccttt    8940
atcagggagc tgggactgag tgactgcagc cttcctagat cccctccact cggtttctct    9000
```

```
ctttgcagga gcaccggcag caccagtgtg tgaggagagc aggcagcggt cctagccagt    9060
tccttgatcc tgccagacca cccagccccc ggcacagagc tgctccacag gtaggcaagt    9120
gggagaatgc tggatggacc agagctggca ccagggggct gttatctcct gactgccctt    9180
cttcttcctt ttctttcatc tgtgtattgt caggcagcta ctaattgtca acccagaagc    9240
tgctgggttt agaccagggt ctcaataaat cacacccca cagaagcctg cgggcactgg     9300
gcactgattc ccccagtgtt tctgagtatt ccagtttgcc actgccttga ctgtaactaa    9360
tgctagtatc cattctcatt tttttaattt ttatttattt atttatttat tttttgagac    9420
agagtttcac tcttgtcacc caggctggag tacaatggcg cgatctcagc tcactgcaac    9480
ctccgcctcc caggttcaag tgattatcct gcctcagcct cctgagctgg gattacaggc    9540
atgcgccacc atgcccagct aattttttgta ttttagtag agacagagtt tcaccatgtt    9600
ggccaggctg gtcttgaact cctgacctca agtgacccgc ccatctcggc ctcccaaagt    9660
gctaggatta caggtgtgag ccactgcgcc cagcctattt cttttttgag atggaatctt    9720
gctctctcgc ccaggctgga atgcagcaag catgatctcg gctcactgca acctccatct    9780
cccgggctca agccatcctt cagcctcggc ctccccagta gctgagacca caggcacatg    9840
ccaccacgcc tggctaattt tttatatttt tggtaaagat gtggtttcac catgttgccc    9900
aggctggtct caaactcctg agctcaagtg attcactcgc cttggcctcc caaagtgcta    9960
ggattacagg tgtgagccac tgcacccggc cttacccatt atcttttgaa catctactat   10020
gcattaagct ctttacatgc attaactcta atactttcaa taaccctgtg aggtaggctc   10080
ttttctttct cccattttgt agttaaaaag ccaaggctca gagaggttaa ataacttgcc   10140
gggggttcca cagctgtaag tggtaaagct gggttacaaa ctatttgact ctagagcttt   10200
taaccactgc ctaagactgc ccctcatcaa tagaggcttg gcaacccat ggccctaggc    10260
agacctgggg gcaggagggc tgcataggaa agggcagaac tttctagttc tagaacaaac   10320
aataaaaga agaaagcctt cagaggctcc acattaattg gaacaaaggg gattatgaca   10380
gatgcttagg catgtttgtt gaattattaa taaataaaat cagactaggg actgggact    10440
ccagtcttgg aggccttcac aggcccagat cccaaaccca ccaaacccac tagacctgca   10500
gtggaagcta caatgagctt ggatagttcc tgcagttaac agcaatatac tatgtattct   10560
gcctcttct atttaaattt tttaacctga tatcttagta aaacttttc ataaaaattc     10620
cagacatttg gaagtgccaa aaatcaagtc attttttata tcttcagtaa ttctgtgcca   10680
taaacaaaca ggttgctagg tgctctatgg gatgtaaaac cttggccagg caaggtgact   10740
cactcctgta atcctagcac tttgggaggc tgaggcggga atattgcttg agcccaggaa   10800
tttgtgacca gtctgggcaa catagtgaga cctagactct acaaaaaaaa tttaaaaatt   10860
aggtgggtgt ggtggctcat acctgtagtc ccagctactt ggaaggctga ggtgggagga   10920
tcgcttgagc ccaggaggcg ggcaaggctg cagtgagctg tgatggtggc actgcactcc   10980
agcctgggcg acagagcaaa accctgtctc aaaaaaagag gcaaaacaa aaacttaaga    11040
atccttgttc tagattgggg cagactaaag agtcagttgc catggatgaa gcttgattgg   11100
atcctggaaa aggaaaaata aagcttcaaa ggacatgttt agaagtttat aaaggacatg   11160
tagagaaatc tgagagtgga tcgctgttgg atgagtgatg ttgattttct taggtgtggt   11220
gatggagtta tgattgtgta agagaatgtt ccagttcttg ggagaggcat gctgacattt   11280
tagggtaaaa tgtcatgata tctataacct actttaggat ggtagggtag caaggatttg   11340
tgtaaatgtg tatatgcatg tatttatatg cacacatatg tgtgtgtgtc agagcacaca   11400
```

```
gatagtgcaa ggtgttaaca ttatcagttg gtgcatttag atgaggaaca tacagtatac   11460
agatgttaat tgtatctttt ttcaactttt ctgtaagtta aaaaaacttt caaaataata   11520
agctatattg aattttaaa acatcatatt atgctattct tctgtataaa ttctccaatg   11580
gtgttccatt tcactcctta ccacagccta caaggcccat catgatctgc cccgacctac   11640
tctctgatcc tctctcttcc tgctcaagtg attctggcca ccctttttt ttcttctttt   11700 ttagacagtg ttgctctgtc acccaagctg gagtgcagtg gtgcgatctt ggctcactgc   11760
aacctccacc tcccgggttc aagcgattct cctgtctcaa cctctagagt agctgggatt   11820
acaggcatgc gccaccatgc ccagctaatt tttgctcacc ctggcttttt aatgtctctg   11880
gaatatgctg ccactcattc ctgcctcagg gtctacttct ttgcatcaca gcagatgcca   11940
ttatctgaca tcacactata tatttatttg cttgtgtagt tggtccccctt ctccacccta   12000 cagtagaatg taagtccagt gaaaatgaag actttgttca ctgttatgtc ccagtaccta   12060
gaacagttcc aggcactaag tagacactca ataaatgttg actagtgaaa aaaaatgtga   12120
gacctgggat cctgccttat aaggactcag tgtctagaaa agggagctgt tttccatgca   12180
aataactgta gtacaaagac gagtgtaggc aaattgctat ggggcttcaa agaaaggaga   12240
ggcaatccgg ggcttgggga atcagggagg gctttgagct gatctcccag gttggcagag   12300
ttgagtcaag agagcatcga gagctaaggc acacagtgat catgcatggg ctgggtaggg   12360
gcatgggaaa gagtcctgtc cgggtggtgt gcccagggaa tgcaggggtc ctgcgacatg   12420
aggctgggct cttaagtgtc agggaggaaa cccaggagag aaaagcactt ccagtgaaac   12480
cctgggaaag gccagagaga aggaggaaga gcatgggatc ttggacagag gctggagcaa   12540
attgtaactg acctccgctg attggatttt tgaccgtggt taggaccctg actattgctc   12600
attcagacat gagacacatt tgcttacagc ctctctttgt tgttcgaggg tctggatccc   12660
tcagcttaag agaggaatgg gggctctgaa gctctgggcc tcttcattgt ctccctgaat   12720
tcatttgctc tttctccttt gctcctttat ttgctccttc ttcctttgaa tggaggctga   12780 catgttgga cttgactgat ttgagaggag gggaaatttg gtacctagcc aacagctgac   12840
acagacagtg gctgccacct gtaggcaatt gtgaacagaa ggaatagaaa gctacaggag   12900
caaaactttg agaccagctt tcatattggt tcctcttacc tcactgcccct gggtagcagg   12960 tctttggttg gaactaatcg ttctctccct ccagtctcct attcatgctc ttacctcccg   13020
gcctcaagcc tgcacctctt gctgaaaaag atccaagagg tgactcccctt ccatctcttc   13080 agctccaccc cttgcttctc actgtgggtt aacttcctcc tttgaagtgg caggatctgg   13140
gtgccagttt gcctgtcagg aagtgtttct tatcactcca ctcccaatcc ccctggtccc   13200
aaactaggta cagaaattcc tactggggct gaagaacaat ttgccatcca caaacgtctt   13260
agacaagaca tggccagccg cccccctacaa gtgcctcagc acagcaaatc aggagctgca   13320
gcagctcttc taccagtgga aggcaagtgg agcccaggca cccctcctct catttcgtct   13380
tttttttccc tcccccctgat tttcctcttt tgcctccctc ttctatttt ttcccattaa   13440 aaaaattgtg gtaaaatata cataacatac aatctaccat tttaacggtg tttaagtgta   13500
tagttcagtg gcatgagcga cattcatgtt gttctgcagc catcactgcc atccatctcc   13560
atatgcgttt ttcatcaccc caaactgaaa ctctgtaccc attaagcaat aaccccctat   13620
tctcccattc ccctagcccc tgatatctta taatctactt tctgtttcta tgaatttcac   13680
ttttccaagt gcctcatata agtgggaatc atatttgtcc ttttgtgtct ggcttatttc   13740
acttagcata aagtaatttg ttctttttatt caggaaatgc ttattgagca cctgtctggg   13800
```

```
actaagcctt gccctgagag ctgagcatag agccctcctg gtgcttttat ttgatggtgt    13860
ccattccctc ccctagcctc cctcagttct cgcactcctc ctcaatggtc ctccagcccc    13920
ggcctctccc tgaggtgtct agtgcctgtc cttttcctc agtctctctc ctctcctagt    13980
gtcttctagt caatatttct cacctccctc cccagccctg ccctcccact ctatgattt     14040
agctcctgtc cctccttcct cacagtgcaa gaggttccgg gatcagctgt ccccgaagca    14100
ggtagagatc ctgagggaaa agctctgtgc cagtgaactg ttcaagggca agaaggcttc    14160
atatccccag aggtgagggc ctcccagacc ctgcacagcc agttccatca cgcagcagtt    14220
ctcaaacttg agcgtgcctt agaatcacct ggcaggattg tcaccccag gtgctgtgtc     14280
cctcctcaga gtctctgatc cagcaggtct tggggtgagg accaaaattt gccttctaa     14340
caactcccca ggtggtgctg atgtcttggt cctggactgt gctctgtgga cactgacaga    14400
ggatacgtgg atgtgggga agggcccggg aggactagga tgggaactct gggggtgggg    14460
aagaggcctc tgggccttgt cgcgctgcac acctcccatg tgttctcagt gtccccattc    14520
cattctgtgg tgactacatt gggctgcaag ggaaccccaa gctgcagaag ctgaaaggcg    14580
gggaggaggg gcctgttctg atggcagagg ccgtgaagaa ggtcaatcgt ggcaatggca    14640
aggtaagggc ctgcaggctg aactcctccc gcagctagtg cagagctgtg ggctggcatc    14700
tggagagcag atggcaggct gtgtttgcgc cctgccaggt ggagtggggg caattaatcc    14760
tgccttttcct caccccttgcc tgttccgtcc ctagacttct tctcggattc tcctcctgac   14820
caagggccat gtgattctca cagacaccaa gaagtcccag gccaaaattg tcattgggct    14880
agacaatgtg gctggggtgt cagtcaccag cctcaaggat gggctcttta gcttgcatct    14940
gagtgaggta tcagagctgg gtggggcaag ccttggactg gagaaggtgg tatgcatccc    15000
agggctgggg caggctggag gtgatgggga ccagaccttt cgctctgggc ctttgatgtc    15060
cctcaggtgc tcctgaagag aaaaaatgaa tccctttcct gctatttttc cctcttccta    15120
agatgtcatc ggtgggctcc aagggggact tcctgctggt cagcgagcat gtgattgaac    15180
tgctgaccaa aatgtaccgg gctgtgctgg atgccacgca gaggcagctt acagtcaccg    15240
tgactgagaa gtgaggccat gaactggggg tgaggggcgg cttacggtag atggccaggc    15300
tgatggtcat cgtgaccagg atcagaaagc gaagcatgta gggcagtgca ggccggggct    15360
tggaggtgtt tctcaggccc ccacccaggt tctctgggc ctcaagtcct ctgactcgca     15420
tgatgggggg gccatcatgg aaatgcggga gtcggggtga gggatgggc actagacttg     15480
gttttctgtt ccctctccag gttctcagtg aggttcaagg agaacagtgt ggctgtcaag    15540
gtcgtccagg gccctgcagg tggtgacaac agcaagctac gctacaaaaa aaaggggagt    15600
cattgcttgg aggtgactgt gcagtgagga ggggcaccca tgcagagatg gcagttgctt    15660
cctcctgaac cagcactaat cccctctgc cctcctgtgt gggaggatct ctaaccctc      15720
tgatcgtggc gcatggcttg gggattaaac taccttgaa gaggacccctt gtcccaaacc    15780
cttcttgttc tctcctccaa aagtagcttc ctccaacccg cagcctctct gcacactaat    15840
aaaacatgtg gcttggaaag gttcagtcag ggtgggtggg tccttgttcc ccctatcttt    15900
tcacccaggt gtacttagac ccctgcccc atgccctttt tcctcctcaa gctccttgga    15960
gccagctagt gaggtaataa gaaaggaaaa gaaggaaaat tgtctccggg ctccttgacc    16020
ggctgagctc tggggggtg tttagagaga ctgcggtggg tggaggggct gcgggggag     16080
ttaaggatgg ggctcaggtc gcaggtgcc agtggactga ttcattaagt gtgtccctgg     16140
aggaaagaag tgagcatccc tgtcttggca gaaactgggg tcctttggcg atttagcctg    16200
```

```
aaaagcagcc caaggctgga gggcttatgt atgctggggt gctggggaat gcagggtctc   16260
ctgtacttgg gaacgccatc accccttcta ctcccacaca cagcacaggg ctccatcaca   16320
ccagcctccc cgacaccccc ttccttctca cacacccgag atgccaaact gctgccaaca   16380
gttatcttgc tcgtctctgt cccacagctg gggcctgcag caggtggcac ttcacatcac   16440
tcacttgatg aggctccctc atcaagaccc tccatccct gtaacctggc cctttcctct    16500
cctcttcctt tattttcct gcgtcattgt cattatcttt ttctcaccct cccaactatc    16560
tcacaccatc tcattgtccc tgtttctgtg agctctgact aatatcaata tgtaatattt   16620
tgtaaaatgc tttaaatatt ttcctactcc ccctcatatc tattttctca tagattctgt   16680
cttgtctgtc ttgtctctac cttctgtctg gcctctacct ttggggaaca agctgctcat   16740
gtagtcacag taaaatttag atctgtggtc tgtgagagct tagcagggtc tgcctttgtt   16800
tttgtctctg gctgtctctt cctcttctca agatctctac cttgcctacc tcttcccgct   16860 tccttcccctt aactcactat gccttgggc tgggtctcc ctccacctga cttccatctg     16920
caggcagctc acggccggct atcatgctgg ccagggagaa ctgattaact tctcttcctg   16980
cctgcagatt aatctgctgt ctgagcacaa gccacgtgct tctggcacac cctgctttga   17040
gctgagatag aacctgggga atcatctgtt ttcaggcggg tgaggggcta gagcctgcct    17100
tgtttgggag gagggtggct ctgttcagaa taggggtagc tcaggctctg gccagccttc    17160
tcccgccccc aacagctccc cccatccttg acttctcaga atcaggccga aagagcctaa   17220
tctggccgag agtgggtggg tgacctgcgc ctcatcgccc ccgctctcca tctcatctcc   17280
tgctcccagg gcccaaattg tcgtcacttt cccagtgaag tgtctggtca ttttcagaag   17340
caatttcagg agaacatgca gctgccgctc cctatcctgc atttcccttc acagggctga   17400
aggcactgtc agctccctgg gctgggggtg atgggagagg ggaagggcta gggccctcac   17460
ccctgtcctc actgtgccca tcatgtagat ggactggagt tcaaggaagg gcaggcactc   17520
ccctcctcct ttactcttct gtcactctct tcctcctctt ctttcctgtc tctgcctctc   17580
ttttctggag cctaggagtg tgtgttttca tccctgaaa caaatagga ctcagttttcc     17640 ccacctgtgt tacagggttg gaattggctc catcactgtg ggagaagctg gagttctgct    17700
accagtcctc ccctccccag ccctgcctct tctctcccag ccctctccct tcagccagtt    17760
cagcgctctg agagtctggg ttgtttcagc ctctgagggg cacaagccat cctggattcc   17820 cctaaccccca tgaggagcca ttctagcatc tcacagctta aaccagctct agctcagtcc  17880
tcctggctta gtccatttt cttcctcagg ctctgagggc tcttgttcc ttgctctgtg      17940 gggttttctc cagttgtctc ctggctgcag acatggcag acatagaat gctgtcatcc      18000 ttccactctt cattggcatc tccacccagt gtcacatatg accctagccc tgctctcccc    18060
ttgccagtac ccctctggga ttttgcgaga gtccacaagt tgtgcatgtg gtggatatat    18120
tcaggccatc ttgtgtgtac aagctagagg gtctgcttcc acctctggcc tcagtgaatt   18180
tgctgactaa cctgtctcaa cacagcacaa ctgtacacac cttttcctgg cctcatccct    18240
aacccatcat agcagcaaag aggggaagtt gcagggagg agctgctaag gaccctggac     18300
tccaagtacc ctgctcctct aggccaggga catcatctga gatgtggctc aaataaaggg    18360
tgggtgttca agaaaaaaca cttggggact ctatagctgc aacacccact ttacatgtca   18420
tttccatatg atttgtaggc aaaatgaagc ccaggctgtc ctagccctcc aatacctccc    18480
tctctcatca cctctccaac atagcctagc attagctctt tcaagtcttt gctaatccca    18540
gagatcaagg ggtgatcaac tctccctgcc atcccccttgt tccccgcacc cccgcccccg   18600
```

-continued

```
gctcccccac catccttggc tcctgccatc ctctttgaga tgctgcatca tcaaaggaca   18660
ttatttatgg tgtacctttg ctgaagccct gcttccctgg tgccaggct tgggagcagg    18720
gatgggtggg ttggtggggg agaggggtgg atgcagagat tggacccagg aggcttttag   18780
tcctcagctc ttggcttaac acctcctcct cttacacacc caactccctc cagcctgccc   18840
agcttgggcc ttcagctcca gattggtggg gttaggagag gaggaggagg gagatggatg   18900
gaaccaatta ggaacagcac ctgggctcct cacaggaatg aaccagtcat gccatttgca   18960
tgtaaacagc ttcccacttc tctcctcatc ctaccaaatg ctcccaaccc tgggttctgg   19020
cccatgttct tgcccacac agccctgtaa ttagctgggt aatgagaagc ttttaatgag    19080
tcccattagc atctcgtgta ataaagaggc cttgagaccc agctgctgtc ctcactttgg   19140
gatgaacacg ggtccctgtg tagccagtga cttctgtcag tacagtctaa gttctcggat   19200
ggggtgggag acaaacattt caggaccca gcagcacttg agaggttcca tggtggatcc    19260
atgtttttga ctgtgataca agaaacttgg ctctggcttc cttgttcatt ttgtaaataa   19320
cattttttct tcttttaaga gacagagtct tactttgttg cccaggctgg agtgtagcaa   19380
tgcaattata gctcactgca gcctcaacct cctgggctca agtgatcctc ctgcctcagc   19440
ctctgggata gctggggcca caggcatgca ccaccatgcc tggctaatt ttaaaaatgt     19500
ttttgtagag atggggtctt acttgctatg ttgctcagac tggtctcgaa cttctggctt   19560
caagcaattc tcccacctcg ccctcctaaa gtgctgggag tatgggcatg agccaccatg   19620
tccagccttg taaatacatt tttattgagc acctattata tgtcaaacat tataaagtga   19680
gggatacagt agcaaacaaa acagacaaaa attttgcca tcatgacact tatattcctg    19740
ggtgggagtg gtgatagaaa gacaataagt aaaatactta gcatagtgga tgtaataagt   19800
tcatgaaggg aaaaatggga gtgaggtata tggaattttg gggtggtgat aattttaaat   19860
agggtgattg gggaatgctt tgttgcacag attgtttttg tagtaaatat gagataaaga   19920
tacggttctc tcccaaactc aaaatgtaga agagtagaag gtcccaaatc ttcaagtctc   19980
ttggagaggg gggccaccca ttccgtctgg gacagttaac tgttccctca caggtcaaag   20040
tttatgccag tgcagtaaaa agagtgggag acctggggtg agacaaacct ggatttgagg   20100
ctgttcttca ctgattagta gccatatgta ctggagcaag tgactgaacc ttctgagcct   20160
gttttctcat ctggaaaatc agaatatttc ctacttacat ggtcatggtg atgaaaacca   20220
gatggactgc tccatgccaa agcaccctgc aaacattcaa accctgcacc cattacaaat   20280
actgggctga cggatggctc tggctttgct tttgcatctc cgctgtctca ttcagcagca   20340
gcatctggct ctggctctcg gctctgatcc tggttctgac tctcccctgg agctctctcc   20400
cttgggtgag aaataagcag ataatctccc tcatctgtgt gtggtgtgaa caagaggctt   20460
gaaaggtcag agaagaagat gcctgaactg cagggagaca gattagagtg gggaaaatgt   20520
aactctgagg aaaaagggaa gcaattaaga gatcaaggcc aggggcagtg gctcatgcct   20580
gtaatcccaa cactttggga ggctgaggcg ggcagaccat gaggtcagga gttcgagacc   20640
agtctggcca acatagtgaa accccgtctc tactaaaaat acaaaaaaat tagccaggta   20700
tggtggtgtg cacctgtaat cccagctact tgggaggctg aggcagaaga attgcatgaa   20760
cccgggaggc agaggttgcg gtgagccgag attgaaccat tgcactccaa cctgggcaac   20820
agtgtgagac tctgtctcca aaaaaaaaa aaaaaaaaa aatcaaggcc ggggaggggg     20880
caggggtggc acagctatcg agttctgttc atcctctgtg agattacatc aggaggtgta   20940
aaagaactct agaagaatga agctaagtcc agctgattca gggttcaaga aggattgagg   21000
```

```
tgggagaggc atcatgacca ctggtgagga gtggaggaag gccgacactg gagctttctt   21060
tgcccaagca gaggagggt gtgacactct tgaggaccaa tgtaatggcg cagctccctc    21120
tgggaggggg aaaggagagg actggagggg atgctaaact gaccttctaa ccttcagggg   21180
cctgagtctg gttgtcctgg gtggggaggg gcgcctgcct gaaactgttt tagcccagaa   21240
gtcaggcctg aaggttaaag ggcaaggagc tggtggatga acaaggtggg gaaagaggcc   21300
cagggtccac atctactgag ctggactcag gcatgggaat tggtgttgtg agggccaaga   21360
cacttggcct cctaaaagtt tgctgaaaat cactgacatg agagtaattg atttatagga   21420
gaaaaggtag ataaatttat ttaatatgta tatatgagca cctttagaat gaagacccaa   21480
agatataggg gaaattgcca gttatttatt tatttttttt ggagatggag tctcactgtg   21540
tctgccaggc tagagtgcag tggcaatgat ctcggctcac tgcaacctcc gcctgctggg   21600
ttcaagcaat tctcctgcct catcctcctg agcagctgtg actacaggca cgcaccacca   21660
tgcccggcta atttttttgta tttttttagta gagacagggt ttcaccatgc tggccaggct   21720
ggtctggaac tcctgacctt gtgatccgcc cgccttggcc tcccagagtg ctgggattat   21780
aggcgtgagc caccgccccc agcctgaaat cgccaatttt atgtttatgt tttacaaagt   21840
atggacagct gtgtagaaat atgactggac agaagggcat gctctaatgt taacagactg   21900
agtgggaaa cccaggaagg cctgttgaga ttcctcctgg cctctctcat tccttccttc     21960
tgggtatggg gcaggaccct ctctggaatg gggagatctt aggacctaag ttaaataagg   22020
taggtcagat aatttttttat ggccagtttt tacatacagt aatttaggt tttatggctg    22080
gctttgggga aaagaggtcc tggttttat agctggccctt gggggagaat gggacccagc   22140
aacaggagga caggagaggg tcagagaaaa acttctgctt ctgaggctgc tactgaggcc   22200
ttcatttag ggtattgtct tctgagcccc agcattcctc ggtgtgaaaa attttaaaga    22260
aattttatag tccagaaatt gagttggtga attgtcttat aagccatgga actagtctct   22320
tagtcctgag aataggccag tctagttaaa tagttattag ttgtgtctaa ttttaggcag   22380
tgtgttgcag atgggcttcc accaaagcca ggcctctata tgatatgagt aatcagttat    22440
ttagtaagag gcatttttgt ctcaaaaaat aaataaataa aatatatga ataaatgaat     22500
gtatgtttct tatcagacta cgtctgttct atcattaatt ccagaaggga ggagggtctg   22560
gttcccccctt cccatcatgg cctgacctag ttttcaggtt aatttagaa caccccttggc   22620
tgtgaggagt ggtccattcg gatggttagg gagctttagg atttttacttt tggtttacaa  22680
agtaatgtga attaaacaga catttgagtt aaagttttta ttttttaata aaatatttga   22740
tttaagcatt ttttttaactg aattaattag agctcttttta tatattttga taatggaaca  22800
ttacatacac aggcacatat aaatatatag acacataaac agaagtagag cttatagatt    22860
tatactttt ttttttttt tttttttaa tgagacaggt tctccttctg tcatctaggc      22920
tggagtgcag tggtgccatc acagctcact gcagccttga cctccaaggc tcaagcaatc  22980
cttctacctg actggctagc tggactaca ggcgcgtgcc accatgcctg gctaattcgt   23040
gtattttttg tagatatggg gagttttacc atcttgccca ggctggtctt gaactcctgg   23100
gctcaagaaa ttttcctaac ttgacctccc aaagtgttgg aattacaggc atgaggcact  23160
acgccagacc agatttttta tttgtcagtt tctaggtagt tttccccaac ttcagactat   23220
caatttttaa attatctgtt ttatgtctta attattaact aggcaactct aaacttgtat   23280
ctctaagaca tgacttttag atgaaataag gtagaaaatg tatatttcaa aggcatagaa   23340
tttagatcta aataaaggta aagttatcta aattttaagc cattgtcttt tctattctaa   23400
```

```
aaggttttgg aggtttgggt gtagagaggg agatgccttt acaaatggaa ttttttgttgt    23460 tgttttttgtt ttgagacgga gtcttgctct gtcacccaga gtctcgctct gtcgcccagg    23520
ctggagtgca gtggcacgat ctccgctcac tgcaacctct gcctcccggc ttcaagtgat    23580
tctcccacct caacctcctg agtagtgggg attacagctg tgtgccacca cgcccagcta    23640
atttttgtat ttttagtaga gaccgagttt caccatgctg gccaggctga tctcgaactc    23700
ccaacctcag gtgatccgct cgccttggcc tcccaaagtg ctgggataac aggcatgagc    23760
cactgcacct ggccttttct gagttttttta aggagtctga gtcattagaa gtcttttcta    23820
gattttttaa aaatgtggta ttgaagatgg caaagaggaa ggaggaatag ggtgagtaa     23880 aagtaaatgg gaggatagtt tttaagaaag gaagtgaata gagacatcaa acacatttta    23940
aaaaaaagat tttagtctac tgaacaaaat tttttaaaat aggatttaaa gagaaaacac    24000
agaaggcttt aaaaatatac acatagcttg aatattagct tttaattaag ctgacttcta    24060
accatggagc tctttaacaa aaattctttt aaatttgtct ctctcctcct ttaaaacttt    24120
ttgtagagat ggggtttcgc cctgttaccc aggctggtct caagtccggg caacttctgg    24180
gctaaagtga tctgcctgtc tcggcctccc aagtgatagg attacaggtg tgagccactg    24240
cgactcacct taaatctctt gttaccagat tttagttggg acaaatgctg atattttaaa    24300
agtcacataa atattaagcc gaaaaggact gatttctgat taggaaggaa accctaagcc    24360
acggtgggaa ttttaattat taaactgtaa aatggagcag cctccattgt taattttgta    24420
tggaatccaa agtggcagtt tgagtgtaat tgttttaggt caggtttttg tgctttaatt    24480
taatcaagac aattgttaag gatagctgtg acactattat gtgtcctttt aatttgatct    24540
atcaattctt tagaacaagt aatttttttta aatttaggaa ttttagtcta aaggatttat    24600
cttttggcca ttgacaatta gaatttttaa tggggtattt aattccaata gcaacttaat    24660
ccaaagtttt ctttatgtca agaaaaacag aagcccagga gggatgagac cttgtaagac    24720
aaaactcccc taggagcttg gaatgtttga aaatacatgt gttgggctcc caatcttttc    24780
atactggctg tgatgttacc tgaaaaatca catcctttgg atggtggaga ccaagcggga    24840
atatccccat ctagtcacgt catgctctca aggacatgag acaagaggga aacctctcac    24900
cctgttttta tttcagggac tggcagcaaa gtttgtcata acagaagtca gcataaccag    24960
aaccacgaaa ctgaccagtt tgcagggcca gttcaaacag tgggttgcag gcctgttcta    25020
ccctagggta cccctcctta tgacagaaca ccaaaagaca agacaaaaac gaaggaaaac    25080
ggcaacaaca aaaagctat ttctgaaagg aaaatggcaa caacaacaac aaaagctatt    25140
tctgaaggga atggggtcaa actatgaata cttataccac aaagtactaa aaaatatatc    25200
agactcacta taccaaggtt agtcacacac aaaacctgtt ctctcattaa tcttacattt    25260
ggaaaggaaa agggaaacaa tgattttttac tgtccactca tccagagtcc acagagagag    25320
gaaaactgga aaactgggag tctggcagga aattctcact cctctgctgg cttgccaggt    25380
tcctgtattt ccttctctgt ggcttccaga aaagcacaat agcttggtg gtcttatttg    25440 tgatgccaaa ctgtggtctt ggccccctaa agtttcagtg aaaatcactg acatgaagca    25500
gattaatagg gaaaaaggca tacaaattta ttaaatacga atgggagcct ttagaatgaa    25560
gccttgaagc tataggggaa attgtctatt tttatgttta ggtttaacaa agtatggaca    25620
gctgtgtaga aatatgactg gacagaaagg gcacgatcta atgttaacag actgagtggg    25680
gaaacccagc aaggcctgtc tgttgagatt cctcctagcc tctctcattc cttccttctg    25740
gtgtggggca ggaccctctc tggaatggag gttttatgac ctaagtcaaa taacgtaggt    25800
```

```
cagatttttt tttttttttt tttttttttt gagctggagt ctctctgtca acaggctgga    25860
gtgcagtggc gtgaccttgg ctcactgaaa cctccgcccc ctgggttcaa gccattctcc    25920
tgccttagcc tcctgagtag ctgggattac aggggtgtgc caccacgccc agctaatttt    25980
tgtattttta gtacagacag gtttcacct tgttggtcag gctggtctca aattcctgac    26040
cttgtgatcc acctgcctcg gcctcccaaa gtgctaggat tacaggcgtg agccactgtg    26100
cccggccttt tttttttttt ttttttttta ggaagttgta ttttgggctt tttaactagc    26160 ttgttttta attagattat tgcctttagg gtggagccct ttaataaaaa gggggaagaa    26220
aacataggtt ttagggcctc atatttaaat gggtaaagca ggcatagctg gaaggcagaa    26280
tacagaaccc ccctaatcaa ggatctcatt tttatattga atcctaggcc ccccaaaaga    26340
gggaaatgtc atgggacgag atgtgtggca tttttatcga gtgccccact gtaaagatgc    26400
tcccccaagg ctggcaggca gcccagtgcc gattagccca ctctgtgctt agtctttttt    26460
tttttttttt ttttgaggtg gagtcttgct ctgttccca ggctggagtg caatggcgtg    26520
atctcggctc aatgcaatct ctgtctcgtg ggttcaagcg attctcctgc ctcagcctcc    26580
caagtagctg agattacagg caccagccac tatgctcagc taattttttg tatttttagt    26640
agagatgggg tttcaacatg ttggccaggc tggtctcgaa cttctgaccc caagtgatcc    26700
gcccgcctcg gcctcccaaa gtgctgggat tacaggcgtg agccaccatg cctggcgtgc    26760
ttagcctatt tttaatggga gtttcatcct caatggtgag tgctttcatt gtctttaggt    26820
gccccagacc atgtttttaa aaatttaaat gcacgaagaa ataagtagcc ctgtatagta    26880
gtaatacttt gttgtgaata actgtcataa gtcatctcta aaactgtatt ttttatctag    26940
ttattatata tgactagcta tatgtctagt ttttaaata atacaaagta atttattttt    27000
ggcatcctca aaaaccaaag agattaggta atgtagtgta gaagagagca gagctttaga    27060
cctgagaaga atctgccat gactcgtgaa actccacaac gaaagtagga gacccccaaaa    27120 aagggggtgag tgtcatcttt tctgaatttt tttttttttt tagatggagt cttgctctgc    27180
caccaggctg gagtgcagtg gtgcaatctc ggctcagcct cccgagtagc taggattaca    27240
ggcacgcgcc accatgacca gctaattttt gtattttag tagagacagc gtttcaccat    27300
gttggccagg atggtctcgg tctcttgacc tcgtgatccg cccgcctcgg cctcccaaag    27360
tgctgggatt acaagcgtga gccactgcac tcggccggtc agataatttt tttggccagt    27420
ttttacatag agtaatttta ggttttatgg ctggctttgg ggcaaagggg ttctggtttt    27480
tatagctggt cttgggggag aatggaaccg agtgacaaga ggacaagaga gggtcagaga    27540
aaaacttctg cttctgaggc ggctattgag gccttcattt tggagtattg tcctctaagc    27600
cccagcagtg tcaaactgta cacaaaccat acacagcagc cagctcgggt gctgttagga    27660
aatggtctca ctgctgggtc tgtggggtat gtgtgtgtct gggtgtgtgg ctactgtctg    27720
catcctcctc cccctacag cctccccgcc tcccctccag ccaccctggg attggtgact    27780
ctcagcccct cccctcagct cccctagacc ctcccagagc ctttatcagg gagctgggac    27840
tgagtgactg cagccttcct agatcccctc cactcggttt ctctctttgc aggagcaccg    27900
gcagcaccag tgtgtgaggg gagcaggcag cggtcctagc cagttccttg atcctgccag    27960
accacccagc ccccggcaca gagctgctcc acaggtaggc aagtgggaga atgctggatg    28020
gaccagagct ggcaccaggg gacaggagcc agcgtcagga gggaataaag cagatggcag    28080
cctctgatag gggagcaggg gactgggaag gtgagcacaa agcacctgta gggccgagag    28140
ctggttggtg tttggagcct gtggctacag actcattctt tcataccaga aagttttgc    28200
```

```
ctaagtcttg ggattatcta gtactggaaa atagcatcca ggatccctcc tccagctgac   28260
tgaggaaaca gaccagtcca tgtcctacaa atctatcatc tttcttggga gctagagtcc   28320
tcctggcacc actatagcat tgcacatctc ctggggagat atctgatggg gtagcaggga   28380
aactaagccc aagggctgta ccccttctc agaaatactt tccaccctct ctccagacca    28440
gggcttggac agtggagttg ggggctgggg aagcagggtc aagccaagct gctggtaatg   28500
aatgtctctt gtgtcttcac ccatgctgta tcttcctctt ctctccttta cctgagtcct   28560
gtccctttgc tctcccaggc accatgagga tcatgctgct attcacagcc atcctggcct   28620
tcagcctagc tcagagcttt ggggctgtct gtaaggagcc acaggaggag gtggttcctg   28680
gcgggggccg cagcaaggta agtctcccct ggcagagtac tggggacatc acgggaactt   28740
gggactctgc ctgtctggac agctgtagtg aggaaactgg ggtgggggg ttgtccgtca    28800 gagggcattt tgcctcctt tggatttctt tgtttctctg gtcctttcat gttcccactg    28860
tctccaggtg tgtttgtgtc tctgtatctc tgcatgtctt tgacaccttg tacataaaag   28920
gtgccctaca aatatgttgt ttggtgggtt gattgatggg agacttggtg attggatggt   28980
actgtgaggg gtgagctagg gtggtctaag gctctctata gtctacctca ggtccctttg   29040
caagggacag atctcttcta tttcctggat ggtatgaaac agtcagaatt tctttcccaa   29100
atggttattt gtgtgctatt ttacctatca gttatgtgta ttgttttatt ttcaaaatgc   29160
aaataaattc ccttatcttt tgctcatcca cccccagtaa cctcaggtgc ttctaagatc   29220
ccaacccctt ccttcttctc ttttctccct tgcccgcctc tatcctctgc ttagtcagga   29280
taggaaaaca acaacagcaa aaaaaccaga ttgagcctcg atttccacag ttcctttacg   29340
aaaaagaata ggaattgtca gggtaggggt acaggggag gataggagg aagtcttttc     29400 aaggttttga aatgacagca attacatcgg tacaaatgct tttaagatga ttgcgggtgg   29460
gacttattac aaattcaatg tgtgaagttt aactgcctct tcagctcaaa tctgttcagc   29520
atctcattat aggaggtggg cagagtattc aacaatttgg gaaaagtggc tgcctgaaca   29580
ccacatgctg ggccaaggga gttatcacca gggcagcctt gcaggtggca gcagttgtgc   29640
catatccaaa aggccagaac cgttaaaaaa aaaaacaccc aggggagtgc caagtatggg   29700
ctggacaccg tttggagcca caaagttcca gcccaggata gttagagtat ctgagttctt   29760
ctgagacaaa cttgtttcaa gaccttggcc aatgagatgt cccctctgcc cctcttggtc   29820
aatgaatgag agggattgcc atcctacccc ttctccttga gagtctgtga ggatgaggga   29880
aattggggca ggaagagggt agtacatagg tgtgcctagg caactgggtt ggtatgtgtg   29940
ggggtgtgtt ctgtgtaaat gcacttctgt gtgtgcacaa cagccgaagg atgcctgggt   30000
tctgaaagaa gaggcgctgc tgagacttga gatttgagt gaaatctcc agccatgatc      30060 attgttattg tctctctgca gctgcaatta actggctgtg tggtgtgtgc ccaccaccct   30120
gctgtacgca agttgctaaa aaaaaaaaaa aaatcacagg gacaatcaag agcccgtgct   30180
gggcaacagc tctagaactt gggattcagt tgtggagaga agaagacgtg ccttctgagc   30240
atgttgcctt cctggaattc tagacctagg gccaaagggg agaggagag aaaactagag    30300 gcggaaagcc atggagaata gagaaagagg tggtggaaaa cagggagaga acatccatg    30360 gacatcgtgc agagtggggg aatcacaggt gcagatgtgt gcctccaatc tcaccatgca   30420
tgtgaatcac ctgggggct gcttaaaatg cagattctgt ctcaggaggt ctggggtagg    30480
aacaagagtc tgcatttcta acaggctctg tgtagtgctg gtgttgctgt tggtccacag   30540
gtcactcctg gagcacctac ttctcgtcca gtgtgaacca gaggaaactc tgaaagaaat   30600
```

```
agggtgtcgg attcaggatg ggctcaggaa gaggctgttt cttgtgggaa aaggatgagt    30660
ggatccgggt gggagcctcc tgcctcaccc ctctttgttt cttccctaga gggatccaga    30720
tctctaccag ctgctccaga gactcttcaa aagccactca tctctggagg gattgctcaa    30780
agccctgagc caggctagca caggtaggag gcggccctag gggagagggg aatgaggggc    30840
aggattctga agataagagg cctgggagat cctttcagat gggagagaga tgggggatag    30900
cttagtgaat cggtgagggt tgtgatctga accccgctct catcactttc caacttcact    30960
ccccatttag acatctgttc ttggtttcac agatcctaag gaatcaacat ctcccgagaa    31020
acgtaagtac cctcttctcc ctccctatct cttgccactt gcccagagct ctgtgggca    31080 ttgggcccag gggccatttt gtccagcccc ttctcacctg gtacaaacaa tatgccagct    31140
cccactgctc agccaacctt tcctgaaagg gagaggccat ccagaactag gaggaagctg    31200
gtgtgagggg catggtgggc tctccctctg ctggctggtc cttggaaaac aagggggatct    31260 cttcgtggcc ctgaaaattc caaatcaggc acctgctaga gcagaaaatt cttgaaatgt    31320
ggaggaagga aaggtgagca gagagagtgg gtttagggga ggcacttgct aactgtgagg    31380
agtcatgctt tgacaagaaa aaggaacaga gaccagaaac ccagtctcag aagtgttgac    31440
ccatgtctgg ggagatgctt cactttctca tcatcactgc tgacaatgtt ggcccttttc    31500
tgcaggtgac atgcatgact tctttgtggg acttatgggc aagaggagcg tccagccagg    31560
taggagtgtg tggaggtaca gtggaagggc ttagggtact ggcagagtat gacagaagtc    31620
acgtgcctca tatttgtcac cagagggaaa gacaggacct ttcttacctt cagtgagggt    31680
tcctcggccc cttcatccca atcagcttgg atccacagga aagtcttccc tgggaacaga    31740
ggagcagaga cctttataag gtagtcctgt tgcagctggg aggaaggata gggagactct    31800
gcttccaccc cagtctccca actctgtctt tgaacactgc ccgtcatagc cagcccttg    31860 ctgttggatc agggtgtagt tcacattcag aaagatccct cttacttaca ctgttcgctt    31920
taccctagac tctcctacgg atgtgaatca agagaacgtc cccagctttg gcatcctcaa    31980
gtatcccccg agagcagaat agggtaagga ttgttcatta gagaggggag aggggactgg    32040 ggaggggct gtgggggttg ccagctgtgc atttcctccc atgctacagg tattaaagct    32100
catagatttg ccctgaaata cactgccaat gcccagcaca ctgtcggcca aacacaaaga    32160
cacttagagg cacgtgtgtt tgtacacatc ccccgtcttt catctctttc ctctggatca    32220
tggacggcag ctgactattg agcaggagtg agtgttggga gatgaggaga gaggggcttc    32280
ccgatgggca atttctgttg tttggacttc attcttttgt aatctatgca aaaagatgga    32340
gaaattatta tctgataatt acaaatacca caaccaattc acaggcaagc atttgcctcc    32400
caggcaggct gagcctttca aatcactcag aatcctgggt tacggggccc agaaggtagt    32460
catacacaag gatgattcag gaagaaatgc aaggaactct gaaatctaat ggggattagc    32520
aggaaaccat atctgaatct ctcttagca taatgaataa gaacaatggc ctgaatgtga    32580
atcctggatc tgccactcta tctgtatctt tttggccaag gtacatatcc tcctgtgctt    32640
cagtttcctc atctgaaaaa tgaaagtgat aatagtatct cacagggttg tggttttgag    32700
gattgagtat aggtaaagtg ttcagaacag tgccgggtgc acagtgctgt gtgccaattt    32760
tatgataatt gtcccagttt gggaggtatg ggggatgtcc taatgtttcc cctgactggc    32820
tctgtctgga ccccaggcct gagtgggctg acaaattcct cacttggtat gcgagtgtaa    32880
gagtccccca gggaagtgtc tagtcaaaac acgaaccttc cgccttgaca ctgtcttccc    32940
acacacagca agagcagctc caccaatggc tttctttca ctagcttcca aagaattggg    33000
```

```
gtggagggag tgaaaaggag agggagagag attgggaagg ctcgtaatca tggagagcct   33060
cctgcttttc tctctgtgtc cctgttaccc atactcactg gtctcaaggt ggcacgccca   33120
agacccaagg agctggtgct tgatgatgct gcctgtgcat gaattcctgg gaccagagac   33180
tgagtctggc cccccattta gtgttgggtg agagggcaca aagagctata ataactgtaa   33240
cttgctgatt acatggtagt tactgtatca ttttgctctc attagatggt tatttcagtc   33300
ctgccgacgg ccagataatt atacgagcag ctatatctgg atgacatact ctgctccagc   33360
gttatgcact ggccataaag ataattacag tgcaattttg ctatagtatt ttatacaaat   33420
ggcaaaaaca agtgcattgt ggaaatctac ttttaatgct tgtttgtgca tccaggctct   33480
ttcagaggga cccataattg cagctttcat aatcttacca ttgagggagc attcccaacc   33540
tgttaggtgt caggcagaat aggacataag gtttctggga gctggcattt aaagattaga   33600
tgagatggat caacacagat cattgtgtca tctgatttca ttcatgtgaa actgtaagta   33660
atccctgggc ctgtgcttcc tctgggaggt ttctgggaag aggaggaact ggataaggca   33720
gggggagcat tcatagtagg gcaccttggg cagggctgtg tgtgtgtctg gctcatggtg   33780
gtgctaggat ggcatgaact tggttcctac atctttggtc cacatgggcc ccactggcca   33840
tgcacacagg tgtgtagagt aatgtaaata tggcagctgg gaaggtgcaa gtacctgcgg   33900
ctaggagagt tccatcctca ggcccaaagc ctggagggca ggctgagggt caagacttgt   33960
tctttcctct ctcacagacg cctctcccct tctctcctgc tgccacagca ggttttcagt   34020
gggactttt tacaggatat aagatgtgat ttcagtgttt tttttgttt tgttttgttt   34080
tttgtcctca gtactccact tccggactcc tggactgcat taggaagacc tctttccctg   34140
tcccaatccc caggtgcgca cgctcctgtt acccttttctc ttccctgttc ttgtaacatt   34200
cttgtgcttt gactccttct ccatcttttc tacctgaccc tggtgtggaa actgcatagt   34260
gaatatcccc aaccccaatg ggcattgact gtagaatacc ctagagttcc tgtagtgtcc   34320
tacattaaaa atataatgtc tctctctatt cctcaacaat aaaggatttt tgcatatgaa   34380
tgatgtggtg tgtgtgttta cttgtttggt tggtgggttt ttctgttcct tgactcctcc   34440
agctacatgg taaatacaca catacttatg atacacacac ttcatattta aatgtaaata   34500
actttacata tcttttttgta tatatctatt tcctgaacag tgccttacac agtgctttgc   34560
acgatgagta tcagatttat ttagtgatta aaataaatac acgaatttgg aagatggttt   34620
ctaacacaca aagattttta cagaccagtt ttagataaag aaaaaacagg ccgggcccgg   34680
tggctcacgc ctgtaatccc agcactttgg gaggccgagg cgggtggatc acgaggtcag   34740
gaggtcgaga ccagcctgac caacatggtg aaaccccttc tctactaaaa atacaaaaat   34800
tagccaggca tggtggcgca tgcctgtaat tccagctact tgggaggctg aggcaggaga   34860
atcgtttgaa cccaggaggc agggggttgca gtgagccgag atcacgccac tgcactccag   34920
cctgggcaac aagagcaaaa aactccgtct caaaacaaaa caaacaaaca aaaaaaacaa   34980
taaaaaaaga aaagaaaaaa gaaaaaaaat attcagaatg acttgtatta ctaggatggg   35040
tctgggagat attcattcct gaatctgacc ctacttaatt agagaaggag gtggggatca   35100
aggctgtccg gagacccagc cacagaggag gacaaatcta tgaccctata caatttttt   35160
gtctccaaat gctgagcctg ggttctgtga cagatcctgg ggatgaaatg atgactcata   35220
cacagagttt acagtttagc agggctgtgg acaagcaaac agaacttgat ccagctagga   35280
tgggatgtga acagggaagt tactaccgag gccaagaaag agaggagcag atatcttcac   35340
cgttaactgg ctgccttagt tattataaag ggaaaacatt tatctcccac tcctctctaa   35400
```

```
agtgcctgtt accagctcct gcagctctga cttaacagtc cccagaatgt gtaaggcact    35460
tacatgtggt atgcatgggt atggatgtct tttactaatc tatgatgtca actatcaccc    35520
gccatcctaa gggggttct gtaccctaat ggaacagcca gtgaaatcct caggctcctt    35580
atcttagcgt ggtacagggg cctttgttat gcccctgaat tgcactgata aacatcaac    35640 acatagattt cccaaggcag tgtaaggaca gggccacaga gccagaggcc acttcctgca    35700
gtcctttcat tctagtgaaa attctatctt cctacagcct gacttggggc cactttggaa    35760
tgacagctgt atagtggggg gcggggaaag gagggaatac tcaccctagt attacttatg    35820
tcagctttat agccagaggt caaagaatgc ccccacccca gagcctagac cctttttcca    35880
gtgagtcatc tctttgactt ttcaaaatta tctatctata gggcttaaaa ctggggacac    35940
ttttgcagag tctagggct ttctctgggt catgaaagct acaagagttg gttctgctca    36000
gacttggtgg gagttaggct tataggctga gatgagacaa ttgcttttgca agtaggaaca    36060 ttaagtgcag aaagattgct ctctagtggg actgacaaaa attgcagtac tggggactcc    36120
agaaaaaaat gaagacaaat gttaagttag attcctgtgt ttgtacttga agaatgtgtg    36180
aagggatcct gaccctccct ttcctgttgt aaaacagttg atgcctaaag agatctggtc    36240
cacaagacct tgactaaatt cctggcccctt tcttctccat ttaactttgt atatgtttgt    36300
tattgtgact atatggtgat ttactttaaa aagacttcag tataagtggt atatactttc    36360
acctgcgtct tttggatgat ttgttttcat gtgaagttta ttggggtcaa ccctccagag    36420
atggctgggg cagttggtta gaaagactgt ataggcccag gcccttgcaa gcccagcagc    36480
cctctgtctc cagagtcatg ctggaggtct ggacctgctg gctgtgtgat attccacttt    36540
agggagactc agtcaccttg cacaactgtg agagctgggc ctgccactga acattgtgt    36600 caacctctaa gtgaccctt cactagatgg taaagtgaga tgcctcatcc ccaaactata    36660
agaacagttc tatggctgtt tttgtatctc ctggctaaca aatgttacat gtttggcagc    36720
atttggtata gtgcttgctt tcagtatagt ctgccaccag ttaatgaggt tgtggaaagg    36780
aggacacaca atctcccaaa ttcatcaaga gaatggacaa ttgctgaatg gccaaactgg    36840
cttagatctg ttggcaacat tcagtgtgtc ccttcctttc cacttatcca tcaaggaatt    36900
actgaatcct accatgcgcc tgtcctggga gtttgtcctt ggctgcaagc tattttcagg    36960
cagtgactgg gatgggatgg gagagaggat gaaactgaag ggtcttggag cctaagagct    37020
tcctctgtac tgagggaggg agggcgacat gacgaagact tctaatgtct ttggtggtgg    37080
tgggtggggc aggcagtgta ggtggttttc gtttgatgac aattcttggg cagaagcatt    37140
tgaaaagatg atttgggaga agggtgggga ggaagagtga tcgagttcta cacagagttg    37200
gggagggcag gcttcaggaa gcaggcctgg ggtgccaaag tacagtgaga tccggtgact    37260
ttcttcattt ggccacctag atggaaggag ggacagcagt ggattatcag aagggtccag    37320
tagtagcggt ctagccctca agtgctcctt cattcattca agcaggctta atgtattaag    37380
cacttattgt gccaggaagt gtggtaaggg tcagtgtgga cctgcggccg tgtgcaaagc    37440
cacagatccc tgccttcagg aagcccacag cctagtggag gagatatata gtaatcaaac    37500
aatcttacaa cattttgtaa aatgcccata gtagatgttc tgaggagaag cttttggaac    37560
tgtgagcgta gaacagggga ggtgaagaga gtttggatag g                       37601
```

<210> SEQ ID NO 6
<211> LENGTH: 121
<212> TYPE: PRT
<213> ORGANISM: Homo Sapiens -continued

```
<400> SEQUENCE: 6

Met Arg Ile Met Leu Leu Phe Thr Ala Ile Leu Ala Phe Ser Leu Ala
 1               5                  10                  15

Gln Ser Phe Gly Ala Val Cys Lys Glu Pro Gln Glu Glu Val Val Pro
             20                  25                  30

Gly Gly Gly Arg Ser Lys Arg Asp Pro Asp Leu Tyr Gln Leu Leu Gln
         35                  40                  45

Arg Leu Phe Lys Ser His Ser Ser Leu Glu Gly Leu Leu Lys Ala Leu
     50                  55                  60

Ser Gln Ala Ser Thr Asp Pro Lys Glu Ser Thr Ser Pro Glu Lys Arg
65                  70                  75                  80

Asp Met His Asp Phe Phe Val Gly Leu Met Gly Lys Arg Ser Val Gln
                 85                  90                  95

Pro Asp Ser Pro Thr Asp Val Asn Gln Glu Asn Val Pro Ser Phe Gly
            100                 105                 110

Ile Leu Lys Tyr Pro Pro Arg Ala Glu
            115                 120

<210> SEQ ID NO 7
<211> LENGTH: 25
<212> TYPE: DNA
<213> ORGANISM: Homo Sapiens

<400> SEQUENCE: 7
ggcacagagc tgctccacag gcacc                                         25

<210> SEQ ID NO 8
<211> LENGTH: 27
<212> TYPE: DNA
<213> ORGANISM: Homo Sapiens

<400> SEQUENCE: 8
ggcacagagc tgctccacag gcaccat                                       27

<210> SEQ ID NO 9
<211> LENGTH: 57
<212> TYPE: DNA
<213> ORGANISM: Homo Sapiens
<220> FEATURE:
<221> NAME/KEY: misc_feature
<222> LOCATION: 56
<223> OTHER INFORMATION: n =  is any nucelotide
<220> FEATURE:
<221> NAME/KEY: misc_feature
<222> LOCATION: 57
<223> OTHER INFORMATION: n =  is any nucelotide

<400> SEQUENCE: 9
aagcagtggt aacaacgcag agtactttttt ttttttttt tttttttttt tttttnn      57

<210> SEQ ID NO 10
<211> LENGTH: 5
<212> TYPE: PRT
<213> ORGANISM: Homo Sapiens

<400> SEQUENCE: 10

Phe Val Gly Leu Met
 1               5

<210> SEQ ID NO 11
<211> LENGTH: 4
<212> TYPE: PRT
<213> ORGANISM: Homo Sapiens
```

```
<400> SEQUENCE: 11

Asp Met His Asp
 1
```

PLACENTAL HUMAN NEUROKININ B PRECURSOR

The present invention is concerned with the detection of the production of the human precursor of neurokinin B by the placenta and to the detection of the production of neurokinin B gene products, or variants, or fragments thereof as a means of predicting the onset of pregnancy induced hypertension or pre-eclampsia or related foetal complications (or following their course). The application is also directed to methods of preventing or treating pregnancy-induced hypertension or pre-eclampsia by suppressing the effects of excessive neurokinin B secreted into maternal blood.

Pregnancy-induced hypertension (PIH) and pre-eclampsia, two of the most elusive and complex conditions of pregnancy, have been very difficult to define and manage. Pre-eclampsia is still one of the most common and life threatening complications of pregnancy in the Western World. The primary cause of pre-eclampsia has been difficult to elucidate because its signs and symptoms have always presented as a cluster of conditions. Hence, it has been defined as a syndrome, commonly presenting with the features of maternal hypertension and proteinuria, but including extensive complications involving the maternal liver, coagulation and nervous systems (Henriksen, T., (1998) Scand. J. Rheumatol. Suppl. 107 86-91). The clinical problems of pre-eclampsia normally become apparent only in the second half of pregnancy and are believed to emerge during the first trimester. It would appear that pre-eclamptic complications only present if placental tissue is present in the uterus of the mother. Indeed, cases of hydatidiform mole can present with pre-eclampsia where the uterus only contains disordered placental tissue (Nugent, C. E, et al (1966) Obstet. Gynecol. 87 829-31). Once pre-eclampsia is diagnosed during the course of pregnancy and the placental tissue is surgically removed or expelled during birth the condition ultimately clears. There have been many suggestions about the causes of pre-eclampsia ranging from the development of a poor placental/uterine vascular system to the immunology of incompatibility between the mother and foetus. Though these theories do have some substance they do not account for the systemic effects of this syndrome. Many symptoms are likely to be the result of secondary effects of hypertension and not the direct cause of the syndrome. Early detection of the development of PIH or pre-eclampsia would therefore be of great benefit in allowing precautionary measures to be taken, including specific treatment of hypertension and other complications associated with pre-eclampsia such as seizures, blot clotting problems etc.

The placental damage visible and hypertension observed in an expectant mother with pre-eclampsia has been implicated in an increased risk of foetal complications including growth retardation and foetal hypoxia. In extreme cases this could be a cause of miscarriage. In other studies, pre-eclampsia has been postulated as a maternal and foetal adaptation to foetal growth retardation. Since not all women with foetal growth retardation develop pre-eclampsia the decisive factor is a maternal response (Walker, J. (2000) The Lancet 356 1260-1265). Characteristics of this adaptation are present in not only pre-eclampsia but also in foetal growth retardation and miscarriage. For example, the failure of the normal expansion of plasma volume in the mother is associated with both impaired foetal growth and pre-eclampsia (Gulmezoglu A M, Hofmeyr G J (2000) Cochrane Database Syst Rev 2 CD000167). Problems observed in pre-eclampsia such as thrombophilia are suggested to be the result of thrombotic lesions in a pathological placenta (Mousa H A, Alfirevicl Z (2000) Hum Reprod 151830-3). It is apparent therefore that pre-eclampsia and foetal growth retardation and foetal hypoxia are linked, and diagnostic methods and treatments for pre-eclampsia may also be suitable in the prediction, diagnosis and/or treatment of these foetal conditions.

Neurokinin B (NKB) belongs to a family of peptides called tachykinins, the first and most well known of which is substance P which was discovered in 1931 (von Euler, U. S. and Gaddum, J. H. (1931) J Physiol 72:74-87). It took over another five decades before the discovery of a further two members of the tachykinin family, one designated substance K or neurokinin A (Kimura, S., et al (1983) Proc. Japan Acad 59B 101-104) and the other designated neuromedin K, now know as neurokinin B (Kangawa, K., et al (1983). Biochem. Biophys. Res. Commun. 114 533-540). The tachykinins have been implicated to have a wide variety of biological actions from smooth muscle contraction, vasodilation, pain transmission, neurogenic inflammation, to the activation of the immune system (Longmore, J., et al (1997) Canadian J. Physio. & Pharmacol. 75 612-621). Neurokinin B has been found to be the most potent neurokinin to cause vasoconstriction of both the mesenteric vascular bed (D'Orleans-Juste, P. et al (1991). Eur. J. Pharmacol. 204 329-334) and contraction of the hepatic portal vein (Mastrangelo, D., et al (1987) Eur J. Pharmacol. 134, 321-6). Neurokinin B is also the most potent member of the family to act at the $NK_3$ receptor and, whilst substance P and K slow down the heart rate, $NK_3$ receptor agonists have the opposite effect in that they increase heart rate when perfused in the canine coronary arterial blood supply (Thompson, G. W. et al (1998) American Journal of Physiology-Regulatory Integrative and Comparative Physiology 275 (5), 1683-1689). In an animal model, intravenous injections of neurokinin B in guinea pigs have been shown to produce a dose related hypertension, and very high levels of neurokinin B agonist led to animal discomfort (Roccon, A., et al (1996) Brit. J. Pharmacol. 118 1095-1102). Similar experiments have shown an increase in blood pressure upon intravenous infusion of neurokinin B in rats (Page et al., (2000) Nature 405 797-800). Neurokinin B has not been reliably found in any peripheral tissues taken from experimental animals; for example, Moussaoui et al (Neuroscience (1992) 48, 967-978) tested a wide range of peripheral tissues using a very sensitive and specific assay system and found no trace of neurokinin B at all.

A human neurokinin B precursor has been identified which, on processing, gives rise to a peptide identical to neurokinin B of other mammalian species (bovine, porcine, rat and mouse) (Incyte Pharmaceuticals Inc., International patent application no. WO98/57986). We have discovered, most surprisingly, that this human neurokinin B precursor is produced by placental tissue during pregnancy and that neurokinin B and fragments of the precursor are passed into the maternal bloodstream.

We have found that in normal pregnancy, substantial levels (eg 100 picomolar range) of neurokinin B (and other breakdown products of the human neurokinin B precursor) are found in the maternal blood stream near to term, but that zero or very low levels are found before this. However, in some cases near term levels are identified at an early stage of pregnancy (eg after only 9 weeks), and in cases of pregnancy induced hypertension or pre-eclampsia very high (nanomolar) concentrations of neurokinin B are found in the maternal plasma near to term. Thus, detection of raised plasma levels of neurokinin B, neurokinin B precursor, its breakdown products, or variants thereof at an early stage will provide an indication of the likely development of pregnancy induced hypertension or pre-eclampsia and may even provide an indication of the likely future severity of these conditions. Furthermore, reduction in the levels of circulating neurokinin B (or reduction of its effects) will ameliorate the adverse effects upon the mother seen in these conditions. As a result of the relationship between pre-eclampsia and foetal complications including foetal growth retardation and/or foetal hypoxia, neurokinin B agonists or antagonists may be useful in ameliorating these conditions. Overproduction of the human neurokinin B precursor may also be a causative factor in certain hypertensive conditions in non-pregnant individuals (either through the effect of neurokinin B or one or more of the other breakdown products of the precursor).

In a first aspect of the invention there is provided a method of predicting pregnancy induced hypertension in a human subject by assessing the concentration in a biological sample, e.g. blood, of a human neurokinin B precursor gene product or a variant or a fragment thereof.

In a second aspect of the invention there is provided a method of predicting pre-eclampsia or related foetal complications in a human subject by assessing the concentration in a biological sample, e.g. blood, of a human neurokinin B precursor gene product or a variant or a fragment thereof.

In a third aspect of the invention there is provided a method of diagnosing pregnancy induced hypertension in a human subject by assessing the concentration in a biological sample, e.g. blood, of a human neurokinin B precursor gene product or a variant or a fragment thereof.

In a fourth aspect of the invention there is provided a method of diagnosing pre-eclampsia or related foetal complications in a human subject by assessing the concentration in a biological sample, e.g. blood, of a human neurokinin B precursor gene product or a variant or a fragment thereof.

Preferably, the methods of the first, second, third or fourth aspects comprise assessing the concentration in a biological sample, e.g. blood, of neurokinin B.

In a fifth aspect of the invention there is provided a method of estimating the likely future degree of pregnancy induced hypertension in a human subject by assessing the concentration in a biological sample, e.g. blood, of human neurokinin B precursor gene product or a variant or a fragment thereof, and correlating the result with the predicted future severity of pregnancy induced hypertension.

In a sixth aspect of the invention there is provided a method of estimating the likely future degree of pre-eclampsia or related foetal complications in a human subject by assessing the concentration in a biological sample, e.g. blood, of human neurokinin B precursor or a variant or a fragment thereof, and correlating the result with the predicted future severity of pre-eclampsia or related foetal complications.

Preferably, the methods of the fifth and sixth aspects comprise assessing the concentration in a biological sample, e.g. blood, of neurokinin B, and correlating the result with the predicted future severity of pregnancy induced hypertension or pre-eclampsia or related foetal complications, respectively.

In a seventh aspect of the invention there is provided a method of preventing or treating pregnancy induced hypertension in a human subject by the administration of an agent which inhibits the biological effect of neurokinin B.

In an eighth aspect of the invention there is provided a method of preventing or treating pre-eclampsia or related foetal complications in a human subject by the administration of an agent which inhibits the biological effect of neurokinin B.

In a ninth aspect of the invention there is provided the use of a human neurokinin B precursor gene product or a variant or a fragment thereof in the manufacture of a diagnostic for use in the prediction or diagnosis of pregnancy-induced hypertension.

In a tenth aspect of the invention there is provided the use of a human neurokinin B precursor gene product or a variant or a fragment thereof in the manufacture of a diagnostic for use in the prediction or diagnosis of pre-eclampsia or related foetal complications.

Preferably, the ninth and tenth aspects comprise the use of an epitopic variant or epitopic fragment of human neurokinin B precursor. More preferably, the methods comprise the use of neurokinin B in the manufacture of a diagnostic for use in the prediction or diagnosis of pregnancy induced hypertension, pre-eclampsia or related foetal complications.

In an eleventh aspect of the invention there is provided the use of an agent which inhibits the biological effect of neurokinin B in the manufacture of a medicament for the prevention or treatment of pregnancy induced hypertension.

In a twelfth aspect of the invention there is provided the use of an agent which inhibits the biological effect of neurokinin B in the manufacture of a medicament for the prevention or treatment of pre-eclampsia or related foetal complications.

In a preferred embodiment of the eleventh and twelfth aspects, there is provided a pharmaceutical composition comprising an agent which inhibits the biological effect of neurokinin B, for use in the prevention or treatment of pregnancy induced hypertension, pre-eclampsia or related foetal complications.

In a thirteenth aspect of the invention there is provided a kit for the prediction or diagnosis of pregnancy induced hypertension comprising a binding partner, eg an antibody, to a neurokinin B precursor gene product or variant or fragment thereof.

In a fourteenth aspect of the invention there is provided a kit for the prediction or diagnosis of pre-eclampsia or related foetal complications comprising a binding partner, eg an antibody, to a neurokinin B precursor gene product or variant or fragment thereof.

In a fifteenth aspect of the invention there is provided a kit for the prediction or diagnosis of pregnancy induced hypertension, comprising a binding partner, eg an antibody, to a neurokinin B precursor gene product or variant or fragment thereof, together with instructions for the performance of an assay for predicting the levels of neurokinin B in a biological sample and correlating the assay results with the likely future development of pregnancy induced hypertension.

In a sixteenth aspect of the invention there is provided a kit for the prediction or diagnosis of pre-eclampsia or related foetal complications, comprising a binding partner, eg an antibody, to neurokinin B precursor gene product or variant or fragment thereof, together with instructions for the performance of an assay for predicting the levels of neurokinin B in a biological sample and correlating the assay results with the likely future development of pre-eclampsia or related foetal complications.

In a seventeenth aspect of the invention there is provided a kit for use in estimating the likely future degree of pregnancy induced hypertension, comprising a binding partner, eg an antibody, to a neurokinin B precursor gene product or variant or fragment thereof, together with instructions for the performance of an assay for predicting the levels of neurokinin B in a biological sample and correlating the assay results with the predicted future severity of pregnancy induced hypertension.

In an eighteenth aspect of the invention there is provided a kit for use in estimating the likely future degree of pre-eclampsia or related foetal complications, comprising a binding partner, eg an antibody, to a neurokinin B precursor gene product or variant or fragment thereof, together with instructions for the performance of an assay for predicting the levels of neurokinin B in a biological sample and correlating the assay results with the predicted future severity of pre-eclampsia or related foetal complications.

Preferably, the kits of the thirteenth to eighteenth aspects of the invention comprise a binding partner, e.g. an antibody, to a neurokinin B precursor, neurokinin B or epitopic variants or epitopic fragments thereof. More preferably the kits comprise a binding partner to the polypeptide sequences of FIG. 1 or 2, or epitopic variants or epitopic fragments thereof.

In a nineteenth aspect of the invention there is provided the use of an agonist of neurokinin B or neurokinin B in the preparation of a medicament for the reduction of blood volume in cases of hypotension.

In a twentieth aspect of the invention there is provided the use of an agonist of neurokinin B or neurokinin B in the reduction of blood volume in cases of hypotension.

In a twenty-first aspect of the invention there is provided a method of alleviating pre-eclampsia in a human subject by modifying the diet of the human subject to reduce the content of toxin generating substances therein.

In a twenty-second aspect of the invention there is provided a method of alleviating pre-eclampsia in a human subject including modifying the dietary pattern of the subject to reduce concentrations of potential toxins in the portal vein.

In a twenty-third aspect of the invention there is provided a dietary methodology for the alleviation of pre-eclampsia in a human subject in which the amount of toxin generating substances is reduced.

FIG. 1 shows the polypeptide sequence of cloned human neurokinin B precursor, available under Accession No. aaf76980.

FIG. 2 shows the polypeptide sequence of the active neurokinin B peptide.

FIG. 3 shows the polynucleotide sequence of placental cDNA of the human neurokinin B precursor, where ATG is the initiation codon; TAG is the stop codon; AATAAA is a polyadenylation signal; AAAAA is the polyA tail; and GGCACAGAGCTGCTCCACAGGCACC is the PCR primer based on *Homo sapiens* cDNA clone 138761 (Accession No. R63635) similar to the bovine clone, of Accession No. P08858 neurokinin B precursor used to amplify complete gene.

FIG. 4 shows the genomic sequence of neurokinin B, including the 27928 base pair promoter region, the introns, and seven exons (underlined).

Figure 5:
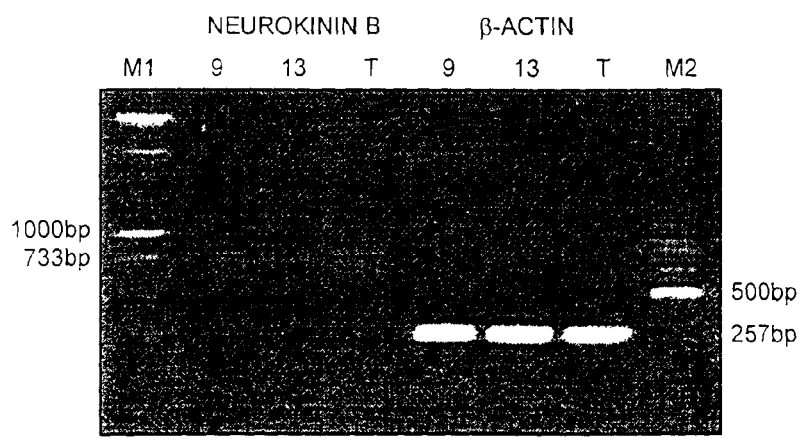

FIG. 5 shows the results of semi-quantitative PCR for the complete human neurokinin B precursor using mRNA collected at weeks 9, 13 and term. Reverse transcription PCR was performed using mRNA collected at weeks 9, 13 and term (T) to amplify a 733 by full length neurokinin B precursor cDNA. Primers for β-actin were used as the controls (257 bp). M1denotes a 1 kb DNA ladder; and M2 denotes a 100 by DNA ladder.

Figure 6:
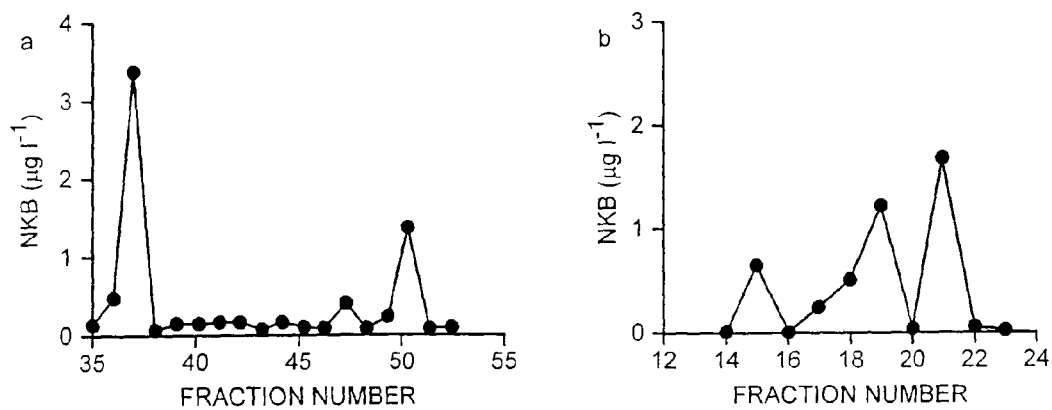

FIG. 6 shows HPLC results for oxidised and reduced neurokinin B in human pregnancy plasma and human term placenta. Placental extracts revealed the peptide to be present in significant amounts (21 pg g$^{-1}$ in early and 25 pg g$^{-1}$ in term placenta) and its chromatographic behaviour was identical to synthetic NKB. Partial oxidation of placental NKB during extraction resulted in the production of three oxidised forms in which one or both of the two-methionine residues were oxidised (a in plasma and b in placenta). The resulting methionine sulphoxides conferred reduced hydrophobicity, so that they eluted before the reduced form. This elution pattern matched that produced by the partial oxidation of synthetic NKB by hydrogen peroxide. Complete oxidation by hydrogen peroxide resulted in all the NKB eluting in the position of the first peak. A similar elution pattern was also observed after extraction of NKB from term placenta samples (b).

Figure 7:
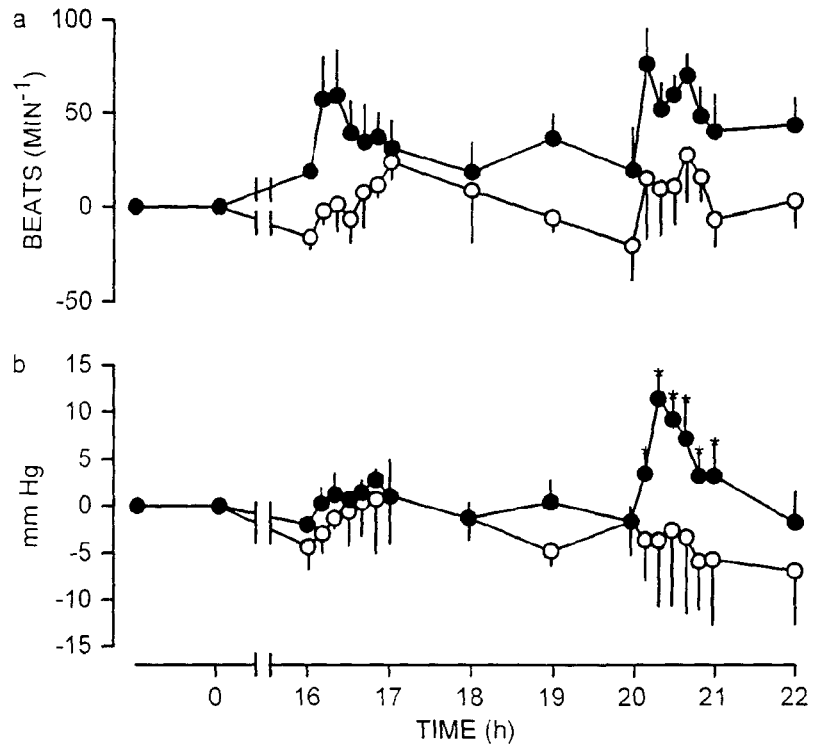

FIG. 7 shows the cardiovascular effect of neurokinin B in conscious rats. Changes in blood pressure and heart rate during infusion of saline or incremental doses of NKB in conscious unrestrained female rats. NKB was infused at doses of 1.8 nmol h$^{-1}$ (per kg) from time=0, 18 nmol h$^{-1}$ (per kg) from time=16 h and 180 nmol h$^{-1}$ (per kg) from time=20 h. Values are mean±s.e. mean. * denotes a significant difference from the original baseline and from the values at t=20 h (Friedman's test).

Figure 8:
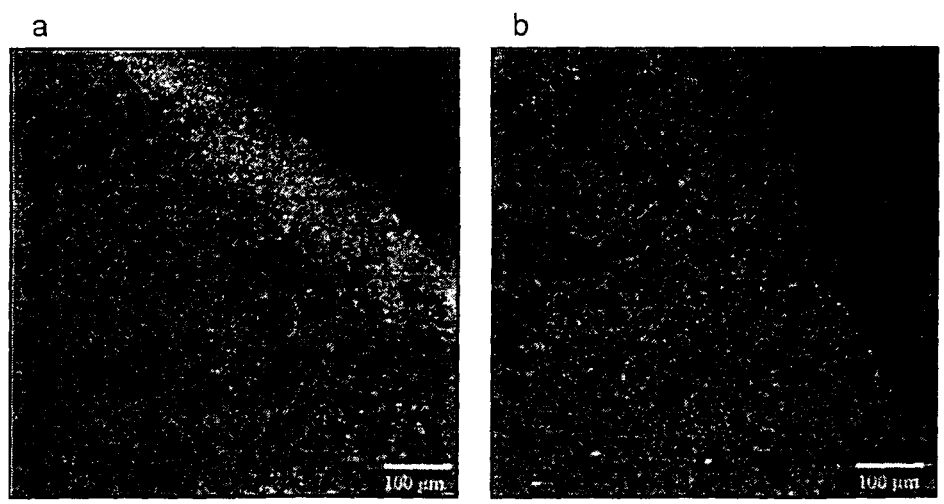

FIG. 8 shows an in situ hybridisation of for neurokinin B mRNA in the placenta of humans and rats. a, human at term (39 weeks) with human antisense probe b, human at term (39 weeks) with human sense probe c, rat 18 day placenta with rat antisense probe and d, high magnification showing giant cells of the rat placenta expressing neurokinin B. Magnification: a, 10×original size, b 10×, c 16×, d 40×.

The present invention is partly based upon the discovery that early and/or excessive release of neurokinin B into the maternal blood stream by the developing placenta can be a cause of pregnancy induced hypertension and pre-eclampsia. In particular, it has been postulated that those likely to suffer from pregnancy induced hypertension or pre-eclampsia have slightly elevated levels of neurokinin B in the maternal blood stream at approximately 10 to 12 weeks into pregnancy. Monitoring of neurokinin B early in pregnancy, for example at 10 to 12 weeks or before, is useful in predicting whether the individual is likely to suffer from pregnancy induced hypertension or pre-eclampsia later in pregnancy, and whether they are likely to suffer from pre-eclampsia related foetal complications such a foetal growth retardation, foetal hypoxia or miscarriage. Measurement of neurokinin B levels after 10 to 12 weeks into pregnancy, for example at 18 weeks may enable the prediction to be confirmed and a diagnosis of pregnancy induced hypertension or pre-eclampsia or related foetal complications to be made. Further, it has been observed that the level of increase in neurokinin B levels after any initial prediction of hypertension or pre-eclampsia correlates with the future severity of the condition. In particular, it has been shown that a relationship exists between the degree of increase in neurokinin B and the future severity of the condition. These observations can be used in the prediction of the future severity of the condition. Also, other post-processing fragments of the human neurokinin B precursor may be involved in the development of those conditions. In addition, the production of neurokinin B and/or other fragments of human neurokinin B precursor may be associated with the development of hypertension in non-pregnant individuals.

In the present invention, foetal complications include any foetal condition which is related to pre-eclampsia. Specifically, foetal complications include foetal growth retardation, foetal hypoxia, pre-term labour, and in severe cases, miscarriage.

For the purpose of the present invention, neurokinin B precursor gene products include polynucleotide sequences encoding neurokinin B precursor or neurokinin B, and neurokinin B precursor polypeptides. Polynucleotide sequences include genomic or cDNA sequences, for example those of FIG. 3 or 4, and RNA, preferable mRNA. Preferably, the neurokinin B precursor polypeptides have the sequences shown in FIG. 1. Fragments of neurokinin B precursor gene products are fragments which are derived from the precursor gene products and include the polynucleotide or polypeptide sequences encoding neurokinin B, fragments thereof, and other post-processing fragments of the precursor. Preferably the neurokinin B peptide derived from the precursor has the sequence of FIG. 2. Epitopic fragments or variants are those which comprise an amino sequence, typically of at least 4 residues, which constitutes a site to which the antibody can bind. A preferred epitopic fragment is the amino acid sequence DMHD (SEQ ID NO: 11) of FIG. 1.

Also included are variants of neurokinin B precursor gene products. Preferably, variants share at least 80%, at least 90%, at least 95%, at least 98% and most preferably at least 99% sequence identity with the neurokinin B precursor gene products or fragments thereof, and preferably retain the same biological activity as the gene product or fragment.

"% identity", as known in the art, is a measure of the relationship between two polypeptide sequences between two polypeptide sequences or two polynucleotide sequences, as determined by comparing their sequences. In general, the two sequences to be compared are aligned to give a maximum correlation between the sequences. The alignment of the two sequences is examined and the number of positions giving an exact amino acid or nucleotide correspondence between the two sequences determined, divided by the total length of the alignment and multiplied by 100 to give a % identity figure. This % identity figure may be determined over the whole length of the sequences to be compared, which is particularly suitable for sequences of the same or very similar length and which are highly homologous, or over shorter defined lengths, which is more suitable for sequences of unequal length or which have a lower level of homology.

Methods for comparing the identity of two or more sequences are well known in the art. Thus for instance, programs available in the Wisconsin Sequence Analysis Package, version 9.1 (Devereux J et al, Nucleic Acids Res. 12:387-395, 1984, available from Genetics Computer Group, Maidson, Wis., USA), for example the programs BESTFIT and GAP, may be used to determine the % identity between two polynucleotides and the % identity between two polypeptide sequences. BESTFIT uses the "local homology" algorithm of Smith and Waterman (Advances in Applied Mathematics, 2:482-489, 1981) and finds the best single region of similarity between two sequences. BESTFIT is more suited to comparing two polynucleotide or two polypeptide sequences which are dissimilar in length, the program assuming that the shorter sequence represents a portion of the longer. In comparison, GAP aligns two sequences finding a "maximum similarity" according to the algorithm of Neddleman and Wunsch (J. Mol. Biol. 48:443-354, 1970). GAP is more suited to comparing sequences which are approximately the same length and an alignment is expected over the entire length. Preferably, the parameters "Gap Weight" and "Length Weight" used in each program are 50 and 3 for polynucleotide sequences and 12 and 4 for polypeptide sequences, respectively. Preferably, % identities and similarities are determined when the two sequences being compared are optimally aligned.

Other programs for determining identity and/or similarity between sequences are also known in the art, for instance the BLAST family of programs (Altschul S. F. et al, J. Mol. Biol., 215:403-410, 1990, Altschul S. F. et al, Nucleic Acids Res., 25:289-3402, 1997, available from the National Center for Biotechnology Information (NCB), Bethesda, Md., USA and accessible through the home page of the NCBI at www.ncbi.nlm.nih.gov) and FASTA (Pearson W. R. and Lipman D. J., Proc. Nat. Acac. Sci., USA, 85:2444-2448, 1988, available as part of the Wisconsin Sequence Analysis Package). Preferably, the BLOSUM62 amino acid substitution matrix (Henikoff S, and Henikoff J. G., Proc. Nat. Acad. Sci., USA, 89:10915-10919, 1992) is used in polypeptide sequence comparisons including where nucleotide sequences are first translated into amino acid sequences before comparison.

Preferably, the program BESTFIT is used to determine the % identity of a query polynucleotide or a polypeptide sequence with respect to a polynucleotide or a polypeptide sequence of the present invention, the query and the reference sequence being optimally aligned and the parameters of the program set at the default value.

The first, second, third and fourth aspects of the invention relate to methods of predicting or diagnosing pregnancy induced hypertension or pre-eclampsia or related foetal complications in a human subject. These methods include, for example, assessing the concentration in a biological sample of neurokinin B precursor gene products, or variants or fragments thereof. These methods preferably comprise comparing the results of an assessment of the concentration of human neurokinin B gene product (e.g. neurokinin B or its precursor) in a sample with expected values or with the values found in the subject at an earlier date.

Preferably these methods are carried out at an early stage of pregnancy, for example at 10-12 weeks for prediction, or 18 weeks for diagnosis.

These methods may include any means of measuring neurokinin B gene products available to those skilled in the art. Preferably, the methods use the kits of the invention. The methods of the invention comprise at least the step of determining the presence of neurokinin B mRNA, neurokinin B or its precursor, or variants or fragments thereof, in a biological sample; however, additional steps may also be included. Such additional steps may include one or more of the following: collecting the biological sample; preparing the biological sample; measuring the concentration of target neurokinin B gene products such as polypeptide or polypeptides in the sample; preparing standard curves to predict expected concentrations of the target neurokinin B gene products in non-pregnant individuals or in pregnant individuals at the same or different stages of pregnancy; comparing the results obtained from a particular biological sample with the appropriate expected values or the appropriate standard curve to determine the severity of the condition; or repeating some or all of the previous steps at a later date to determine if the severity of the condition has changed.

Suitable methods of detection based on kits will be clear to one skilled in the art and include radioimmunoassay (RIA), enzyme linked immunosorbant assay (ELISA), immunoradiometric assay (IRMA), antisense technology, or radioreceptor assay (RRA). In the latter, for example the $NK_3$ receptor or other neurokinin B binding partner may be used in a detection system or biosensor system. Further detection methods may also include as well as radiometric methods, non-radioactive methods such as fluorescence and luminescence.

A preferred method is radioimmunoassay, which relies on the interaction of a small amount of radiolabeled peptide, eg neurokinin B, with a limiting amount of binding partner such as antibody (e.g. specific for NKB). The displacement of radiolabeled peptide by increasing doses of standard peptide is compared to that displaced by unknowns. This is normally monitored by separating binding partner bound label from free label usually by using a precipitation step which brings down the binding partner followed by centrifugation, although there are adsorbents (e.g. charcoal) which can bind the free labeled fraction and can then be removed by centrifugation. IRMA can be one site or two site and uses an excess of specific binding partner such as antibody which in this case is radiolabeled. In the one site assay, separation is effected by an excess of peptide linked to a solid phase which removes unreacted binding partner. In the two site method a second specific binding partner (usually linked to a solid phase) is used which is specific to a separate epitope on the peptide. Separation is easily effected by removal of the complex on the solid phase. RRA is similar to RIA in that a limiting amount of receptor is substituted for the antibody. Often the receptor preparation will be in the form of a membrane preparation so that washing and separation of the bound label can be performed by e.g. centrifugation. The use of enzymes as the signalling moiety in immunometric assays is commonly achieved by cross linking an enzyme to the specific antibody or the use of e.g. a pig anti mouse antibody cross-linked to an enzyme when a mouse monoclonal antibody is used in the initial reaction.

The above methods may also be used in estimating the likely future degree of pregnancy induced hypertension or pre-eclampsia or related foetal complications. These methods preferably comprise comparing the results of an assessment of the concentration of human neurokinin B gene product (e.g. neurokinin B or its precursor) in a sample with expected values. It is believed that the tenth week of pregnancy, or later, for example after 18 weeks, may be particularly valuable times at which to assess the presence (and concentration) of the human neurokinin B gene products.

The methods of the invention are preferably carried out in vitro, on a sample removed from the body. Any biological sample may be used in the methods of the invention. Preferred biological samples include blood, saliva or urine.

The invention also provides a method of preventing or treating pregnancy induced hypertension or pre-eclampsia or related foetal complications in a human subject by the administration of an agent which inhibits the biological effect of neurokinin B. Preferably, such methods are carried out using the kits of the invention. Agents which inhibit the biological effects of neurokinin B include any agents that act, for example, by removing the neurokinin B from the plasma; by altering its structure to prevent it binding to receptors; by binding to the receptors directly to block the binding of neurokinin B thereto (but without themselves causing the effects at those receptors normally caused by neurokinin B), by exerting a counter effect to the neurokinin B at the same or different receptors or by reducing or preventing gene expression or translation, for example by modulating activity of the neurokinin B gene promoter and/or by using antisense technology. Also included are agents which inhibit the production or processing of the precursor to prevent production of neurokinin B. Within this context, agents inhibiting the biological effect of neurokinin B include agents inhibiting the biological effect of any variants or fragments of human neurokinin B or its precursor which are involved in the development of pregnancy induced hypertension or pre-eclampsia or related foetal complications. The principal site of action of human neurokinin B is the $NK_3$ receptor and therefore preferred agents which inhibit the biological effects of neurokinin B for use in the invention include $NK_3$ receptor antagonists. However, at the high circulatory concentrations found in near term pregnancy, particularly in pregnancy induced hypertensive or pre-eclamptic subjects, neurokinin B may also have significant effects at other receptors (eg the $NK_1$ or $NK_2$ receptors) and therefore the agents which inhibit the biological effects of neurokinin B for use in the present invention also include agents which prevent neurokinin B's effects at such other specific receptors, as well as broad spectrum neurokinin antagonists and combinations thereof.

Since 1991, a number of high-affinity nonpeptide antagonists have been reported. Snider R. M., et al., (Science, 251: 435 (1991)), and Garret C., et al., (Proc. Natl. Acad. Sci., 88.:10208 (1991)), described CP-96,345 and RP 67580, respectively, as antagonists at the $NK_1$ receptor, while Advenier C., et al., (Brit. J. Pharmacol., 105:78 (1992)), presented data on SR 48968 showing its high affinity and selectivity for $NK_2$ receptors. More recently Macleod, et al., (J. Med. Chem., 36:2044 (1993)) have published on a novel series of tryptophan derivatives as $NK_1$ receptor antagonists. Recently, FK 888, a "dipeptide" with high affinity for the $NK_1$ receptor was described (Fujii J., et al., Neuropeptide, 22:24 (1992)).

Suitable $NK_3$ receptor antagonists for use in the present invention include all materials blocking or reducing the effect of neurokinin B at the $NK_3$ receptor, for example, those materials described in Gao and Peet (Current Medicinal Chemistry, 1999, 6, 375-388), Khavaga and Rogers (Int. J. Biochem Cell Biol. 1996, 28, 7, 721-738), U.S. Pat. No. 5,942,523, U.S. Pat. No. 5,846,973, U.S. Pat. No. 5,491,140, U.S. Pat. No. 5,328,927, U.S. Pat. No. 5,360,820, U.S. Pat. No. 5,344,830, U.S. Pat. No. 5,331,089, U.S. Pat. No. 4,742,156, U.S. Pat. No. 4,665,157, EP 591,040A, WO 94/01402, WO 94/04494, WO 93/011609, Canadian Patent Application 2,154,116, EP 693,489 and Canadian Patent Application 2,151,116. Specific examples of suitable antagonists include the receptor selective ligand, SR 142801 (Edmonds-Alt, et al., Life Sciences, 56:27 (1995)), and the decapeptides of formula: $A^1$-D-Pro$^2$-His$^3$-D$^4$-Phe$^5$-D-Trp$^6$-Val$^7$-D-Trp$^8$-Leu$^9$-Me$^{10}$—$NH_2$ wherein $A^1$ and $D^4$ are Asp or D-Asp amino acids.

Preferred agents for inhibiting the biological effects of neurokinin B include those which modulate activity of the neurokinin. B precursor gene promoter, thus altering the level of transcription of the neurokinin B precursor gene. Examples of such agents include competitive or non-competitive antagonists of neurokinin precursor B gene promoter transcription factors, agents which inhibit the biological effect of neurokinin B precursor gene promoter transcription factors, agonists of neurokinin B precursor gene promoter inhibitors, and polynucleotide sequences which bind to, and inhibit, neurokinin B precursor gene promoter activity. Preferably, such polynucleotide will be sufficiently complimentary to whole or part of the promoter sequence such that they hybridise thereto and inhibit promoter activity, preferably in vivo. Examples of suitable polynucleotide sequences are those which have at least 80%, 85%, 90%, 95%, 97%, 98% and preferably 99% sequence identity with the compliment of whole or part of the promoter. Preferably the polynucleotide sequence will be complimentary to a regulatory region of the promoter, for example a transcription factor binding site.

Where the agent is a polynucleotide sequence, it is preferably administered in the form of a vector. The vector may additionally comprise one or more regulatory sequences for activation of expression of the polynucleotide sequence, for example promoters including response elements, consensus sites, methylation sites, locus control regions, post-transcriptional modifications, splice variants, homeoboxes, inducible factors, DNA binding domains, enhancer sequences, initiation codons, and polyA sequences. Such agents may be administered by any suitable gene therapy technique, which will be known to persons skilled in the art.

Administration of pharmaceutical compositions is accomplished by any effective route, e.g. orally or parenterally. Methods of parenteral delivery include topical, intra-arterial, subcutaneous, intramedullary, intravenous, or intranasal administration. Administration can also be effected by amniocentesis related techniques. Oral administration followed by subcutaneous injection would be the preferred routes of uptake; also long acting immobilisations would be used. Also, as the effects of placental NKB will be on peripheral receptors, effectively drugs devoid of side effects to the central nervous system should be preferably peptide-like in their distribution properties. In addition to the active ingredients, these pharmaceutical compositions may contain suitable pharmaceutically acceptable carriers comprising excipients and other compounds that facilitate processing of the active compounds into preparations which can be used pharmaceutically.

Further details on techniques for formulation and administration may be found in the latest edition of "REMINGTON'S PHARMACEUTICAL SCIENCES" (Maack Publishing Co, Easton Pa.).

Pharmaceutical compositions for oral administration can be formulated using pharmaceutically acceptable carriers well known in the art, in dosages suitable for oral administration. Such carriers enable the pharmaceutical compositions to be formulated as tablets, pills, dragees, capsules, liquids, gels, syrups, slurries, suspensions, etc., suitable for ingestion by the patient.

Pharmaceutical preparations for oral use can be obtained through combination of active compounds with solid excipient, optionally grinding a resulting mixture, and processing the mixture of granules, after adding suitable additional compounds, if desired, to obtain tablets or dragee cores. Suitable excipients are carbohydrate or protein fillers. These include, but are not limited to sugars, including lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins, such as gelatin and collagen. If desired, disintegrating or solubilising agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterise the quantity of active compound (i.e. dosage).

Pharmaceutical preparations, which can be used orally, include push-fit capsules made of gelatin, as well as soft, sealed capsules made of gelatin and a coating such as glycerol or sorbitol. Push-fit capsules can contain active ingredients mixed with filler or binders such as lactose or starches, lubricants such as talc or magnesium stearate, and, optionally, stabilisers. In soft capsules, the active compounds may be dissolved or suspended in suitable liquids, such as fatty oils, liquid paraffin, or liquid polyethylene glycol with or without stabilisers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilisers or agents, which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner similar to that known in the art (e.g. by means of conventional mixing, dissolving, granulating, dragee-making, levigating, emulsifying, encapsulating, entrapping or lyophilising processes). The pharmaceutical compositions may also be modified to provide appropriate release characteristics, e.g. sustained release or targeted release, by convention means, e.g. coating.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilised powder in 1 mM-50 mM histidine, 0.1%-2% sucrose, 2%-7% mannitol at a pH range of 4.5 to 5.5, that is combined with buffer prior to use.

The agents for use in the invention (eg $NK_3$ receptor antagonists) can also be modified so that they are only delivered to selected target sites. For example, by adjusting their stability towards proteolytic digestion in the gut or ability not to pass the blood/brain barrier, or by producing composite molecules including a targeting component, e.g. an antibody selective for the target site.

After pharmaceutical compositions comprising a compound of the invention formulated in an acceptable carrier have been prepared, they can be placed in an appropriate container and labelled for treatment of an indicated condition. For administration of $NK_3$ receptor antagonists, such labelling would include amount, frequency and method of administration.

Pharmaceutical compositions suitable for use in the present invention include compositions wherein the active ingredients are contained in an effective amount to achieve the intended purpose. Thus, a therapeutically effective amount is an amount sufficient to ameliorate the symptoms of the disease being treated. The amount actually administered will be dependent upon the individual to which treatment is to be applied, and will preferably be an optimised amount such that the desired effect is achieved without significant side-effects. The determination of a therapeutically effective dose is well within the capability of those skilled in the art. Of course, the skilled person will realise that divided and partial doses are also within the scope of the invention.

For any compound, the therapeutically effective dose can be estimated initially either in cell culture assays or in any appropriate animal model (eg primates for pre-eclampsia, rats and guinea pigs for hypertension and other small laboratory animals for use with induced hypertension and induced pre-eclampsia). These assays should take into account receptor activity as well as downstream processing activity. The animal model is also used to achieve a desirable concentration range and route of administration. Such information can then be used to determine useful doses and routes for administration in humans.

A therapeutically effective amount refers to that amount of agent, which ameliorates the symptoms or condition. Therapeutic efficacy and toxicity of such compounds can be determined by standard pharmaceutical procedures, in cell cultures or experimental animals (e.g. $ED_{50}$, the dose therapeutically effective in 50% of the population; and $LD_{50}$, the dose lethal to 50% of the population). The dose ratio between therapeutic and toxic effects is the therapeutic index, and it can be expressed as the ration $ED_{50}/LD_{50}$. Pharmaceutical compositions, which exhibit large therapeutic indices, are preferred. The data obtained from cell culture assays and animal studies is used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors, which may be taken into account, include the severity of the disease state. Long acting pharmaceutical compositions might be administered every 3 to 4 days, every week, or once every two weeks depending on half-life and clearance rate of the particular formulation. Guidance as to particular dosages and methods of delivery is provided in the literature (see, U.S. Pat. Nos. 4,657,760; 5,206,344 and 5,225,212 herein incorporated by reference).

The agents which inhibit the biological effect of neurokinin B for use in the methods of the invention of preventing or treating pre-eclampsia; or of preparing medicaments for preventing or treating pre-eclampsia; are preferably formulated such that use of the agent is effective in, but not restricted to, the post prandial phase. The agents may for example be selected to be effective over a 24 hour period rather than exclusively in the post-prandial phase. The post-prandial phase is a particularly important time as it is believed that pre-eclampsia is associated with the build-up of toxins in the maternal blood supply due to the failure of the blood to pass through the liver (which normally removes the toxins) because of high pressure in the portal vein. Thus, transient relief of hypertension following meals will allow the blood to pass through the liver at the time when the highest concentration of toxins will be present and will therefore provide a large reduction in the risk of pre-eclampsia whilst producing only a short decrease in the effect caused by the placentally produced neurokinin B. This time limited effect may be achieved by selecting agents with short durations of activity and using appropriate formulations and dosage schedules.

Preferably, methods of prevention or treatment of the conditions addressed herein will begin as soon as possible after the initial prediction or diagnosis is made, for example after 10 weeks into pregnancy. The decision regarding initiation of a course of treatment will of course be the decision of a physician, and may therefore begin earlier or later. Typically, the course will be given throughout pregnancy or until symptoms subside. This may continue until up to eight weeks after birth. In individuals who have been determined as being at risk of developing foetal conditions such as growth retardation or hypoxia, or pre-eclampisa, (by consideration of other factors such as previous miscarriages or complications in pregnancy) the course may be initiated as soon as pregnancy is confirmed, and may continue until term.

In a further aspect of the invention there is provided the use of a human neurokinin B precursor gene product or a variant or fragment thereof in the manufacture of a diagnostic for use in the prediction or diagnosis of pregnancy included hypertension or pre-eclampsia or related foetal complications. Preferably, the gene product used is neurokinin B, or a variant or fragment thereof, for example in the production of a diagnostic comprising a binding partner specific for neurokinin B.

Preferably, the variants or fragments are epitopic. It is envisaged that other gene products could also be used, for example regulatory sequences of the neurokinin B precursor genomic sequence, or neurokinin B precursor mRNA in the production of antisense sequences.

The polypeptides used include human neurokinin B or its precursor, or variants or fragments thereof. Preferably, the polypeptides comprise the sequence of FIG. 1 or FIG. 2 respectively. Preferably, the fragments or variants are epitopic, as defined above.

These polypeptides may be produced in isolated, substantially pure form or as recombinant polypeptides. Method for doing so will be clear to one skilled in the art. These will include, for example, recombinant techniques or extraction, gel separation or more commonly, for peptides the size of neurokinin B, chemical synthesis, eg liquid and solid phase peptide.

In a further aspect of the invention there is provided the use of an agent which inhibits the biological effect of neurokinin B in the manufacture of a medicament for the prevention or treatment of pregnancy induced hypertension or pre-eclampsia or related foetal complications. Preferably, the agents are those defined above.

In a further aspect of the present invention there are provided kits for the predicting the onset of, diagnosing, or estimating the future severity of pregnancy induced hypertension or pre-eclampsia or related foetal complications. The kits of the invention comprise a means for detecting the production of human neurokinin B gene products such as polynucleotides or polypeptides encoding neurokinin B or its precursor, or fragments or variants thereof, by the subject. Thus the kits will commonly comprise one or more of: a binding partner to neurokinin B or its precursor; neurokinin B polypeptide or variants or fragments thereof; and/or polynucleotide sequences which hybridise to a sequence encoding neurokinin B or a variant or fragment thereof.

By binding partner is meant any substance capable of detecting (and binding to) the target, eg an antibody. Preferred binding partners for use in the kits of the invention are antibodies which are specific for neurokinin B precursor, or epitopic fragments or epitopic variants thereof. Preferred are antibodies to neurokinin B and antibodies to the human neurokinin B precursor. Most preferred are antibodies which are specific for neurokinin B, but antibodies specific to any other breakdown products of the neurokinin B precursor which remain in the body for a measurable time may also be used. These antibodies are capable of binding fragments of the human neurokinin B precursor to identify the production of the precursor by the human body. The antibodies of the invention may be, for example, polyclonal, monoclonal, chimeric or humanised antibodies or fragments thereof. Binding partners which cross react with related peptides such as Substance P or NKA, for example, may be useful as a medicament or in diagnosis, as they share a common sequence ($FVGLM-NH_2$) with neurokinin B.

Methods of producing such antibodies will be apparent to one skilled in the art. For example, in the case of polyclonal antibodies, by standard methods of animal immunisation or, for monoclonal antibodies, by the well-known methods of Köhler and Milstein, or by use of the methods discussed in U.S. Pat. No. 5,844,080. Chimeric antibodies can be made by genetic engineering techniques, and are antibodies in which the constant region is human in origin, but the variable regions are derived from, for example, a mouse antibody. The advantage of chimeric antibodies is to reduce immunogenicity. Humanised antibodies take this principle even further, in that only the complementarity determining regions and a minimum number of further amino acids in the variable regions are derived from an animal such as a mouse. The rest of the antibody structure is human in sequence, and is recognised by the human immune system as human (see, for example, Queen et al, PNAS, USA 86 (December 1989), 10029-10033).

Polynucleotides of the kits of the invention are preferably those which hybridise to a sequence encoding neurokinin B or its precursor, or a variant or fragment thereof, or complements thereof, under stringent conditions. Preferred are polynucleotide sequences which hybridise to the nucleotide sequence of FIG. 3 or FIG. 4, or their complements, under stringent hybridisation conditions. Stringent conditions are, for example, 6×SSC at 65° C. Preferably, such polynucleotide sequences have at least 85%, and least 90%, at least 95%, preferably at least 98% and most preferably at least 99% sequence identity with the compliment of the reference sequence. Such polynucleotide sequences are preferably at least 10 nucleotides in length, and will be useful in detecting expression of neurokinin B or its precursor. Such polynucleotides are useful in antisense technology or diagnostic PCR. Means of producing the polynucleotides of the invention will be clear to those skilled in the art, for example, they may be produced synthetically or by probing an appropriate cDNA or genomic library (particularly a placental cDNA library).

The kits of the invention may also comprise instructions for the performance of an assay for predicting or diagnosing the levels of neurokinin B in a biological sample (this may either be by direct measurement of neurokinin B or by measuring the concentration of human neurokinin B precursor, or a fragment thereof, and using this value to predict the amount of neurokinin B present). The components of the commercial neurokinin B radioimmunoassay kit RIK 7357 by Peninsula Laboratories, Belmont, Calif., USA can be used in the present invention. The kits of the invention preferably also comprise a key, showing the correlation between the levels of neurokinin B gene product in the biological sample and diagnosis of pregnancy induced hypertension or pre-eclampsia or related foetal complications, and/or the likely future onset and/or severity of these conditions.

Also provided are kits for the prevention or treatment of pregnancy induced hypertension or pre-eclampsia or related foetal complications, comprising means for inhibiting the biological effect of neurokinin B or its precursor in a subject. Preferably, such means include those agents defined above. In particular, the antibodies or polynucleotide sequences as described above may also be useful in these kits for inhibiting the biological effect of neurokinin B or its precursor. The kits preferably also contain instructions for use of the kit to prevent or treat pregnancy induced hypertension or pre-eclampsia or related foetal complications and/or a key showing the correlation between the amount of agent used and the likely effect on the condition.

Pre-eclampsia may also be alleviated by modifying the diet of a human subject to reduce the content of toxins (e.g. alkaloids) and toxin generating substances therein. Toxin generating substances include proteins which are digested in, and absorbed from, the gut as amino acids most of which are toxic if they circulate in blood in too high concentrations. Normally any amino acids in excess of daily requirement are immediately deaminated by the liver and metabolised. Increasing the proportion of carbohydrates in the diet may also be of particular benefit. The dietary pattern of the subject may also be modified to prevent peak concentrations of potential toxins appearing in the portal vein, for example by substantially reducing the size of individual meals (and increasing the frequency of small meals).

Agonists of neurokinin B may also be used as pharmaceutical agents where an increase in blood pressure or decrease in blood volume is considered to be beneficial. Suitable agonists include any acting to supplement or mimic the effect of neurokinin B at the $NK_3$ receptor (or at any other receptor), for example senktide or [MePhe$^7$] NKB.

The present invention also provides means of screening potential effective agents (eg $NK_3$ receptor antagonists and agonists) by testing their ability to block (or enhance) the hypertensive effect of neurokinin B in an appropriate model. Once suitable agents have been identified, they may then further be tested to determine their potential in preventing or treating hypertension; pregnancy induced hypertension or pre-eclampsia, and used accordingly. All agents identified by such a process (other than presently known materials) are included in the present invention. Screening methods include large array techniques such as the Vilsips™ technology of Affymetrix Inc; see, eg, EPB No. 0476014.

Transfected cells lines containing the cloned $NK_3$ (or $NK_1$ or $NK_2$) receptor could be used in receptor binding and cell signalling pathway studies in a way clear to one skilled in the art. Essentially, either cells lines expressing endogenously high levels of neurokinin receptors or cell lines transfected with cloned cDNA constructs of the neurokinin receptor may be used to produce membrane preparations. Membrane preparations, of purified receptors in solution or after reconstitution into phospholipid membranes, may then be used to assess receptor binding with labelled agonists and/or antagonists of neurokinin B. The effects of the action of the agonists and antagonists can be assessed using standard cell signalling assays. These will be typical of those routinely performed when using G-protein coupled receptors systems in a way clear to one skilled in the art (including such assays as receptor binding, cyclic AMP determination, protein kinase C, inositol triphosphate concentrations etc.). These studies could also be performed in animal models including the guinea pig and rat chronically infused with agonist to determine the long and short-term effects of neurokinin B, neurokinin B agonists and neurokinin B antagonists. Effects such as changes in heart rate, blood pressure, blood volume and weight of internal organs (e.g. uterus, placenta) may be measured.

EXAMPLES

Example 1

Production of Human Neurokinin B Precursor cDNA

The cloning of placental cDNA, using the following methods, was used to identify the human neurokinin B precursor having the polypeptide sequence shown in FIG. 1. The peptide sequence of neurokinin B in the precursor is underlined (the C-terminal G residue ends up as the amide on the C-terminal M in the final processed peptide of FIG. 2). The cloned placental cDNA of the human neurokinin B precursor is shown in FIG. 3 and has (underlined) the ATG initiation codon at 26-28, the TAG stop codon at 389-391, the AATAAA polyadenylation signal at 659-663 and the polyA tail starting at 680. Human placental tissue was obtained from pregnancy terminations at weeks 9 and 13 of gestation and term. Samples were collected in compliance with and approval from the Local Research Ethics Committee. RNA was extracted essentially as described by Chomczinski, P. and Sacchi, N. (1987) Analytical Biochemistry, 162, 156-159.

The full-length preproneurokinin B precursor was amplified using RT-PCR from total human term placental RNA. This was done using the SMART RACE cDNA amplification method (Chenchik, A. et al (1998)). In RT-PCR Methods for Gene Cloning and Analysis. Eds. Siebert, P. and Larrick, J. (BioTechniques Books, Mass.), 305-319). Essentially, after total RNA extraction, reverse transcription was performed using a cDNA synthesis primer (5'AAGCAGTGGTAA-CAACGCAGAGTAC(T)$_{30}$N$_1$N3') which contained a 3' anchor sequence. 3' race was performed using a 5' gene specific primer (5'GGCACAGAGCTGCTCCACAGGCACCAT 3') derived from the *Homo sapiens* cDNA clone 138761 similar to bovine P08858 neurokinin B precursor. The resulting PCR fragment was gel purified following gel electrophoresis and cloned into the expression vector pGEM-T Easy. The resulting clones were sequenced and compared to submitted sequences in the GenBank database using the BLAST program (Altschul, S. F., et al (1990) J. Mol. Biol. 215:403-410).

Example 2

Semi-Quantitative PCR to Measure NKB in Placenta

Semi-quantitative PCR as described below was used to measure the mRNA expression of neurokinin B in placenta collected at 9 weeks, 13 weeks and at term. This showed differences in a degree of expression between the first trimester and term placenta. Expression levels were up by five times at term, as shown in FIG. 5.

SMART RACE placental cDNA was amplified using a 5' gene specific primer (5'GGCACAGAGCTGCTCCACAG-GCACCAT 3') derived from the *Homo sapiens* cDNA clone 138761 similar to bovine P08858 neurokinin B precursor and a 3' SMART anchor sequence primer. A specified primer pair for β-actin was used for normalisation. PCRs were performed using twenty-one cycles of 95° C. for 30 sec and 68° C. for 2 min. The primers were chosen deliberately to have high annealing temperatures so that the PCR reactions could be performed two step to reduce the possibility of non-specific products being formed. The number of cycles required to obtain a reproducible exponential amplification of the β-actin RT-PCR product was determined by terminating control reactions at 15, 18, 21, 24 and 30 cycles respectively. These experiments were used to check the accuracy, efficiency and amount of total RNA needed to obtain a semi-quantitative amplification in order to optimise the levels of β-actin PCR product produced. The PCR products were visualised by UV illumination following electrophoresis (A 1 kb DNA ladder (MI) and 100 bp DNA ladder (M2) are shown in FIG. 5 also).

Example 3

Neurokinin B Extraction from Placental Tissue and Plasma

Testing of placental extracts using the techniques set out below revealed neurokinin B to be present in significant amounts and its chromatographic properties in HPLC were identical to synthetic neurokinin B. It also displayed the same degree of loss of hydrophobicity (on HPLC) after oxidising its methionine residues. Oxidisation was found to give three peaks of double oxidised (1), single oxidised (2) and non-oxidised forms (3), see FIG. 6. FIG. 6(a) shows oxidised and reduced neurokinin B separated by RPHPLC from human pregnancy plasma and FIG. 6(b) shows separation of condensed and reduced neurokinin by RPHPLC extracted from human term placenta.

Extraction of Neurokinin B from Placenta

Whole placentae were weighed and washed immediately after delivery with 150 mM sodium chloride solution containing 10 mM EDTA at pH 7.5. A tissue sample not exceeding 100 g was excised and homogenised in 100 ml saline/EDTA solution using a blender with a glass vessel. Protease inhibitors, phenylmethylsulphonylfluoride, N-ethylmaleiimide, and pepstatin were added from a stock solution in methanol. After 20 seconds 800 ml of methanol were added and blending was continued for a further minute. The mixture was decanted into 200 ml polypropylene centrifuge tubes and subjected to centrifugation at 4° C. and 3000×g for 30 minutes. The supernatant was separated and stored overnight at 4° C. resulting in further precipitation that was removed by centrifugation. The volume of each extract was reduced to less than one eighth of the initial volume and then diluted by addition of three volumes of water containing 0.1% trifluoroacetic acid (TFA). Any trace of suspended matter was removed by a final centrifugation step. The volume of extract was recorded and an amount corresponding to 20 g of placenta reserved for solid phase extraction using Sep-Pak C18 3CC cartridges (Waters Chromatography Division, Millipore Corporation, Milford, Mass., U.S.A.). Cartridges were primed prior to use by perfusion with 2 ml of the following solutions; 1) water containing 0.1% TFA and 0.1% Polypep gelatine hydrolysate (Sigma-Aldrich, Poole, UK), 2) water containing 0.1% TFA, 3) water containing 80% v/v acetonitrile and 4) water containing 0.1% TFA. Each extract was passed through a prepared cartridge, which was then washed with 2 ml 0.1% TFA in water, 2 ml 0.1% TFA in water containing acetonitrile 10% and 20% TFA. The column was eluted with 2 ml of 30%, 40% and 50% acetonitrile in water containing 0.1% TFA. Eluted fractions were reduced to dryness under vacuum after adding 1 mg of mannitol and 100 µg Polypep. Smaller placentae obtained from abortions were treated as above but dissociated in a glass homogeniser retaining the same proportions of buffer and methanol to placental weight.

Extraction of Neurokinin B from Plasma

Neurokinin B standards were prepared in pooled plasma from the blood of five young males taken into EDTA. The standards contained 1280, 640, 320, 160 and 80 pg/ml neurokinin B. Each 2 ml of sample of plasma standard was acidified by addition of 220 µl 1M HCl containing 0.21M glycine. They were then diluted to 10 ml with 0.9% saline and subjected to centrifugation at 3000×g for 20 minutes to ensure complete clarity. Sep-Pak C18 1CC cartridges were primed as described above for Sep-Pak C18 3CC cartridges. After loading, cartridges were washed with 1 ml 0.1 M HCl containing 0.02M glycine followed by 1 ml 0.1% TFA in water. Further washes with 1 ml 0.1% TFA in water containing 10 and 20% acetonitrile were followed by elution with 1 ml 0.1% TFA in a mixture of 50% water and acetonitrile. Eluted fractions were reduced to dryness under vacuum after adding 1 mg of mannitol and 100 µg Polypep. The acidification step ensured that we were extracting already processed mature peptide as it is possible that inactive circulating precursor could be cleaved by endogenous plasma proteases to produce immunoreactive peptides unless precautions are taken.

Example 4

Measurement of NKB in Placental Tissues and Plasma

Placental and plasma extracts were reconstituted in 500 µl of buffer supplied as part of a commercial neurokinin B radioimmunoassay kit RIK 7357 by Peninsula Laboratories, Belmont, Calif., USA to which had added 0.2% Igepal CA-630 non-ionic detergent (Sigma). Sub-samples of 25 µl were taken from extracted and non-extracted standards and mixed with 75 µl of the above buffer. Standards were prepared in buffer containing Igepal, but to which had been added 200 µg/ml Polypep. Anti-neurokinin antibody solution (100 µl)

was added to all assay tubes except blanks and the assay was conducted as described in the "General Protocol for Radioimmunoassay Kit" instructions. Assays were performed in duplicate and results were corrected with reference to extracted standards.

The plasma and placental levels of neurokinin B in various human volunteers and rats were measured by the above methods. The results of the plasma samples are summarised in Table 1. Placental samples were collected from weeks 7 to 15 of pregnancy, and all seven were shown to contain equivalent significant amounts of neurokinin B; however concentrations of plasma NKB detected at term were in the 100 picomolar range that would be expected to have effects on the maternal cardiovasculature. Plasma samples taken from non-pregnant volunteers all had low levels of the peptide, as did the majority of plasma samples taken from individuals who had been admitted for elective abortions at weeks 7 to 15. Four samples from this latter group had concentrations equivalent to those found at term. This suggests that the placenta from this individual may have started to secrete supra-physiological concentrations of neurokinin B early in pregnancy. Samples of patients in late pregnancy suffering from hypertension and pre-eclampsia all had concentrations in the nanomolar range suggesting that raised neurokinin B may be responsible for their symptoms.

TABLE 1

| Week of Pregnancy | Nmol/l NKB in normotensive pregnancies |
|---|---|
| 6 | 0 |
| 9 | 0 |
| 9 | 0.97 |
| 10 | 0.535 |
| 13 | 0 |
| 13 | 0 |
| 13 | 0.083 |
| 13 | 0.511 |
| 14 | 0 |
| 14 | 0 |
| 14 | 0.511 |
| 17 | 0.182 |
| 17 | 0.182 |
| 18 | 0 |
| 23 | 0.12 |
| 24 | 0 |
| 25 | 0.17 |
| 27 | 0 |
| 28 | 0 |
| 28 | 0.033 |
| 31 | 0 |

TABLE 1-continued

| Week of Pregnancy | Nmol/l NKB in normotensive pregnancies |
|---|---|
| 31 | 0.031 |
| 32 | 0 |
| 33 | 0 |
| 37 | 0 |
| 38 | 0.07 |
| 39 | 0.138 |
| 40 | 0.05 |
| 40 | 0.2 |
| 41 | 0.118 |

TABLE 2

| Week of pregnancy | Nmol/l NKB in pre-eclamptic pregnancies |
|---|---|
| 30 | 3.964 |
| 34 | 6.156 |
| 36 | 3.796 |
| 37 | 2.141 |
| 38 | 2.752 |
| 39 | 2.004 |
| 39 | 6.288 |
| 39 | 0.98 |

TABLE 3

| Patient number | Nmol/l NKB in normotensive pregnancies at term |
|---|---|
| 1 | 0 |
| 2 | 0 |
| 3 | 0 |
| 4 | 0 |
| 5 | 0 |
| 6 | 0 |
| 7 | 0 |
| 8 | 0.084 |
| 9 | 0.118 |
| 10 | 0.143 |
| 11 | 0.22 |
| 12 | 0.226 |
| 13 | 0.228 |
| 14 | 0.398 |
| 15 | 0.521 |
| 16 | 1.317 |

The invention claimed is:

1. A method for predicting or diagnosing in a human subject a medical condition selected from the group consisting of pregnancy-induced hypertension, pre-eclampsia, and related foetal complications, the method comprising collecting a biological sample from said human subject, measuring a concentration in said biological sample of human neurokinin B precursor, or human neurokinin B, wherein an elevated concentration of human neurokinin B precursor or human neurokinin B is predictive or diagnostic of said medical condition.

2. The method of claim 1, wherein the biological sample comprises a volume of blood.

3. The method of claim 1, wherein the neurokinin B precursor has the amino acid sequence of SEQ ID NO:1.

4. The method of claim 1, wherein the step of measuring the concentration of human neurokinin B precursor, or comprises the use of a binding partner of capable of binding to human neurokinin B precursor or a human neurokinin B.

5. The method of claim 1 wherein the concentration of human neurokinin B precursor is measured.

6. The method of claim 1 wherein the concentration of a of human neurokinin B is measured.

7. The method of claim 6 wherein the neurokinin B has the amino acid sequence of SEQ ID NO:2.

* * * * *

UNITED STATES PATENT AND TRADEMARK OFFICE
CERTIFICATE OF CORRECTION

| | | |
|---|---|---|
| PATENT NO. | : 7,947,458 B1 | |
| APPLICATION NO. | : 10/130340 | |
| DATED | : May 24, 2011 | |
| INVENTOR(S) | : Nigel Page and Phillip Lowry | |

It is certified that error appears in the above-identified patent and that said Letters Patent is hereby corrected as shown below:

Column 58

In claim 4, at line 11, after the word "or", insert -- human neurokinin B --; and In claim 6, at line 16, after the word "a", delete "of.".

Signed and Sealed this
Second Day of August, 2011

David J. Kappos
*Director of the United States Patent and Trademark Office*